United States Patent
Yan et al.

(10) Patent No.: US 6,740,513 B2
(45) Date of Patent: *May 25, 2004

(54) ISOLATED HUMAN KINASE PROTEINS, NUCLEIC ACID MOLECULES ENCODING HUMAN KINASE PROTEINS, AND USES THEREOF

(75) Inventors: Chunhua Yan, Boyds, MD (US); Karen A. Ketchum, Germantown, MD (US); Valentina Difrancesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/135,696

(22) Filed: May 1, 2002

(65) Prior Publication Data

US 2003/0166215 A1 Sep. 4, 2003

Related U.S. Application Data

(62) Division of application No. 09/978,197, filed on Oct. 17, 2001, now Pat. No. 6,403,353, which is a division of application No. 09/813,817, filed on Mar. 22, 2001, now Pat. No. 6,340,583.

(51) Int. Cl.$^7$ ............ C12N 9/12; C12N 15/00; C12N 5/00; C12N 21/04; C07H 21/04
(52) U.S. Cl. ............ 435/194; 435/320.1; 435/325; 435/6; 435/252.3; 536/23.1
(58) Field of Search ............ 435/194, 6, 252.3, 435/325, 320.1; 536/23.2

(56) References Cited

PUBLICATIONS

Okana et al. "Identification and Characterization of a Novel Family of Serine/Threonine Kinases Containing Two–N–Terminal LIM Motifs." J. Biol. Chem., Dec. 1995, vol. 52, pp. 3.321–31330.

International Search Report dated Dec. 3, 2002.

*Primary Examiner*—Maryam Monshipouri
(74) *Attorney, Agent, or Firm*—Celera Genomics; Justin D. Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

14 Claims, 34 Drawing Sheets

```
   1 CCCAGGGCGC CGTAGGCGGT GCATCCCGTT CGCGCCTGGG GCTGTGGTCT
  51 TCCCGCGCCT GAGGCGGCGG CGGCAGGAGC TGAGGGGAGT TGTAGGGAAC
 101 TGAGGGGAGC TGCTGTGTCC CCCGCCTCCT CCTCCCCATT TCCGCGCTCC
 151 CGGGACCATG TCCGCGCTGG CGGGTGAAGA TGTCTGGAGG TGTCCAGGCT
 201 GTGGGGACCA CATTGCTCCA AGCCAGATAT GGTACAGGAC TGTCAACGAA
 251 ACCTGGCACG GCTCTTGCTT CCGGTGAAAG TGATGCGCAG CCTGGACCAC
 301 CCCAATGTGC TCAAGTTCAT TGGTGTGCTG TACAAGGATA AGAAGCTGAA
 351 CCTGCTGACA GAGTACATTG AGGGGGGCAC ACTGAAGGAC TTTCTGCGCA
 401 GTATGGATCC GTTCCCCTGG CAGCAGAAGG TCAGGTTTGC CAAAGGAATC
 451 GCCTCCGGAA TGGACAAGAC TGTGGTGGTG GCAGACTTTG GGCTGTCACG
 501 GCTCATAGTG GAAGAGAGGA AAAGGGCCCC CATGGAGAAG CCACCACCA
 551 AGAAACGCAC CTTGCGCAAG AACGACCGCA AGAAGCGCTA CACGGTGGTG
 601 GGAAACCCCT ACTGGATGGC CCCTGAGATG CTGAACGAAA AGAGCTATGA
 651 TGAGACGGTG GATATCTTCT CCTTTGGGAT CGTTCTCTGT GAGATCATTG
 701 GGCAGGTGTA TGCAGATCCT GACTGCCTTC CCCGAACACT GGACTTTGGC
 751 CTCAACGTGA AGCTTTTCTG GGAGAAGTTT GTTCCCACAG ATTGTCCCCC
 801 GGCCTTCTTC CCGCTGGCCG CCATCTGCTG CAGACTGGAG CCTGAGAGCA
 851 GACCAGCATT CTCGAAATTG GAGGACTCCT TTGAGGCCCT CTCCCTGTAC
 901 CTGGGGGAGC TGGGCATCCC GCTGCCTGCA GAGCTGGAGG AGTTGGACCA
 951 CACTGTGAGC ATGCAGTACG GCCTGACCCG GGACTCACCT CCCTAGCCCT
1001 GGCCCAGCCC CCTGCAGGGG GGTGTTCTAC AGCCAGCATT GCCCCTCTGT
1051 GCCCCATTCC TGCTGTGAGC AGGGCCGTCC GGGCTTCCTG TGGATTGGCG
1101 GAATGTTTAG AAGCAGAACA AACCATTCCT ATTACCTCCC CAGGAGGCAA
1151 GTGGGCGCAG CACCAGGGAA ATGTATCTCC ACAGGTTCTG GGGCCTAGTT
1201 ACTGTCTGTA AATCCAATAC TTGCCTGAAA GCTGTGAAGA AGAAAAAAAC
1251 CCCTGGCCTT TGGGCCAGGA GGAATCTGTT ACTCGAATCC ACCCAGGAAC
1301 TCCCTGGCAG TGGATTGTGG GAGGCTCTTG CTTACACTAA TCAGCGTGAC
1351 CTGGACCTGC TGGGCAGGAT CCCAGGGTGA ACCTGCCTGT GAACTCTGAA
1401 GTCACTAGTC CAGCTGGGTG CAGGAGGACT TCAAGTGTGT GGACGAAAGA
1451 AAGACTGATG GCTCAAAGGG TGTGAAAAAG TCAGTGATGC TCCCCCTTTC
1501 TACTCCAGAT CCTGTCCTTC CTGGAACAGG GTTGAGGGAG TAGGTTTTGA
1551 AGAGTCCCTT AATATGTGGT GGAACAGGCC AGGAGTTAGA GAAAGGGCTG
1601 GCTTCTGTTT ACCTGCTCAC TGGCTCTAGC CAGCCCAGGG ACCACATCAA
1651 TGTGAGAGGA AGCCTCCACC TCATGTTTTC AAACTTAATA CTGGAGACTG
1701 GCTGAGAACT TACGGACAAC ATCCTTTCTG TCTGAAACAA ACAGTCACAA
1751 GCACAGGAAG AGGCTGGGGG ACTAGAAAGA GGCCCTGCCC TCTAGAAAGC
1801 TCAGATCTTG GCTTCTGTTA CTCATACTCG GGTGGGCTCC TTAGTCAGAT
1851 GCCTAAAACA TTTTGCCTAA AGCTCGATGG GTTCTGGAGG ACAGTGTGGC
1901 TTGTCACAGG CCTAGAGTCT GAGGGAGGGG AGTGGAGTC TCAGCAATCT
1951 CTTGGTCTTG GCTTCATGGC AACCACTGCT CACCCTTCAA CATGCCTGGT
2001 TTAGGCAGCA GCTTGGGCTG GGAAGAGGTG GTGGCAGAGT CTCAAAGCTG
2051 AGATGCTGAG AGAGATAGCT CCCTGAGCTG GGCCATCTGA CTTCTACCTC
2101 CCATGTTTGC TCTCCCAACT CATTAGCTCC TGGGCAGCAT CCTCCTGAGC
2151 CACATGTGCA GGTACTGGAA AACCTCCATC TTGGCTCCCA GAGCTCTAGG
2201 AACTCTTCAT CACAACTAGA TTTGCCTCTT CTAAGTGTCT ATGAGCTTGC
2251 ACCATATTTA ATAAATTGGG AATGGGTTTG GGGTATTAAA AAAAAAAAAA
2301 AAAAAAAAAA AAAAAAAAA  (SEQ ID NO:1)
```

FEATURES:
5'UTR:       1-228
Start Codon: 229
Stop Codon:  994
3'UTR:       997

FIGURE 1A

Homologous proteins:
Top 10 BLAST Hits

|  | Score | E |
|---|---|---|
| CRA\|1000682328847 /altid=gi\|8051618 /def=ref\|NP_057952.1\| LIM d... | 485 | e-136 |
| CRA\|18000005015874 /altid=gi\|5031869 /def=ref\|NP_005560.1\| LIM ... | 485 | e-136 |
| CRA\|88000001156379 /altid=gi\|7434382 /def=pir\|\|JC5814 LIM motif... | 469 | e-131 |
| CRA\|88000001156378 /altid=gi\|7434381 /def=pir\|\|JC5813 LIM motif... | 469 | e-131 |
| CRA\|18000005154371 /altid=gi\|7428032 /def=pir\|\|JE0240 LIM kinas... | 469 | e-131 |
| CRA\|18000005126937 /altid=gi\|6754550 /def=ref\|NP_034848.1\| LIM ... | 469 | e-131 |
| CRA\|18000005127186 /altid=gi\|2804562 /def=dbj\|BAA24491.1\| (AB00... | 469 | e-131 |
| CRA\|18000005127185 /altid=gi\|2804553 /def=dbj\|BAA24489.1\| (AB00... | 469 | e-131 |
| CRA\|18000005004416 /altid=gi\|2143830 /def=pir\|\|I78847 LIM motif... | 468 | e-131 |
| CRA\|18000005004415 /altid=gi\|1708825 /def=sp\|P53670\|LIK2_RAT LI... | 468 | e-131 |

BLAST dbEST hits:

|  | Score | E |
|---|---|---|
| gi\|10950740 /dataset=dbest /taxon=96... | 1049 | 0.0 |
| gi\|10156485 /dataset=dbest /taxon=96... | 975 | 0.0 |
| gi\|5421647 /dataset=dbest /taxon=9606 ... | 952 | 0.0 |
| gi\|10895718 /dataset=dbest /taxon=96... | 757 | 0.0 |
| gi\|13043102 /dataset=dbest /taxon=960... | 714 | 0.0 |
| gi\|519615 /dataset=dbest /taxon=9606 /... | 531 | e-149 |
| gi\|11002869 /dataset=dbest /taxon=96... | 511 | e-143 |

EXPRESSION INFORMATION FOR MODULATORY USE:
library source:
From BLAST dbEST hits:
gi\|10950740    teratocarcinoma
gi\|10156485    ovary
gi\|5421647     testis
gi\|10895718    nervous_normal
gi\|13043102    bladder
gi\|519615      infant brain
gi\|11002869    thyroid gland From tissue screening panels:
Fetal whole brain

FIGURE 1B

```
  1 MVQDCQRNLA RLLLPVKVMR SLDHPNVLKF IGVLYKDKKL NLLTEYIEGG
 51 TLKDFLRSMD PFPWQQKVRF AKGIASGMDK TVVVADFGLS RLIVEERKRA
101 PMEKATTKKR TLRKNDRKKR YTVVGNPYWM APEMLNGKSY DETVDIFSFG
151 IVLCEIIGQV YADPDCLPRT LDFGLNVKLF WEKFVPTDCP PAFFPLAAIC
201 CRLEPESRPA FSKLEDSFEA LSLYLGELGI PLPAELEELD HTVSMQYGLT
251 RDSPP     (SEQ ID NO:2)
```

FEATURES:
Functional domains and key regions:
[1] PDOC00004 PS00004 CAMP_PHOSPHO_SITE
cAMP- and cGMP-dependent protein kinase phosphorylation site Number of matches: 2
    1     108-111  KKRT
    2     119-122  KRYT

[2] PDOC00005 PS00005 PKC_PHOSPHO_SITE
Protein kinase C phosphorylation site

Number of matches: 4
    1     51-53   TLK
    2     106-108  TTK
    3     107-109  TKK
    4     111-113  TLR

[3] PDOC00006 PS00006 CK2_PHOSPHO_SITE
Casein kinase II phosphorylation site

Number of matches: 4
    1     51-54   TLKD
    2     76-79   SGMD
    3     139-142  SYDE
    4     212-215  SKLE

[4] PDOC00008 PS00008 MYRISTYL
N-myristoylation site

Number of matches: 4
    1     73-78   GIASGM
    2     77-82   GMDKTV
    3     150-155  GIVLCE
    4     158-163  GQVYAD Membrane spanning structure and domains:

| Helix | Begin | End | Score | Certainty |
|---|---|---|---|---|
| 1 | 142 | 162 | 0.872 | Putative |
| 2 | 184 | 204 | 0.652 | Putative |

FIGURE 2A

BLAST Alignment to Top Hit:
>CRA|1000682328847 /altid=gi|8051618 /def=ref|NP_057952.1| LIM
    domain kinase 2 isoform 2b [Homo sapiens] /org=Homo
    sapiens /taxon=9606 /dataset=nraa /length=617
    Length = 617

Score = 485 bits (1235), Expect = e-136
Identities = 241/265 (90%), Positives = 241/265 (90%), Gaps = 22/265 (8%)

```
Query:  13 LLPVKVMRSLDHPNVLKFIGVLYKDKKLNLLTEYIEGGTLKDFLRSMDPFPWQQKVRFAK  72
              VKVMRSLDHPNVLKFIGVLYKDKKLNLLTEYIEGGTLKDFLRSMDPFPWQQKVRFAK
Sbjct: 353 LTEVKVMRSLDHPNVLKFIGVLYKDKKLNLLTEYIEGGTLKDFLRSMDPFPWQQKVRFAK 412

Query:  73 GIASGM---------------------DKTVVVADFGLSRLIVEERKRAPMEKATTKKR 110
           GIASGM                     DKTVVVADFGLSRLIVEERKRAPMEKATTKKR
Sbjct: 413 GIASGMAYLHSMCIIHRDLNSHNCLIKLDKTVVVADFGLSRLIVEERKRAPMEKATTKKR 472

Query: 111 TLRKNDRKKRYTVVGNPYWMAPEMLNGKSYDETVDIFSFGIVLCEIIGQVYADPDCLPRT 170
           TLRKNDRKKRYTVVGNPYWMAPEMLNGKSYDETVDIFSFGIVLCEIIGQVYADPDCLPRT
Sbjct: 473 TLRKNDRKKRYTVVGNPYWMAPEMLNGKSYDETVDIFSFGIVLCEIIGQVYADPDCLPRT 532

Query: 171 LDFGLNVKLFWEKFVPTDCPPAFFPLAAICCRLEPESRPAFSKLEDSFEALSLYLGELGI 230
           LDFGLNVKLFWEKFVPTDCPPAFFPLAAICCRLEPESRPAFSKLEDSFEALSLYLGELGI
Sbjct: 533 LDFGLNVKLFWEKFVPTDCPPAFFPLAAICCRLEPESRPAFSKLEDSFEALSLYLGELGI 592

Query: 231 PLPAELEELDHTVSMQYGLTRDSPP 255
           PLPAELEELDHTVSMQYGLTRDSPP
Sbjct: 593 PLPAELEELDHTVSMQYGLTRDSPP 617  (SEQ ID NO:4)
```

Hmmer search results (Pfam):

| Model | Description | Score | E-value | N |
|---|---|---|---|---|
| PF00069 | Eukaryotic protein kinase domain | 100.1 | 1.1e-26 | 2 |
| CE00031 | CE00031 VEGFR | 4.9 | 0.14 | 1 |
| CE00204 | CE00204 FIBROBLAST_GROWTH_RECEPTOR | 4.7 | 1 | 1 |
| CE00359 | E00359 bone_morphogenetic_protein_receptor | 1.8 | 7.9 | 1 |
| CE00022 | CE00022 MAGUK_subfamily_d | 1.5 | 2.5 | 1 |
| CE00287 | CE00287 PTK_Eph_orphan_receptor | -48.4 | 3.8e-05 | 1 |
| CE00292 | CE00292 PTK_membrane_span | -61.8 | 2.1e-05 | 1 |
| CE00291 | CE00291 PTK_fgf_receptor | -113.0 | 0.027 | 1 |
| CE00286 | E00286 PTK_EGF_receptor | -125.1 | 0.0021 | 1 |
| CE00290 | CE00290 PTK_Trk_family | -151.3 | 6.5e-05 | 1 |
| CE00288 | CE00288 PTK_Insulin_receptor | -210.4 | 0.014 | 1 |

Parsed for domains:

| Model | Domain | seq-f | seq-t | hmm-f | hmm-t | | score | E-value |
|---|---|---|---|---|---|---|---|---|
| PF00069 | 1/2 | 16 | 79 | .. | 41 | 105 .. | 52.1 | 2.3e-13 |
| CE00022 | 1/1 | 124 | 153 | .. | 187 | 216 .. | 1.5 | 2.5 |
| PF00069 | 2/2 | 81 | 156 | .. | 129 | 182 .. | 48.0 | 3.1e-12 |
| CE00031 | 1/1 | 129 | 156 | .. | 1114 | 1141 .. | 4.9 | 0.14 |
| CE00204 | 1/1 | 129 | 156 | .. | 705 | 732 .. | 4.7 | 1 |
| CE00359 | 1/1 | 79 | 157 | .. | 287 | 356 .. | 1.8 | 7.9 |
| CE00290 | 1/1 | 9 | 218 | .. | 1 | 282 [] | -151.3 | 6.5e-05 |
| CE00287 | 1/1 | 1 | 218 | [. | 1 | 260 [] | -48.4 | 3.8e-05 |
| CE00291 | 1/1 | 1 | 218 | [. | 1 | 285 [] | -113.0 | 0.027 |
| CE00292 | 1/1 | 1 | 218 | [. | 1 | 288 [] | -61.8 | 2.1e-05 |
| CE00288 | 1/1 | 1 | 218 | [. | 1 | 269 [] | -210.4 | 0.014 |
| CE00286 | 1/1 | 6 | 218 | .. | 1 | 263 [] | -125.1 | 0.0021 |

FIGURE 2B

```
   1 TCATCCTTGC GCAGGGGCCA TGCTAACCTT CTGTGTCTCA GTCCAATTTT
  51 AATGTATGTG CTGCTGAAGC GAGAGTACCA GAGGTTTTTT TGATGGCAGT
 101 GACTTGAACT TATTTAAAAG ATAAGGAGGA GCCAGTGAGG GAGAGGGGTG
 151 CTGTAAAGAT AACTAAAAGT GCACTTCTTC TAAGAAGTAA GATGGAATGG
 201 GATCCAGAAC AGGGGTGTCA TACCGAGTAG CCCAGCCTTT GTTCCGTGGA
 251 CACTGGGGAG TCTAACCCAG AGCTGAGATA GCTTGCAGTG TGGATGAGCC
 301 AGCTGAGTAC AGCAGATAGG GAAAAGAAGC CAAAAATCTG AAGTAGGGCT
 351 GGGGTGAAGG ACAGGGAAGG GCTAGAGAGA CATTTGGAAA GTGAAACCAG
 401 GTGGATATGA GAGGAGAGAG TAGAGGGTCT TGATTTCGGG TCTTTCATGC
 451 TTAACCCAAA GCAGGTACTA AAGTATGTGT TGATTGAATG TCTTTGGGTT
 501 TCTCAAGACT GGAGAAAGCA GGGCAAGCTC TGGAGGGTAT GGCAATAACA
 551 AGTTATCTTG AATATCCTCA TGGTGGAAAG TCCTGATCCT GTTTGAATTT
 601 TGGAAATAGA AATCATTCAG AGCCAAGAGA TTGAATTGTT GAGTAAGTGG
 651 GTGGTCAGGT TACAGACTTA ATTTTGGGTT AAAAAGTAAA AACAAGAAAC
 701 AAGGTGTGGC TCTAAAATAA TGAGATGTGC TGGGGGTGGG GCATGGCAGC
 751 TCATAAACTG ACCCTGAAAG CTCTTACATG TAAGAGTTCC AAAAATATTT
 801 CCAAAACTTG GAAGATTCAT TTGGATGTTT GTGTTCATTA AAATCTCTCA
 851 CTAATTCATT GTCTTGTCCA CTGTCCGTAA CCCAACCTGG GATTGGTTTG
 901 AGTGAGTCTC TCAGACTTTC TGCCTTGGAG TTTGTGAGAG AGATGGCATA
 951 CTCTGTGACC ACTGTCACCC TAAAACCAAA AAGGCCCCTC TTGACAAGGA
1001 GTCTGAGGAT TTTAGACCCA GGAAGAATGA GTGATGGGCA TATATATATC
1051 CTATTACTGA GGCATGAGAA GAGTGGAATG GGTGGGTTGA GGTGGTGTTT
1101 TAAGGCCTCT TGCCAGCTTG TTTAACTCTT CTCTGGGGAA CGAGGGGGAC
1151 AACTGTGTAC ATTGGCTGCT CCAGAATGAT GTTGAGCAAT CTTGAAGTGC
1201 CAGGAGCTGT GCTTTGTCTA TTCATGGCCC CTGTGCCTGT GAAACAGGGT
1251 TCGGTGACTG TCACTGTGCC TGTGGCAGTC TGTAGTTACC CAGAGAGAAC
1301 AAAGCTGCAT ACACAGAGCG CACAAGGGAG TCTTGTAACA ACCTTGTCCT
1351 GCTTTCTAGG GCTGAGTCAG GTACCACAGC TTGATCTCAG CTGTCCTCTT
1401 TATTTCAAGA AGTTGACATC TGAGCCATAC CAGGAGTATT GTATTTTGTT
1451 TGAGGCCTCT CTTTTTGGAG GAACATGGAC CGACTCTGTG CTTTTGTCTA
1501 TGCTGGTCTC TGAGCTCACA CAACCCTTCA CCCTCCTTTC TCAGCCAGTG
1551 ATAGGTAAGT CTTCCCTATC TTGCAAGGCT CAGCTCAAGT GTCAGCTTCC
1601 TCTACAAAGA CTTTCCTGGT TCCCCTCATT GGAGTGAACA AGAGTTGACA
1651 TGGTAGAATG GAAAGAGCAG AAGCTTTAGA ATGAGCCAGA CCTGAGTATG
1701 AATGCTAGAT CCACCACTTA GCTAGTCAAC CCTGCCCCCT GCCTCAAGTT
1751 TTAATTTTCC TATCCATTAA GTGAATATAA TAATACCTGT GTCACAGGAT
1801 TATTTTGAGA ATTAAATGAG ATTAGGTCTA TGAAAGCACC TAGCAGAGTT
1851 CTTGGCATAT AGGAGGCATT CATTAAATAT TTGTTCTTCC CCTTTTATAC
1901 CCATTACTTT TCTTTTTCTG AACTAAAATA ATACTTGGTT CTATCTCTGA
1951 AATAACATCC AAGTGAAAAA TCAACAACAT GAAAGAGCAG TTCTTTTCCA
2001 GTGGATTTGC TTCTTAAGGA GCAGAGATTA TGTAATCTAA CAGCCTCCAA
2051 CATACAAAGA GCTTTGTATC TAGAACAGGG GTCCCCAGCC CCTGGACCGC
2101 CAACTGGTAC GGGTCTGTAG CCTGTTAGGA ACCAGGCTGC ACAGCAGGAG
2151 GTGAGCGGCG GGCCAGTGAG CATTGCTGCC TGAGCTCTGC CTCCTGTCAG
2201 ATCAGTGGTG GCATTAGATT CTCATAGGAG TGTGAACCCT ATTGTGAACT
2251 GCACATGCAA GGGATCTGGG TTGCATGCTC CTTATGAGAA TCTCACTAAT
2301 GGCTGATGAT CTGAGTTGGA ACAGTTTGAT ACCAAAACCA TCCCCCCGCC
2351 CCCCAACCCC CAGCCTAGGG TCCGTGGAAA AATTGGCCCC TGGTGCCAAA
2401 AAGGTTGAGG ACTGCTGATC TAGAGGACCA ATTTATTCAA TGTTGGTTGA
2451 GTAAATGAGC TCTTGGATTA GGTGATGGAA AAATCTGAAA AAACAGGGCT
2501 TTTGAGGAAT AGGAAAAGGC AGTAACATGT TTAACCCAGA GAGAAGTTTC
2551 TGGCTGTTGG CTGGGAATAG TCATAGGAAG GGCTGACACT GAAAAGAAGG
2601 AGATTGTGTT CGTTTCTTCT TCTCAGAGCT ATAAGCAAAG GCTGAAAGTT
2651 CTAGAAAAAG GCAAGTTTTG TTTCAGTAGA AAAAAGGATA ATCAGAACCA
2701 TTTTTAGAAA ATGGAATGAG ACTACTTTTG AGGCCATGAG TTCCTTGTCC
2751 CTGGAGAGAT GAGCAGAGGT TGGACAAGTG CTTACCAGAG ATCTTGTGGA
2801 GGCAGAAACT GTGCATCTAG CAGAGCATTG GCCTAACCCT TTCAAATGAG
2851 ATGCTGTTAA CTCAGTCTTA TTCTACATGG TAGGAATCCT GTCCCTTTGC
2901 CTCCTGCTAC TTTGGGCCTC TCAACCTCTT GGTTTTGTGT GCAGGTGAAG
```

FIGURE 3-1

```
2951 ATGTCTGGAG GTGTCCAGGC TGTGGGGACC ACATTGCTCC AAGCCAGATA
3001 TGGTACAGGA CTGTCAACGA AACCTGGCAC GGCTCTTGCT TCCGGTAGGT
3051 GGGCCTATCC TCCCATCTTT ACCAGTGTAC TATGGGCCAA GCACTATTTC
3101 ATGTTCTGAT GGAAAACACA GAAACAAGCT TCTGAGTTGA GAATTTCAAT
3151 CTTAGGGTGG GGAAAGGAAT GTACCAAGGA AGAGCTCATG ACCAAACCTC
3201 AAGTGTGGCC CCCCTGAACC CAGGTTAAAT TGGAAGAGCC ATAAATGGGC
3251 CAGCTGGAGG CAGGGTGGGG GGATGAGAGG AGCCCTTTCC AGGGTTGTCC
3301 CATATCCCTC ACTTTATGGG TGAGGAAACT GAGGCCCAGG AAGAGTGACT
3351 TTCCTGTGGC TGCACTACAG ATTATGCAGG TACTTCAAGA GTTGTTTGTA
3401 TTCTTATTTT ATTTTATTTT ATTTTATTTT ATTTTATTTT ATTTTATGAG
3451 AGGGATTCTT GCTGTTGCCC AGGCTGGAGT GCAGTGGTGC AATCTCGGCT
3501 CACTGCAATC TCTGCCTGCT GGGTTCAAGT GATTTTTCTG CCTTAGCTTC
3551 CTGAGTAGCT GAGATGACAG GCACCTGCCA CCATGCGCAG CTAATTTTTG
3601 TATTTTAGTG GAGACGGGGG TTTCAACATG TTGGTCAGGC TGGTCTTGAA
3651 CTCCTGACCT CAAATGATGC ACCCACCTCG ACCTCCCAAA GTGCTGGAAT
3701 TACAGGCGTG AACCACTGTG CCCAGCCAAG AGTTGTTTTT AGTGTGGTTG
3751 GCAGAGCCAG CTCTTCCTTC ACCACAGGAT GCCTCCCTAG GTTCCTACTT
3801 TTTGTTACTA GCTTTTATTA TAGCTATATT ATTATTATTA TTATTATTAT
3851 TATTATTATT ATTATTGAGA CAGAGTCTCG CTCTGTCGCC CAGGCTGGTG
3901 TACAGTGGTG CGATCCCGGG CTCACTGCAA CCTCTGCCTC CCGAGTTCAA
3951 GCAGTTCTCC TGCCTCAGCC CCCGAGTAG GTGGGACTAC AGGCGCCTGC
4001 CACCACACCC GGCTAATTTT TGTATTTTTA GTAGAGACGG GGTTTCACCT
4051 TGTTGACCAG GCTGGTCTGG AGCTCCTGAC CTCAGGTAAG TGCTAGAATC
4101 ACAGGCGTGA ACCACTGCGC CCAGCCAAGA GTTGTTTTTA GTGTGGTTGG
4151 CAGAGCCAGC TCTTCCTCAC CACAGGTTGC CTCCCTAGGT TCCTACTTTT
4201 TGTTACTAGC TTTATTATAG CTACATTATT ATTATTATTG TTATTATTAT
4251 TGAGACAGAG TCTCGCTCTG TCGCCCAGGC TGGTGTACAG TGATGTGATC
4301 TTGGCTCACT GCAACCTCTG CCCCCCGAGT TCAAGCAATT CTCCTGCTTC
4351 AGCCCCCCTA GTAGGTGGGA CTCCAGGCAC CTGCCACCAC GCCCAGCTAA
4401 TTTTTGTATT TTTAGTAGAG GCGGGGTTTC ACCTTGTTGG CCAGGCTGGT
4451 CTCAAACTCC TGACCTCAGG TGATCCGCCT GCCTCGGCCT CCCAAAATGT
4501 TGGGATTACA GGCATGAGCC ACCGCGCCCT GCCTATAGCT ACATTATTTT
4551 TGTAGGCAGC TCAGTTTCTT AAAAATTATA CAGACTTCAA ATCAGATTTG
4601 TTCCTGCTGT CTGAGGCTCA GTTTCTTCAT CTGGAAAATG GATGGTAATA
4651 ATCTTGTTGA GATTGAATGA AATAATATAT GCAGTGTATC CAGTACATGG
4701 TAGACACCCA GTGAATGGTT ATTCCTTCCT CCCATCGGAT TGGAATTCTC
4751 AAGGGTGGGA ACTTGTCTTT ATATTCTTCA CAACGTAAAA TAGTTGAAAT
4801 TTGTTGGTGG AAAGAAGAGC AGTCCACTCC AGAGGCTGGA TGGGCATGCC
4851 TGGCCCCCAA GGTCTGAAGT GGTAGGGCTG TGCCTATATC CTGAGAATGA
4901 GATAGACTAG GCAGGCACCT TGTGCTGTAG ATTCCAGCTC CTGCACATAG
4951 CTCTTGTTGT AAAACATCCC TGTGCTTATA CCAAGTAATT GAGTTGACCT
5001 TTAAACACTT GCCTCTTCCC TGGGAACCAT ATAGGGGATT GGCCTGGAGA
5051 CGTCTGGCCT CTGGAAGAGT TGGAAAGCAG CCATCATTAT TATCCTTTCC
5101 TTTCAGCTAT AACTCAGAGC TCTCAAGTCT TTTCTGTGGA TCTTATTGCC
5151 TTGGTTCTTG CCCCTTTTAC TCCCAGGGAA GTTGATTCTG TCTTTTCTGT
5201 TCCATTTAGT ATGACAGGAG CAGAGAATGT CAGAGCTGTA AGGGACCTTA
5251 TAGTTAAAGC CTTTGGCTGG TCCTTTCATT TTATAGCTGG GACTAATAAG
5301 TAACGTCAAA ACCCAATGAG TTCACAGATT GGGTCTCGCC TTGGCATGTA
5351 ACCCATATGT TCATATTCTT GCTGTTTTCC TATGTGTATG AATATTTTCT
5401 ATCCAAAATA AGCAGGACAG GGTAGAGCAA GTTAATCTTT GGAATTTCTG
5451 GATTCTCTTA GAGCTAAAAA ACTTCAGAAC TAGAAGAAAC CACCCACTAT
5501 ATGGTATAAC CCATTCATAT CACAGATGAG GCCTGAAACC AAAAAGACTT
5551 GCTCAGGCCA TGGATGACAA GAGCTGGCCC TAGCACTGAA CTCTTGGGTC
5601 ATTTGTAGGT CTAGTCAGAT GCTAGCTTGT TAGCTCTGTG CGTGCGTGTG
5651 TGTGTGTGTG TGTGTGTGTG TGTGTGAGAT AGAGACAGAA AGATAACATA
5701 TGTACACAAA TACATAAAGA GGAAGTAGAC ACGTTAGCAT GGTAGATAAG
5751 AGTACAGGCA GGCCAGGCGT GGTGGCTCAC GCCTGTAATC CCAGCACTTT
5801 GGGAGGCCAA GGCAGGTGGA TCACCTGAGG TCAGGAATTC GAGACCAGCC
5851 TGACCAACAT GGTGAAACCC CATCTCTACT AAATACAGAA AAAAATTAGC
```

FIGURE 3-2

```
5901 TTGGCATGGT GGCACATGCC TGTAATCCCA GCTACTTGGG AAGCTGAAGC
5951 AGGAGAATCG CTTGAATCCG GGAAGCAGAA GTTGCAGTGA GCCGAGATTG
6001 TGCCATTACA GTCTAGCCTG GGCAACAAGA GGGAAACTCC ATCGCAAAAA
6051 AACAACCACC ACCAAGAGTA CAGGCTATGG AATGAGACTA TGGTTTTAAA
6101 TCCTGGCTTT GCAATTTATT AACTAGCCTT AAGTGACTTC CCTGAGCTTC
6151 AGGCACCAAT CTGTAAAATG AGGATAAGAA TATTACTCAT GCCACATGGT
6201 TGTTAGGGAG GATTAAATGT GATAACCTAT ATAAAGTGGC TAGCATAGCA
6251 TCTGACATAT AGAAAACTCT TAATAGGGCC GGACGTGGTG GCTTATGCCT
6301 GTAATCCTAG CACTCTGGGA GGCCGAGGCA GAAGGATCGC TTGAGCCCAT
6351 GAGCCCAGGA GTTTGAGACC AGCCTGGCCA ACATGGCAAA ACTCCACCTC
6401 TACAAAAAAT ACAAAAATAT TAGCCAGGCG TGATGGCACA CACCTGTAGT
6451 CCCAGCTACT TGGGAAGCTG AGGAGCGATG ATTACCTGAG CCCAGGGATA
6501 TCAAGGCTGT AGTGAGCTGT GATCATGCCA CTGTACTCCA TCCAGCTGGG
6551 GGACAGAGTG AAACCCCTGT CTCAAAACAA AACAAATGAA AAAAAAAACC
6601 CTTAATAATC AGTAACTGTC ACTTTATATT ATGTTGTGAG TGTGTGTCTA
6651 TATACACCTA TATGTATACA TTTCTCTTAT TACACATTCA TTGGTGATCT
6701 GATGTGGAGC CCCAGGGATT AAGGGCAACT TTGAACTACC CTGACACAAT
6751 CAAGCCAAAT ATCATTCCCG TGGAGGAAGT AGAGTATCTA GGTTCTGTCT
6801 CCTAGTTGCA GCTTTACCTT GAGGACAGAG ACTCTAATCC AGCTGTGCTG
6851 AAGGAGCACA TCTCCTGACT TCTGAGCTTT CCCCTGGTAA ATTCAAACTG
6901 GATGTCACGG CGCCCTCAGA TAGAGCCTGG TAATTTGCCC TGGGGAGAGT
6951 GACTGTCTTT TGGATCTAAT TTGACTTTTG CCCCAGTTGG AGGAAAATCT
7001 TCAGGGCTAG GAAGGATTGT ATTTGTCTGA CCCCAGAGAT AACCTGGGTT
7051 TTGAGGAACA TGGGGCATCA ACCTGAATGG TCTTGTAAGA TCTCTCCCAC
7101 GCCAGCTTGC CAGTGTTTCT CTGATGAATT TAGAGTACCT GAGTAGTGCA
7151 GGCCTGCTGG GAGGAGGACT CTCCCTCTGT GCTACTCAGA GAAATTCATT
7201 CTTCAAGGCC CCCTTCCAGC CTTGCTCTTA CCCAGCTGGG CTACAGTTAC
7251 AATAAAGGAA ATGACTTTTC TTCTCCCCTT CCCCCAGTAC CTTTGTTTTC
7301 CTAGTCACAG GGTGGGGCTG GATATTGAAT GGAGAAATTG CTGGGGTCCA
7351 TCCTAAACTC CTCCCCTCAT CTCTCCCTTA CATTACCCCA TTCTTCTGTC
7401 TGCAGCCACA TCCATAATCC TGCCTCTGTT AGCCTTCCGA CAGACCCTCA
7451 GGTGCCCAGG ACAACAGGAA GCTACTTAAA GCTGGAACCT CAGACTGTGC
7501 AATGGAGGCC AGTGACAAAA CTGAAAGTAG CTCTGTCAGT AATTGTGCTG
7551 GTGCGATTAG GCAGCTGGCC AGAATCTTTT GGATCTCCTG GACATATGGC
7601 TGACTAGTCC TCCCAAGCCT TCCCAACAGG CCTCTTTTTT TTCCTTTTTT
7651 TCTTTTCTTT TTTTTCTTTC TTTCTTTCTT TCTTTTTTTT TTTTTTTTAG
7701 GCTAGTGAAG TGAAATTGTG GGAGTGGAAA AGGAACAAAG AAATCGGTAA
7751 CTGGTAGTGA TCAATTACTT GTAAACACTA TTGTACTTGG ACCAGCCCAG
7801 TAGGCCTTTT TTAAAACTCT GAGTTACCTC TCTTTCCTTT CCTTGAGCAG
7851 TGCCATTAAT TCTGTATCTG GGGCAATCCT TTCTGATGTT CTCTGGACCT
7901 GGCTCTCTCT CCTTAGGAGA GGCCAGGAGA GTAGCCAGAG AGCATGTCAT
7951 TTGTAGCTGA GGTTAAAGTG TGGAGCTATC AATGGTGACC TGGCCTCTTG
8001 GCATGTTAGC AAGCCAGAGG ACCTTGACAA CTTTTTTGAT GATTGTCCGT
8051 TCACCCTGAT CAAAGGTGTT TGGCTTAGGA GGAGGGAAGA AAAGCTACCC
8101 CTATTAGTCT TGATGGCCCC AGCGTGGGTC TCTATTGCTT GACCTGGTTC
8151 CTAGCAGCAT TATCAGAAGG AAAATCCACC GCTCTTAAGG CTCCTGGGAA
8201 CTTTCAGGAC TTCCTTTCTC AGGATTGCAA ACATAAGACT ATTTGAGCTT
8251 TCACTTTTGA AAAGCGGTTA CTAATACCTA TACTCTGGGA AAGGGCTAAT
8301 GCAGATAGAA GACTGTGGTC ACTGCATCAG GCAACAGACC ATTTCCGCTA
8351 AATTTAGTGA CTCCAGGAAG GCCAGTGAAG AAATAACACA CGTAGCAACC
8401 AGAGACTGTG TTGTAATATG TTGGCTGACA GCAGGGTACT TTCTGTGATG
8451 CTGAAAGCCA CATTCATTTT CTCTCCCCTC ATCCCCATCT AAGCAAGCCT
8501 GGTAGAATCA TAATTACAGT AATAGGTACC ACTTATTGAG TACTCTGTGC
8551 CAGACACCCT CCTGAGCATA CGACATGCAT AGCACATTTA ATCCTTACAA
8601 TGACTTAATA AAATGTAGTA CTAGTCTTAC CTACTTCGAG AATAGGGAAA
8651 TGGAGGTTAC TTGTTTAAAG TCACAGAGCT AATAGGTAGC ATAGCTGAGA
8701 TTTGAACTCA GGCATTCTTA CTCCTTGCCT GCAAGAGTCT CTTGGCATTC
8751 TTGAATGCAA GCATATTTCT TAACCTCACT GAGGCTCAGT TTCCTCTTAT
8801 ATAATATGGG GTAAAGAGCC CTCACCCTGC CTGCCACACA CTGGTAGTGT
```

FIGURE 3-3

```
 8851 CAGATAACAT TGAAGGGTGT TAGTTTAAAG GCTTCATGGA CTCTATAATG
 8901 TCAACAAAAG TGCTGTTAAC TTTCTTCTGG GTCTCAGGCT CCTGATGTAG
 8951 AGTCAGTGGA GCAACCCTGC CATCTGCTGT TATGCTGTTG ATGTTGCTGC
 9001 CACACTTACT AACCTAAACC TTTGATTCTG GCTGTGGCCT TCTCCAGAAG
 9051 GTGTTTACTC ATTTGTCCAG TTTATCTTTT AGGAAACAGC CAGCCCGTAG
 9101 ATCATTAAGG CTGGCTATTG GACAGGGGGC TGGGGCCTGC CTGACAGAGG
 9151 AAGGAAGGGC AGACATCTGG TTCTTCCTCT GCCCCTACAA GAGACTCCAG
 9201 CCTGACCACA GAGTGGTACT CCTAGGATGT AGCAGCAGCA TATGAGCTTG
 9251 AATGTGCCTT AATCCTGCTC TTTACTTTGA GAAGAGAGAA CTAAGGACCC
 9301 ACAGATGTTT CACAGCTTCT ATAGGAGGCA GAGGTAGAAA AATGGAGAGA
 9351 GATGAGGCCA GAGATAGATA ACTGATATTA ATTAAACGTT GTATTAAGAA
 9401 CCTCACTTAG ATTATCTGAT TCAATCTTCA TAATAACCCT GCAACCCCCA
 9451 CCTTTTTTTG AGAACAGGGT CTTGCTCTGT TGTCCAGGCT ACAGTGCACT
 9501 GGTACAATCA TAGTTCACTG CAGTGTCAAC CTCCTGAGCT CAAGCAATCC
 9551 TCCCACCTCA GCCTTGCAAG CAGCTTGGAC TACAGGCGTG CCACCACACC
 9601 TTGCCATTTT TTTTTATTTT AAGTAGAAAC AAGGTCTTAT TAATACTATG
 9651 TTGCCCAGGC TGGTCTTGAA CTCCAGCGAT CCTCCTGCCC CAGCCTCCCA
 9701 AAGTGCTTGG GATTACGGAA GTAAGCCACT GTGCCTGGCC AGTGCAACCC
 9751 CCATTTTATA CTAAAACAGG AAGGCCCAGA AAGGTTTGGA GTAACTTGTC
 9801 CAGGGTCACA CAGATGATAT TTGAACTCAG GTCTCCCTGG CTCCCAAGAG
 9851 AGTCTGCTTT CCACTAGGAC TCCAGGAGA AAAAAAAAAA AAAAAACAGT
 9901 AGACTTGGAG ACAGAAAATC TGATTTGAGT CTTAGTTGAG CTAGGCTAAC
 9951 TGTGTAACTG TGGGCAAGTT CCTTAGCCCC TGTGAGCCTC AGTTTCTTAT
10001 CTGTAAAATG TCATAAAAGA AATCCATCTC ATGGAGTAGT TGTGATGATC
10051 AAGGACTCTG AAAACATTAG AATGGTTTAA TGTGAAGGAT TAGCAGCAGC
10101 ACATGGCAAC ATTGTGCATC TTATATTAAC TATCCAAATA TATCAAGCGT
10151 CATTTGCTAT ATATAAAAGT CATCAAATTA GGCACTGTGG GGGATACGGA
10201 GTTGGCATAC TAGCCTGGCC TCTTAATTAA TTCATTAATT AGCTTATTTA
10251 TTTTTGAGAT AGGTCTTGCT CTATTGCCCA GGCTGGAGTG CAGTGGCATG
10301 ATGATAGCTT ACTATAGCCT CAATCTCCCA GGCTTAAACA ATCCTCCTGA
10351 GTAGCTGGGA CTACAGGCAC ACACTACCAT GCCCAGCTAA TTTTTTTTTA
10401 ATTTTTTGTA GAGACAGGGT CTTGCTCTGT TGCCCAGGCT GGTCTCAAAC
10451 TCCTGGGCTC GAGATCCTCC CACCTGGGCC TCACAAAGTG TTGGGATTAC
10501 AGGTATGAGC CACGGCACCT GGCCTGGTCT CTTAACTGGT TCCCTAAGAC
10551 AGCTGGAAAT AGAGAATGTC ATGGAGCATT CCTAACCATG GGCTCCAGCC
10601 TGGCTTTCAT TCTGTTTCTC CCCTGAAACA ACATTCCTTT AGTAATATTC
10651 CGAATAACAG CTTCATCAGT CTGTCTACCG ACCACTCTTC AGGCTTCATC
10701 TTATATGACC TCCCAAACTG CACTAAGGGT TGTATTAGAG AAAAGTGGAT
10751 AAAGTTCGGA GTCAGGCTGC TTGAGCTTAA ATGCCAGCTT CACTTACCAG
10801 CCACCTGACC ATGAGTCAGC TGCTTAACCA TTCTTTGCCA CAGTTTCCTT
10851 GTCTATGAAA AGGGAAATGG CTCCCACCTC AAAAAGTTGT TAACATTAAA
10901 TTCAATCATG TATTCAAAGT CCTGAGCAGA ATGTCTGCAGTC ATGACTGGGA
10951 CTTAACAGAT GTTAGCATTT ATTATTAGTA TCTGTCAGTC TTGAAATGTT
11001 CTCTTCCCTT GGCTTTCATG ACATTCCACA CTCTCCTGGT TTTCTCTTAC
11051 CTCTCTGGTA ATACCTGTTT GCTTATCCTT CTTTGTCCAG CTCTGGGATG
11101 TTACCATTCC TTCAGGCGTG CTGTTTTCTC CTTAGGCAGT CTTACACACA
11151 CTCATGACTT CCTTCCATTG TCCTCCACAC ACTGATGACC CTAAAATCAG
11201 TATCTCCAGC CTAAACCTTT CCACTGAGTT CTAGACCCAT ATGTTGTACT
11251 ATCAACCTGG CTTGTCCATT TGAATGTCTT CCAGGCACTT CAGACTCTCT
11301 TCTCTAGACT TTGCTGGACT TTCACTCTTC CCCTAAAAC TGGCTCCTCT
11351 TCCACTGAAA CATGTATGTC ATTGAGAGGC ACCACCATCC ACCCAGTGCC
11401 TAAGCCAGAA ACCTAGGAAT CCTTGATACC TGTTCTCTCT CATCCTGCAT
11451 ATCCAAGCCT ATCAGTTTTA TCTCTAAATT ATATTTTGGT AGGTTTACTT
11501 CTTTCCTTTT CTCCCACCAC CACCCTGCTC CAAGCTACCA TCATCTCACC
11551 TGGATGTCTG CAATAGCCTC ATCTCCCACA GCCACTCTGC ACCCCCTAAT
11601 CTGTTCTCTA TAGAGCAGTT GGAAGGAGTG ATTTTTGTTG TTTGTTTTGT
11651 TTTGTTTTAG ACAGAGTCTC ACTCTGTTCC CCAAGGCTGG AGTGCAGTGG
11701 CACAATTTCG GCTCACTGCA ACTTCTGCCT CCCGGGTTTA AGCAATTCTC
11751 CTGCCTCAGC CTCCCAAGTA GCTGGGATTA AGGCACCGGC CCCCATACCC
```

FIGURE 3-4

```
11801 AGCTAATTTT TATATTTTTA GTAGAGATGG GGTTTTGCCA TGTTGGCCAA
11851 GCTAGTCTCG AACTCCTGAC CTCAAGTGAT CCACCTGCCT CGGCCTCCCA
11901 AAGTGCTGGG ATTACAGGTG TGAGCCACTG CACCTGGCTG GAAGGAGTGA
11951 TCTTAAAAAA AAAAAAAACA AAAAAAACT TGACTGTGTC ACTCTGTGTT
12001 GTCTCTCCTA CCTTGTATAC TTCCACAACT TCCCAGTGTT CTTGGATAAA
12051 GACCAAAATC CTTAACTTGG CCAGGCGCGG TGGCTCACAC CTATCATCTC
12101 AGCACTTTGG GAGGCCGAGG CAGGCAGATC ATGAAGTCAA GAGATTGAGA
12151 CCATCCTGGC CAACATGGTG AAACCCCATC TCTACTAAAA ATACAAAAAT
12201 TAGCTGGTCG TGGTGGCGTG TGCCTGTAGT CCCAGCTACT TGGGAGGCTG
12251 AGGCAGGAGA ATCACTTGAA CCTGGGAGGC AGAGGTTGCA GTGAGCCCAG
12301 ATCACGCCAC TGCACTCCAG CCTGGTGACA GAGTAAGACT CCATCTCAAA
12351 AAAAAAAAAA AAAAAAAAAA TTCCTTAATT TGGCCTACAG TAGAGCCCTC
12401 CGTAATGTGG CCTCTCTCCA CATCTCCACA ACCTCCTGCT CCCTGCACTT
12451 CAGCCTCACC TCTCTTCTGG ACAGGCCCTC CTTCTGACAA GGGCTTTGTT
12501 CATTCTGCTC CCTCTGCCTA GAATGCCCCC TTACTCTGTT CACTTAACTC
12551 CTGCTTATCG TTTAGATCTT TACCTGGATG GCTCAGAGAA ATATAGAAGT
12601 AATTCCTCAC CCTGAAAAAT AGGTTAGGTC CCTGTTTTAT GTTTTCATAG
12651 ACCTTTCCTT TGAGGCTTTT TTTAAAAAAG TAGTTTTAAT CTCACATTTA
12701 TTCATGTGAT CATCTCCTTA ATGATATCTT AAGACCTCTA ATAGAACAAT
12751 TTGGTCATGG ACTGTGGGGT TTTTGCCCCT CATTGTGTCA GCACTGAGCA
12801 TATTGTTGGC ATAGGAGGGA TATTTGTTGA ATGAATTGCT AGAGGTGGCC
12851 AAGAGATATG ATGTAAGTCA GGCTTTTCCC TGCCCTTCCC CTTCCCCTTC
12901 CCCACATCCT TCCTATAGCA GCCACCGTGG CTGCAGTTAC TGTAAATGGC
12951 AAGACGGAAT CAGTTCCGGA CATTGGGTTG TTTTAGAAAA TTGCCTGCAA
13001 GTGTCAGGGT GATAAGTTAA AGCTTTGTCT TTTGCCCTCA GAGGAGCTAT
13051 CCCATAGTGA GTAGAAGCCA GAGAAGCTGA CCCCAGGAGT CCTTCTTTCC
13101 AGCAGCAGGT CTTGAGCTGC ACTTCTCTGT AGCTACAATC CAGGCAGGAA
13151 CAAGCCCTAG GTACCTCCGG AGAGGAGGGC AAGAGAGGAA GAATGAGTTC
13201 AGCTACTCTA GCCACCAAAC TGATTATGAA TTGCCCTGAA ATCTGAAAAA
13251 TTTCAATTCC AATCGTAAGT TTGTTTTGTT TCATTTTGTT TTCTTAAATT
13301 GTATATTTGA AAGATGGCAT TAACTAAAGA TATATATTCA ATATAGAGTG
13351 GAAAAAATGG AATACTTGCA TAGTATCTTT TACTTATAGG TGATTTATGA
13401 TGGGAGTGG GGTGGATAGG TTGGCAGTTC CCCCAAGAAG TTGGAAATGA
13451 AGTTTGTCCT CTGTGAGTTG AACTAATTAG ATCCACAAGT AATGAAAGCA
13501 GTATTGTGTT GTAGTTAAGA GCACACTCTA GAACCAGATT GCTTAGTTTC
13551 AAATCCTGGT TCTGCCTTTT ATTATCTGTG TACTTTGGGC AAGTTACTTG
13601 CCCTTTGTGT GCTTCATTTT TCTCATCTAG AAAATGGAGA GGCCAGGCGT
13651 AGTGGCTCAT GCCTATAATC CCAGCACTTT GGGAGGCCGA GGCGGGCAGA
13701 TCACCTGAGG TGAGAAGTTC AAGACCAGCC TGGCCAACAT GGTGAAACCC
13751 TGTCTCTACA AAAATACAAA AATTAGCCAG GCATGATGGC GGGTGCCTGT
13801 AATCCCAGCT ACCCAGGAGC CTGAGGCGGG AGAAACACTT GAACCTGGAA
13851 GGCAGAGGTT GTAGTGAGCC AGGATTGCAC CACTGCACTC CAGCCTGGGT
13901 GACAAGAGCT AGACTCAGTC TAAAAAAAAA AAAAAAAAAC AAACTGGAGA
13951 TACAGGCTGG GTGCAGGGCT TACACTTATA ATATCAGCAC TTTGGGAGGC
14001 CTAGGCGGGA GGATTGCTTG AACTCAGGAG TTTCAAGATC AGTCTGGGTA
14051 ACAGAGCAAG ACCTCATCCC CACAAAAAAT CAAAAATTTA GCCAGGCATG
14101 GTGGCTCATG CCTGTGGTCC CAGCTACTCA GGAGGCTGAG GCGAGAGGAT
14151 TGCTTGAGCC CAGGAGGTTG AGGCTGCAGT GAACCATGAC TGCACCACTA
14201 CATGCCAGCC TGGATGACAG AGCAAGACCC TATCTCAAAA AAAAAAAAAA
14251 AAAGAAACGA GCCAGGCGCG TTTGCTCACG CCAGTAATCC CAGCACTTTG
14301 GGAGGCCAAG GCAGGTGGAT CACTTGAGGT CAGGAGATCG AGACTAGCCT
14351 GGCCAACATG GTGAAACCCC ATCTCAACTG AAAATACAAA AATTAGCCAG
14401 GCATGGTGGC ATGCTCCTGT AGTCCCAGCT ACTCACTTGG AGGCTGAGGC
14451 ACGAGAATCG CTTGAACCCA GGAGGCGGAG GTTGCAGTGG GCCAACATCA
14501 TGTCACTGCA CTCCAGCCTG GGAGACAGAG CGAGACTCTG TCTCAATAAA
14551 TAAATAAACA TAAAATAAAA TAAAATAAAA TAAAATAAAA TAAAAAAATA
14601 TGGAGGCCAG CAGGCACGGT GGCTCACGCA TGTAATCCCA GCACTTTGGG
14651 AGGCCGAGGG GGGCGGATCA CAAGGTCAGG AGATCGAGAC CATCCTGGCT
14701 AACACAGTGA AACCGCGTCT CTACTAAAAA TACACAAAAT TAGCCAGGCA
```

FIGURE 3-5

```
14751 TGGTGGCAGG CACCTGTAGT CCCTGCTACT CAGGAGGCTG AGGCAGGAGA
14801 ATGGCGTGAA CCCGGGAGGC GGAGCTTGCA GTGAGCTGAG ATCGCGCCAC
14851 TGCAGTCCAG CCTGGGCGAC AGAGCAAGAC TCTGTCTCAA AAAAAAAAAA
14901 AAAAATGGAG GTTGGGCGCG GTGGCTCGCG CCTGTAATCC CAGCACTTTG
14951 GGAGGTCGAG GCGGGCGGAT CACCTGAGGT CAGGAGTTCC AGACCAGCCT
15001 GGCCAACATG GTGAAACCTT GTCTCTACTA AAATTACAAA AATTAGCCAG
15051 GCACGATGGC AGGCACCTGT AATCCCAGCT ACTTAGGAGA CTAAGGCAGG
15101 AGAATAGCTT GAACCTGGGA GATGGAGGTT GCAGTGTGCT GAGATCGCGC
15151 CACTGCCCTC CAGTAGAGTG AGATTCCGTC TCAAAAAAAA AAAAAAAGAA
15201 GAAATGGAGA TACAAACTTA CTACCTACCT CCTTACAACC TACCCTCACA
15251 GTATTACTGT GAATAAAAGT GTGTGTAGCA CTGGAACAC TATTCACAGA
15301 GCACTCATGA ATGTTTGTTC TTTGTTATTA GTTACTAGAG AGGCAAATGT
15351 CTGCCAGGGC TGAATAATAT GTGTGAATTG GTGATTGTCG CACATATCTA
15401 AAGAAGTAGT TATTTTTTTC AATTAAAACT TAGTTTAAAA ACCAATATAA
15451 GGCCGAGCGC AGTGGCTCAC ACCTGTAATC CCAGCACTTT GGGAGGCCGA
15501 GGTGGGCAGA TCATTTGAGG TCAGGAGTTC GAGACTAGCC TGGCCAACAT
15551 GGTGAAACCC TGTCTCTGCT AAAAAAAAAA AAAAAGTACA AAAATTAGCC
15601 AGGCATGATG GCAGGTCCCT GTAATCCCAG CTACTTGGGA GGCCGAGGCA
15651 GGAGAATTGC TTGAACCCAG GAGGTGGAGG TTGTAGTGAG CCGAGTTTGT
15701 GCCACTGCAC TTCAGCCTGG GTGACAGAGG GAGACACTGT CTCAAAAAAA
15751 AAAAAAAAAA ACCAAAACCA ATATAATAAA TAAGTGGCCA GCAATGAAAC
15801 AGAAAGTGAA AAGTTAGTGA AGCAAAACTA GTACTGTATT CAGATAAAGA
15851 TGCTGAATCT AGATTTGGTC ACCAGAATAG GGTCCTTTGT GGCAACCTGG
15901 GCTAGTTTGG CTGACTCACC ACTGCCAGGA TGAAATTTCT TTCAGTGGCT
15951 ACTCATTTCC CTTTATTTTA AGTCCATGCT CACAGAGCAA CCTTCTGATG
16001 CCTAATTCAG CTTCCTGGGA TACTTAATAA CAGGAAGGGT CTGGAAGTAG
16051 TACCTGTATA GGGGATATGA GTGTTCTGAT TTTAATAGTC AATTCATAAG
16101 TGTACAGAGG GTTTGATAAA TGGTTAGGTC AGAACCATCA CAGAATGTCT
16151 ACACCTCTTT GGACATTAGG AAGGTCAAAA ACCTGAAAGG CCAAAAGCTA
16201 GGCCTAGATT AGGGTCATTC ACCAAGAAAA CATCAGCCTT GAAGAGTTCT
16251 CTGGGTGGTC CACCAGTCAA CCTTCCTTTG ATCACACCTC CTTCCTCGTT
16301 GCTTCTTTAA GCATTGACCT GTAATGGGTA TGGAATTTTT TGCTCACCTA
16351 ACTCCTTCCT TTTACAGAGG AAGAAGTTGA AGCCCAGAGA GATTTAATGG
16401 CTTGCCTAAG ATCACACGCA GATTTTCTGT TAACCAGGGT GATTTTTCAG
16451 GTGTTCCCTG CCAGACGAGG GCTTTTTTCC TTGAATTGCC TAGAGATTTC
16501 TTGAGATATC CGAAGCATTT TTCCCAGTGC AGCCTGGAGA AGGATGTCCC
16551 TGTCAACACA GCATTTGTTA CTCAATGTTA GACATTCAAT TTTCTAATTA
16601 GTATCATGGA GCAACAGTGG ATGATTATCT ATAAGGGGTT GCAATTCCAT
16651 GCTTATGTGC TTACAGCCCA TATAGACAAA TATCAGCTGT TAAAATGACA
16701 AGGCAGTAGA GATGTGGCCC CAGGACAAAG GCATACTCTG CTGTTAGTGA
16751 ACACTAGTTG GCCAGCAAAT TTCACATGGG CATATACACG GCCAACTGTA
16801 GACTTTAGGC ATTTATACCC ATTCAGAGAG CCAAACTGGC AACTAAAGAT
16851 CAGCATTCTC TTTGGCATTT CAGCTTTGCG TTCTGTTAAA AATCACTGCT
16901 TGCTTAAATA CCTCTGATAG CTCTTCACTG CCTGTAGGCA ACTCTTTAGC
16951 CTAGCAGACT TGGTCTTTAG TGCTCTGCCC CTACTCTCTT CCACCATTCT
17001 GGCCTCCTGT CTAATTGCTG CCCATATGTG CCATGCACTA GAGCTTACAG
17051 ACCTGCTCAG CGTTATATGA GCATACCATA CTCTTTATGC CTCAGTGCAT
17101 TTGCACATGT TGTTCCTTCA GGCCAGAATG CCTGTTACTG CCTGGCAATC
17151 AGCCTATTAG AGTCTGCCAA TACCATCCCA TCTTCTGTGG AGGAGCCCCC
17201 CGCCAAATCC ACCCATACCT CTCCCCACCA ATCAGAGACT TCTTCTCTCT
17251 TTGTTATTCT CTTCGTTATT CTCTTCATAC CTCAGTTATA TCCATTTCAG
17301 TATTTGTTTA CACATCTAGC ATCACTCTTA GAGTGTGAAA TTCTCCAAGT
17351 GTGGAGCCGT ATCTAGTTTG TCTTTGTATC CCAGAGCTTA GCAAAGTGCC
17401 TAGAATGTAG TGGGTGCTCA GAGTGTTTGC TGGGTGAATG ATGTATTTGT
17451 TGAACGACTC TTTGGACACT TGAATAAAGT CCATCCAGTA TGCACCATTA
17501 CCATCTCTTC GCTCTACAAT ATTCTTTTAG GCAAGAGCTT ATCTTTTGAG
17551 GTGATAAGAT AAGCTCAAAC TTATGTAGAC TAAGACCTCA GTCTGTAAAT
17601 GTCATCCCTA AGTCTTAAAC CATCAAAACC AGGGCCTCAA GGAATGGCAT
17651 GCCTTCTGCA ACTGTAGCAA CCTGCTGTGC TTATTTTGCC GTGTTTTTCA
```

FIGURE 3-6

```
17701 TTTTTCCCCC AAAAGCTAGA GTCCCTTCTC CCATGGGCAG TGCTGGAAGT
17751 GTGCTAACAA ATTCTTTCTC CATACTGCTT ACGATTACAA AAAAAACCCT
17801 CAGCATCTCA TGCCAGACTT GAGTTAAGGT TGTTTTCTTT TGTGTGTCAG
17851 CTGTATTCTG GTCATGACTT CCTGATGATG CCCTATAGAG ATTTTGCTGA
17901 GATCAGAGGG TGCTCCACTG CCATCAGTAG CACTGACTCT TGCAGAAGCA
17951 CCGTTTCTGA AGTTGGCTAA TGTCATCCCT CACGTTTGTT TGTTTGAAAT
18001 TTGTTTTAGT TCCAGAGATA GCACTTTCAT GGAATGACGC TATCTTCTAG
18051 AATCACTTTT TTTTTTTTTT TGAGTTGGAG TCTCGCTGTG TCGCCAGGCT
18101 GGAGTGCAGT GGCACAATCT CAGCTCACTG CAATCTCCAC CTTCCGGGTT
18151 CAAGTGATTC CCCTGCCTCA GCCTCCCGAG GAGCTGTTAC TACAGGCGCA
18201 CACCCCCACT CCTGGCTAAT TTTATGTGTT TTAGTAGAGA CGGGGTTTCA
18251 CCGTGTTGGC CAGGATGGTC TCGATCTCCT GACTTTGTGA TCTGCCTGCT
18301 TCAGCCTCCC AAAGTGCTGG GATTACAGGT GTGAGTCACC GCGCCTGGCC
18351 TAGAATCACC TTTTTATACC ATAACGTGAG CACCACTGCC GCGTCACCAA
18401 GGAAAGAGAG AGGCAGCTAC TGTGGGGTTA CAAATGGGTA AGAGTGGCAC
18451 CAGGAAGGTG AAAGTCTCTA CTTAGCCAAG GCTTAACAAA ATGTCAATCA
18501 CCAAACATTT ATTTATTAAG CTACGTTCAG GATAAGAAGA TGAACAAGCT
18551 ATCTGTACAT TCATTTTCTC GTTTGTAACA AGGTAATGAT AGTGATCTAT
18601 CCTGCCTGCC TCTGAGGGTT ATTGTGAGAA TAAAATGAAA TCAAGTGGAA
18651 AAGCACTTAG GAAAAAGAAA AGCATTGGTT TTCAATTGTT AGTGTGGATC
18701 AGAAACACTG GGGCTTGTTT AAAATGCAGA TTCTTAGCCC CAGTCTCAGC
18751 GATTCTGATT CTGTATATCT GAAGTGGGAC TCAGGAATCT TGATTTTCAA
18801 CAAGCTGACC AGAGGGTCCA ATGCTGCTAT TCCTTTAGTT ACACTTTCAG
18851 AAATATTACT GTAAATCAAA TGGCAAGAAT AAAATAGTTA TTTGAGGCAG
18901 TTTTAGTATG TTGGACCTGG AGTCCAAAGA CTTGGGTCAA ACTCCAGCTT
18951 TGTCAGTTCC TAGACCTGTG ACCTTAAACA GCAACCTTCT CTGTGAACCT
19001 TAGTTCCCTC AGGAACGGCT CTGGTCACCT CCTGCTGTAC TCCATTGATG
19051 ACTCACCACA TAAGGCTCCC TGGGAGTCCC CCAAACCTTT GCTCTCTTAA
19101 CTCCTTTTAC AGCCTCCTAC ATCTCCTGCA GGTGCTGTCT TCTCCTCCTT
19151 TTTCCAGGCC CTGCTCTGAC ACAGCATTCA TTCTCCTCTG GAAGGGTTC
19201 CTTCAATGTG TCTCCAAGCA CATCACACCC AGGAAGGACC CTGTGGCCAT
19251 ATCTGTCTAT CACCAGATCA AACTACGTGA AGGCAGGCAC TAGGTACTGT
19301 CAGTGCCCAG CATAGGCCTG GCCCATACCA GGTGTCCACA GATGCCTAGT
19351 AAAGAAACCT ATGATTCAGG ACCCCCATGA TGAGCAACTA TAGCACTAGA
19401 ACAGTGATAA TAACTAATGT TTATAATGCA TCTTCAGTTT ACAGAGGGCT
19451 TTTGTACTCA TCATCTAGTT TAGTTCCTGC AACAACCTCT TGAGGAATAT
19501 AGCACAAGCA GGACAAGGGA AGCCCAGAGA TGTTAAATAA TTTATCCAAG
19551 TTTATGCTGC TGGGAAGGGC AGCACTGAAA TTAAAAGAAA AGTTTTCTGA
19601 GCTCAAATCC CATGCCCTTT CCTCAATGTG AGCTCTAGCA AGGTATTCAG
19651 GAATCCTGCC TCTACAGTTC AGAGCCTCAA ATTGCTGGGT ATGTTGAGTT
19701 CTTGTATCTG ATTTTTTCTAG ATTTCCTGCC CACATTCTTA CTGTCTGGAT
19751 ATCAGGAAAG AGTTTATCAA ATGCCTGTGG AAATCCAAGA TAAGGTCTCA
19801 TGATGAGTAA CCCAGTGAAA ACATGAAGTC AAGTCTAACT AGTCACTACT
19851 ATTTCACTAC TGCTGACTCC TGATGATCAG CTCCTTTTCT AAGTGCTTAC
19901 TGTCCACTTA TTCCATCATC TGCCTAGAAT TTATGTGAAG GAATCAAAGC
19951 AAAAGGATCA TAAGGCTTCC TTTTTCCAGT ATGTTTTTCC TCCTTTTTGA
20001 AAACTGGGCC AGTTAGCTAT CTCCATTTTT ATTTCATGAA TACATCCCCA
20051 GCGCCTGGTA TATAGTAGAT ATGGAACATT ACACTTTGGA GATATTGCAC
20101 CCATTCTCCA GTTTCTCCAA AGTTACTAAC AATGGTTCCA TCACTGTGCC
20151 AACATATTTT CTTTTTTCAA TATATTGGGA AATAATTCTC CCAGTCTGAA
20201 AATCTGAACA CATTTCATGT GACTTGGTAT CCTCATATGT CTTGGGCTTC
20251 CAATTCTCCA TTCCTAGTTT CAAGTTCATG AACTGTAAAA CAAAGGATTA
20301 GACTAAATCT CTAAAGTTCT ATCCAGATGC CAAATTCTTT TCTCTTTCCA
20351 TGATACCTAA GATAGATGCC AAATATTGTC TTTTACCTGG TGTTTGTGAA
20401 CATGACATCA CATTACAGGA GTAGCAGATA CTAAACTCTC ACTCTGTAAA
20451 ACACTGACTG AGTTCCATGA GCCAGATACT GAAGTGAGCT TGTTCACATA
20501 TGTTCTCATT TAATGCTCAT AACCCTGTGA AGCTGGGAAT TGCTGGGACA
20551 TTTTATTTAT TTATTTATTG AGACGGAGTC TGGCTCTGTC ACCTAGGCTG
20601 GTGTGCAATG GCATGATCTT GGCTCACCGC AACCTCCGCC TCCCGGGTTC
```

FIGURE 3-7

```
20651 AAGCGATTCT CTTGCCTCAG CCTCCGCAGT AGCTGGGATT ACGGGGCACA
20701 CACCACCACA TCCAGCTAAT TTTGTATTTT TAGCAGAGAT GGAGTTTCTC
20751 CATGTTGGCC AGGTTGGTCA CGAACACTTG ACCTCAAGTG ATCTGCCTGC
20801 CTCAGCCTCC CAAAGTGCTG GGATTACAGG CATGAGCCAC CATGCCTGCC
20851 CGGGACCCTT GTTTTAGAAG GATGACTGCT GCTATAATGT AGAAAGTGAT
20901 TTGGAAGAGG GGAGGAGTGG GGCACGAAAG ATGGTTAGTA GATGGGGGTG
20951 GTAATGCTTA CCTTTCAGTA TTTGGAGGCT TCGGAGTCCT CAAAAATTCT
21001 CTTCCTTGAT TGGAGTCCTC CCAGCCAATA GAGGGCTTCA CACAAACAGT
21051 TTCTTGGGTT TTGAATTGTT TGACCAGAGC TTTCTTCCGA CAAAAGGTTG
21101 GGGTGATTCA TTCACTTACC ACACCTTGCC TGAACATTCA CTTGGGGCTG
21151 CCGGTTATGA AGGCTATTGT TCTCCAGCCT GTCACAGACG CTTTGAAGAC
21201 CTGTGCCTCA GCTGGTTCTA AGGAGTCAGT TTGTTCAGCT CCGTGCCAGG
21251 TTTCCAACTT ATGAAATGTG CTGGAGATTA ACACCTCTCC TGCCATTTTA
21301 TCCCTACTAT AATTGCCAGT CAAAGGATTC CTGCAGTTGC CTCTGGCAGC
21351 CATAACTGAT GAATGTTCTG CCAGCTGCTC TGAGGACCTA GAAGAGCAGT
21401 TTTCTATCCA GGACCAGTTT CCAAGGGTGG GAGGGTGAAA TATATCCTCC
21451 AGTGTGACAT TTCATCTCCC AGTGATGGGT GGCTTGGGCC CTTTGAAGTT
21501 GGCTCTGAGG AACCACACAC TTGGGTCTGA GCAGCCAGCA GCTTATCACA
21551 TCTGGTGATC AATCCTTCAA AGGTTCCTCC TGAAGTCTGA ATTTTTGGAG
21601 GTCAAATGGA TTCCACCTGG GAGGGGCTTC TGCTTCAACT CAGGACATGG
21651 GGAGAAGGCT GTTCCTCTTC CAGGGGGAGG CAGTTTTCAT GGCATTGAGA
21701 TGTCCTCTCA CTTATTCCCC ACCCACCCAC CAAGTCCTTT GTAAGAGGAG
21751 TAGGGGGAGA GGAGAGCGCC TGCAGCCTCC TGCTCACATT CCTAGACACC
21801 GACTCACTGA GCCGGTCGCC GCTGGAACAG CAGAGCTGTG TGAAATGTCA
21851 AGAGGAGTTA TGCTCATAGG CTCCCTGGCC TCAGTCTCTT TGTGGCTTGC
21901 ATATTCTTCC ATTAGTACTG TGTTCATCAC ATGGAAATCA GAGGGTACAA
21951 TTAAAAGATA ATTTGCTAGT CCCAGACTTA ATTTGGGGCC CCCTTCTTGC
22001 CTGATTGAAT TACAGGGGAA CATAATAGAT TTTTGGTGAG AAATAGTTGT
22051 CTGTGTGGCT GGGAGAAAGA TTGCTCCCAG CTCTCCAGCT GGGCAGCCCT
22101 TTCAGTATCC CGTATGTTAT TTCCCCACTT CCAGCCCACC TCACCTCCTC
22151 TGTGGCCCTT GTGTGTCCCC TCGGCTAGGA TCCTGACCTC CTGCTCAAGA
22201 GTTTAAACTC AACTTGAGAC CCAAGGAAAA TAGAGAGCCC TCTGCAACCT
22251 CATAGGGGTG AAAAATGTTG ATGCTGGGAG CTATTTAGAG ACCTAACCAA
22301 GGCCCAGACA GAGAGAGTGA CTTGCTAAAG GCCACATAGC TAGCCCACAG
22351 TAGTTGTAAC AATAGTCTTA ATGATATTAA TGGCTAACAT TTATCAACCT
22401 TTAATGTGTC CCAGACTTTG TGCCAAGGGC TTACATGCAG TGCATTGTCG
22451 CATTCAAACC CAGACAGTCT GGCTCTGGGC CCAGGCTGAG CTTTGGTATA
22501 GCATGGTAGA ACGTTGTCTA TAATGTCTAG TCTGGGTTCA AATCCTGGCT
22551 TCACTTCTCA CATTTACAGC TGAGTGACCT CAGGCAAGTG ATTTAACCTC
22601 CCTGTACCTC AGTTGCTTTA TCTGTAAAGA GAAAAATCAC AGCACTGTGG
22651 AATAGTGGGG GTTAAAATTC ATTCATACAA GTAGTGCTGC AAGCAATGTT
22701 TAATACAGGG TGAGCACCTG TTCAGTGCTT CCTTCTTCTG GCTGCCTCTG
22751 GGGCTAGAGT GTGGTGTCTT CGTGGTATAG ATAGATAGAT ATGGCTGAGC
22801 TCTGCACAAA CACCAAGAGC TGTTCTTCAC TATTAGAGGT AGTAAACAGA
22851 GTGGTTGAGC TCTGTGGTTC TAGAACAGAG GCCGGCAAGC TATGGCCCAT
22901 TGCCTATTTT AATACGGCCT GTGATTGATT GATTTTTTTT TTCTTTTTGA
22951 GACAGAGTTT CACTCTTGTT GCCCAGGCTG GAATGCAATG GCACGAACTC
23001 AGCTCACCGC AACCTCTGCC TCCTGGGTTC AAGCGATTCT CCTGTCTCAG
23051 CCTCTCGAGT AGCTGGGATT ACAGGCATGT GCCACCACGC CTGGCTAATT
23101 TTTGTATTTT TAGTAGAGAC AGGGTTTCTC CATGTTGGTC AGGCTAGTCT
23151 CGAACTTCCA ACCTCAGGTG ATCTGCCCGC CTCAGCCTTC CAAAGTGCTG
23201 GGATTACAGG CGTGAGCCAC CATGACTGGC CTGATTGACT GATTTTTTTA
23251 GTAGAGATAG GGTCTTGGTT TGTTACCCAG GCTGGTCTCA AACTTCTGGC
23301 TTCAAGCAGT CCTCCCTCCT TGGCCTCTCG AATGCTGGGA TTATAGGCAT
23351 GAGCCACTAT GCCTGGCCTA TATGACCTGT GATTTTTAAT GGTTAGGGGA
23401 AAAAAAGCAA AAGAATGCTT TGTGACATGT GGAAATTACA TGAAACTCAA
23451 ATATCAGTGT CCCAGCCTGG GCAACAAAGT GAGACCCTGT CTCTACAAAA
23501 AATAAAAAAA AATAAGCCAG GGCCGGGCGC AGTGGCTCAC ACCTATAATC
23551 TCAGCACTTT GGGAGGCCGA GGCAAGTGGA TCACCTGAGG TCAGGAGTTC
```

FIGURE 3-8

```
23601 AAGACCAGCC TGACCAATAT GGTGAAACCC TGTCTGTACT AAAAACACAA
23651 AAATTAGCCG AGCATGGTGG CATGCGCCTG TAGTCCCAGC TACTTGGGAG
23701 GCTGAGACAA GAGAATTGCT TGAACCTGGG AGGCGGAGGT TGCAGTGAGC
23751 CAAGATCGCG ACACTACACT GCAGCCTGGG CAACAGAGCG AGACTCCGAC
23801 ACACGCACGC ACGCACACAC ACACACACAC ACACACACAC ACGCTGGGTA
23851 TGGTGGCCAG CACGTGTGGT CCCAGGATGC ACTGGAGGCT TAGGTAGGAG
23901 GATCACTTGA GCTTAGGTGG TTGAGACTAC AATGAACCAT GTTTATACCA
23951 CTGCACTTTA GCCAGGGCAA CAGTGTGAGA CTGAATCTCA AAAGAAAAAA
24001 AAAAAAAAGA AAAAAATCTT TCCATAAGTA AATATCTGTT GGAACATAGC
24051 CATGTCCCTT AGTTTATGTT TTATATATGG CTGCTTTTGC CCTATAATGA
24101 CACAATTGAG TGGCCACGAC AGTCTGTATG GCCTGCAGAG CCTAAGATAT
24151 TTGCTCTCTG GCCCTTTACA GAAAAAGTGC CTTGACCTGT GCTCTAGAGC
24201 CATATGTACC AGGTTTGAAA CTCAGCCTCA CAGCTGGGTG TGATGGCACG
24251 CATCTGTAGT CCCAGCTACT CTGGAGGCTG AGGTGAGAGG ATCACTTGAG
24301 TCCAGAAGGT CGAGGTCAAG ATTGTAGTGA GCCATGATGG CATCACCGCA
24351 CTCCAGCCTG AGTGACAGAG AGAGACCCTG ACTCAAAAAA AAAAAAACAA
24401 AAAAAAAAAA CACCCTCACC ACTTATCAGC TATTTGTCTT GAGAATAGTG
24451 ACATAACCCC TCAGAACCTA TTTCCTAATC TGTTAAATGA GGCTGATGAC
24501 GTTTCCTCCT TTTACTGGCA ATTTAAACAT GATGGATAAT AAATGCTAAG
24551 CACTTAACAC AGGGCCTAGA AGATATTAAC TGCTCAATAA ATGGTAGCTT
24601 CTTAACAGTA TTCAAACCCA TGTGCTCTTA TCACATGCAT TGTTGTCCCT
24651 GTGTCCAGTT GGTGGAATGG GAAAAGGCTC CCTTGTAACC CCATCTACCA
24701 TCTTTATCAG ACTTTCCTGC CATGGTTCAC AGTAAGAGAT AGAAGCTGCA
24751 CGGTGACTTC TGGCTCTTTA CAATGGTGAG CGGTGTGTGC CTGGTAAGGG
24801 AGAGCTGATG TCACTGCCCC AAATCCAGTA GTGAGATCTG AGTGTTCTGG
24851 TTTCCTCCAG CAGCCTTGCT TTTTCCTTTA CAATCCTGCA GGCAGGGAGA
24901 CAAGGGCTTT CTACATGGTA GGCTCTGGTT TGGTCATCGT CACAACTGGG
24951 GGCTGTTCAG GTGGGCTCCC ATTCCAGATA CCTAGGCTTA TCAATCCCTT
25001 TTGGCACCCC AGGCCTTTTT CTCCCTCATG CCCCATTTTT CAGTTTGAAA
25051 AGCATGGTTA TCACAGGACA AGTAGAAGAA GCTCCACTGT CCACTGAGGC
25101 CAATGGATGG TGTTCTGCAT GTGAACACTC AGTGAATAGT GAGTGAATGA
25151 GAGTAACCTG GGCTCCATCC TATTTGCAGA GAGCTTTGGA AAAGATTTTT
25201 CTCCTTAAAG AGCCAGAATG AAGCCTGGTA GTGGGAGAGC TCCAGCTCTA
25251 GAGTCACATG AGCCTACATT TAAATTCCAG CCCTGCCACT GACTCCCTTT
25301 TTGACCTTGA GTGAGTTACC TAATCTCTCT GTACCTCACT TTTCTTGTCT
25351 GTAGAGTGGG AATAATTCCT GTCTCAGAGA AATAAAAGAG TGCATATAGT
25401 GTTTGCCACA TGGAGACACA TCAGGTGTAG GTTAATACTC TGGGCCTTGT
25451 TTCCTTATTT GCAACACAGC CCTGCCCTGG AGTGGAAGTG GCACCTCCCA
25501 TTGGTCAGCT CTTGAGGCTG TCCCCAGGAC AGGCAGAGGG AGGGAATGAA
25551 TGGGAGCCCT AGTGCCAGGA CAGAACAGAT GGCAGCTCAG AGCTAGGATG
25601 GCTCTCTGGA CCTGTCTCTC CTACCAGAGG TCCCCCCGTC TGGTGTGGCT
25651 CTTCCTGGAC CTGGCATCCT CTGCTTTTTT TTTTTTTCCA CCTCCAAGCA
25701 GAATTACTGT CCTGTAGGCA GCTCCTCTGC TTGAGGACAT CTGGGGCCAG
25751 ATATGTTCAC ACTCTATCCT GCCTTGCCCT TCCCTGAGCT CAGGATGGAC
25801 GCTCAATTGG TCCAGTTAT TGTCTGCAGC GCCTGCCTGC AGCCTCGATC
25851 CAGCCCAGCT CCACCCCTTG CCTGCAAGGT CTGTTTCCTA ACAGCTGCTC
25901 CAACCACACA CCTCGGTTCT GCGGGAGCCC CTCCTCTTCC TCCCTCCCTC
25951 CCTCATTCAG GGGTGGGACT GAAGAAGAAG GCTAACTTGA CAGCAGCGCT
26001 TCTTTCTTAG CTAGTCACCG GCCCTGCTC AAGAATGCCA GTGTGTGTGT
26051 AGCCTCCACA GAGAGGTCGT TTTCTCGGAG TCCAGAGGGG CCGCCTGAGC
26101 TTCTGAGAAC TAGGGAGGAG CCATCCCAGC CATGAGCCCC TGTGGGAATC
26151 TGCTGGGGGC CAAGTGGCCT GGAGTCCTCA GGCTCCCGCA GCTGCTCCGG
26201 AGGGAGAGGT GAGCTCAGGG CAGCCTGCCT GCAGCCAGAG GTGCCGGGAG
26251 CCCCGGGCCT GTCATGGTGG CCATCTACAG CCGGCCTGAG GCAGTCACAG
26301 ACGGATTTGC AGCTGAGCCT GTCTATCTGG TGTGGGAAGA AGATGGGGAG
26351 TTACTTGTCA GTCCCGGCTT ACTTCACCTC CAGAGACCTG TTTCGGTGAG
26401 TTGGTCTCCG AGTTCCCCTC TCCATCTCTC CTGGCCCCTG GTCCTGAGAG
26451 GAGGGTGGTC TCCCTAAATC TCCTTCTCAC TTAGTCCTTT ACCATCGGTT
26501 CTGCCGGGCA GAAGCCAGCG GAGGTTATAC CCAAGGAGAA TCGGCCTTGT
```

FIGURE 3-9

```
26551 GAGGTACCCC CATTATGTCC TGGAAGTGGT GAGGGGAGGG ATATACCCAG
26601 AAGGAACTTC TTAGGGAGCT CCAGCTCCCC TTCTATCCCA GACAAACCTG
26651 AAGGAGCCTC CAAAAGATGC CACTGACCTG CCCATTGTAG ATGTTACTGC
26701 TTCCGGGGGG AATAGCCCAA ATAGAGTGCT GTTTCCAGCT CTCACATGTC
26751 TTACCTGCGG GCCATGCTGC CTGCCCAGGA ATTTGTCCCA ACAAGCAGGA
26801 TGGGCAGGTT TTGCCAAACT GTGGAAACTG GCAAGTCCTG GGTGTGGGTA
26851 GCCTGGTACA CAGTAGGCAC CTTATAAACG TTTGTTCTCT TAATGGCAGG
26901 CACATTTGCC TCTGGCCTTG AAGGGCTTCT GAGCTCCCAG GTGAATGTAG
26951 TTGCTGGGGA AAGACCTGGG CGAGTGCTTC TAAGACTGGA GCAATGGGCT
27001 TTAGAGTGTT CCTGAGCTGC TGGGCCAGCC CCCACACCTC CTCAGTCCCT
27051 AGGCCTAAGT ACCTCCACGA GCCTCTCTCT GTGGGGCTTC TCAGAGGGAG
27101 ATGTGGAAAC TCTACCTCTA ACCTGGCTTT CTTTGCTCAT TGCCCCACTC
27151 CACCTCCCAT AGAAACTCCC CAGGGGGTTT CTGGCCCTCT GGGTCCCTTC
27201 TGAATGGAGC CATTCCAGGC TAGGGTGGGG TTTGTTTTCA TTCTTTGGGA
27251 GCAGCCTGTT GTTCCAAAAA GGCTGCCTCC CCCTCACCAG TGGTCCTGGT
27301 CGACTTTTCC CTTCTGGCTT CTCTAAGCTA GGTCCAGTGC CCAGATCTTG
27351 CTGCCGGGAT ACTAGTCAGG TGGCCAGGCC CTGGGCAGAA AAGCAGTGTA
27401 CCATGTGGTT TTGTGGAATG ACCGGACCCT GGTAGATTGC TGGGAAGTGT
27451 CTGGACAGGG GGAAGGGGGA AGGGAACTGG TCCTCAATGC TGACTCTACC
27501 AAGCGCCCTG CTAGACACTT TATCCTTTAA TCTCTCAACA GCCTAAAGAG
27551 ATTATATATC CCCATTTTAC AGATGAGGCA ACCAGTTTCA ACAGAGTTAA
27601 CATATGGAGC CTCACTGGGC AGCTTTTTCT GTCTTCCTGA CTTTCTCTCA
27651 TCCTTCAGGG GGCTGCAGGT TTGTTTTCTT CTCCTAGTGG AGAGGAAATT
27701 CTCAGGTTTG TTTTCCTCTC CTAGCAGAGA GTAAAAAAAG GGATAGTTTG
27751 CCTGACTTGT TGAAGGTGTG GCTGAGATTG TTTTCTAAAG AGCCAATGGA
27801 AATTGATCTT GAGTTTAGGA GAAAGCTTTT ACATGTGGAA TTAAGATGCC
27851 AAGTGTTGAA GTAGCCACAT TTCAGGTCCT CATTAATTTC TCTTAATCCT
27901 GGGAAGGCAG CTTAGGAGAA GGGTTGTTCC TTTAGGAGCC AGGAACTATA
27951 CCCCTTTTAC CCTTGGAGAG GCAGGGAAGC CAGGGAGGAC ACAACTTCTC
28001 AGGAAGAGGA GAAGCTAGAG CAGATAGTGA ACTCTCAACC TGAACCTTTA
28051 AGGGCCAGAC CACTAATGCC ACCCAAGTCC ACCTGCCGTT TGTCTTGTTC
28101 TGTCCCAGGC TTTCTGGAGA ACCTGATCTT CTTGCCCCTA CCCCCAAGCT
28151 CCGTTTGCCC AGCTAGAGTC TGGGGGGTAC TGACTGACTT TCGTAGACAT
28201 TCTTCCCTTC CCCAAATAAG AGGCCACATT CCTGAAGTCA CTTCTGAAGA
28251 GATAGCTGCC ACACAGGGCT CTTTCCCCCC AGGGAGGGAC CACCCAGACC
28301 CTCTGCTCTC CCAGGTATCC GTTACCACAT CACTACCTGG TCAGAAAGCT
28351 GTTTCTGCCA TTAGCCCCTC CCTCTTTTAT TATAGGATAT CCTCAAGGGC
28401 TCCTCTTTGG GCCTCAGTTT CATCCTTGGC AGAAAGTAGA AGCTAGACTT
28451 CTTGGGCTCC TGAACAGGGT CCTTGCTGGA TTCTGTGAAA CAAATTAAGT
28501 TCTTGACCCT AGGCCTCTGG GGGAGTACAA AGTCTATGGG AGTTCTGGGG
28551 CTGTGGTTGC AAGGAAAGTG ACGCAACCAG ATTCCATGGG GACATGATCA
28601 GGCGTGACAT GTGAGGGAGG AAGAGGGAGC AAGGGAATGA AGAATACAAC
28651 TTCTGTGTCC CATACACCCC TGCCTGACAG GCCATACATA CTCAGCAGAG
28701 AATGCACTGT CTTTCCTACC ACACTAGCGT GAGGAGTGAG CTGCAATTAC
28751 CACTGTGCTT CCAAGTAAGA AAATACCTCA AATTGGAATT TACAAAAGAG
28801 GTAAATTAGG GAGTGGCTTT TGTCGGACAT CTTTAAAGCA TTTTTCTTTT
28851 TATAGAATTT CACTTAATGT CCAATACTGA TTTAATGAGC TTGGGTTTAC
28901 ACATTATCTC TTGAAGAAAA CAAATGAACC TTTGTGTTCC AAAGCAATCC
28951 ATGTTTAAAG GGAAAAAATT ATGCATAACT CTGCCCAGCT TCACAGTAAC
29001 CTTTGGCAGG TGCCTTAGGT CCTCTGGGAC TCTTTTCCTT ATCTGAAAAA
29051 TGAAGGACTT GGATCAGGTG AATGGTTCCC AGCTCTGCAA CTTATGTGGC
29101 TCCTCAGAGG CACACAAGCT CTTTTCCATT ATTTGCCAAA TAATGGAGGC
29151 CCTGTCTTTA ACTGCAGTAC AACTACACAA AATACTTGAA ACTACAGTCT
29201 TCCTGGTTTT TGGTTGGAAC TGAATCAGTG CACTCTAGCA ACACTTATTT
29251 CTTGCTGTTC GTAGGCTTCA TTATGTGTTT GGTTAATTTT TTAAAACAAC
29301 AATAACATAT TCCATAATAA TTACAGCTTA ATTGGCAGAC TGTTTCAGTC
29351 TATAGGATCT GCAGGAAGGA GGAGTAATAA AGGGATTTTT GACTGAGCTC
29401 TTATGGAACA GAGTCTCTCT AGGCCCCTGT CATATCTGCC CTTCTGGGCC
29451 CTGGGGAAAA GTTGGCATCC CCAGTTGTGG TGCTCTCCAG GTGCCCTCAG
```

FIGURE 3-10

```
29501 GCTGTGGTGG AGGGAGCTTC CCATTCTCTC CTTCAGCCCA CTCAATTCAG
29551 AGGCTAGGGG CTGAAAGAAG CTTCTCTACA ACTGGCTGTT CACTGGGAGG
29601 TTAAGGGATG ACCATCCAGC CAGGCCTTCC TCAGGACATG GGAGGGCTTA
29651 TGCTTTAACA TGTGTAAATC CACTGCAATA ATGACTGGTT CTTTTACCCC
29701 ATAAGGTTGA GAATTTACCT GTAAACATTT TTGTCTGAAG AATTTGGATG
29751 TAAGTGAGGG CTGGGCCTCT ATCTTATCTC ACTTGGCTTC TCTCAGCACA
29801 GCACCTTGCC TGCTTGTTCT TACACATCCT AGATGCACAG TAACTATTTC
29851 CTAATTATTA GAAATCTATT AGAATCAATT GATTTCAGCT GGGCTTGGTG
29901 GCTCCTTCCT GTAATCCCAG CACTTTGGGA GGCTAAGGCT GGAGGATCAC
29951 CTGAGTCCAG GAGTTTAAGA CCAGCCTGGG CAACATAGGG AGACCCTGTC
30001 TCTACAAAAA ATAAAAAATT AGCCAGGCAT GGTGGTGTGC ACCTGTAGTC
30051 CCAGCTACTC AGGAGGCTGA GGCAGGAGGA TCTCTTGAGC CTGGGAGGTC
30101 AGACTACAGT GAGCAATGAT TGTGCCACTG CACTCCAGCC TGGGTGACAG
30151 AGTAAGACTC TGTCTCTTAA AAAAAAAAAA AAAAAAGTTG ATTTCTATTT
30201 GGATAGATAA ATAATTCATT TTAGGACCTT TCTTTTTCAC TTACAGAAAT
30251 CTGTTTCATT CTGGGCTGAG AAGCAGGTCC ATATTGCTAG GCATAGGAGA
30301 AAAAGGGGTC TGTCTGCATT TGCCCTTGGT GGTCTCAAAT TGGGGAGGGA
30351 AAGAAATGAA CACTTACTGG CTACCTTCTG TGAGCCAGGC ATCATGCAAG
30401 ACATCTGTAC ATAATTTAAT TCTCATAACC CCATAAGATA TTATTAGCAA
30451 TGTACAAGTG AGGAAACTGA GGCTCAGAGT CATGAAGTAA CTGGCCTTGG
30501 GTGACACAGA TGGTAAATGG CAGAGAAGGA ATATGGATCC AGGTCTTGAA
30551 AGAGAAAATC TCAACTGATT ATCTTTTTTA AAAAACTCAT ATGTTCTCTG
30601 CTGACTCAAA AGGTCTCTGT GTGGATCTGG GTTGACCCAC TGAAACTGACC
30651 ATCAGGGTTC CATGCACTTT GTATCTGCCC AAGCCCTCAG AACCCCTCAG
30701 TAATGTTTTG GAAGATGAGT TTTGGAGGTT GTCCTTAGGC ATAGCCTCAG
30751 CGTATGTAGG CCTCTAGGTG ATCTCCCCTA ACCTGAGGAT TTCAGCTCAA
30801 TTCACTCTGG CTCCTCAGGA CAGTGGGATG ACTGGTTCAG ACCTCAGCTT
30851 TACCACCTCC CAGCTGGGTA CTCTTCTACC TACAGCCAGG GCAGATTTTG
30901 ACTTTCACTT GAAACTTCCA AAAATTGAAA GGTAGAAAAA CAGCCTTGGC
30951 TTTGGGAAGA ACGTATGATG TCCATGGCCT CTAAGCATCT GAGGTGGGAC
31001 ATGTTCGAGT AGCACCTTAC AGTTCCAAAG TGTGTTCTGG GTTCTTTGTT
31051 TAAAAGAACA GAGACTGCTG GGGAATTGAA CACTGTGAAG TATATGAAGG
31101 AGGAGAATTG TGCTATTTAA CATTCAGTAC TTGGGCTAAA GGAGAAGCAT
31151 CACGAAGTGT TAACACTCAA AGGGTCTTGA GCTGTCAGGG CTCCAGCTTC
31201 CTTATTTTCA CAGGTGAGAA TCCTGAGGCT CAGCTGTTGA GATGTGCTGT
31251 CTCACTCCGG TGACATAGTA CAGTGGATGT GGCTTTGCAG CCAAGCACAC
31301 ATAGCTTCAC ATTCCAGCTC CATCAATTAT GTATTGGGCA GCTTTGCAGA
31351 ATGATTTGAC TTTAACTCTG CTTTTCAGTC TTCTGTAAAA CAGGGATAAT
31401 CCTGCTACCG TAGGGTTGTC AGGATTAGAG ATAATATAAA TAAGGTACCT
31451 CATATAGGAC CTGGATTATG GCTGGCATTC AATAAATAGT AGCTGTTAAT
31501 TGATAGCTAA GCTAGAACTC TGAAGTCTAC CATGGCAACT TCTTAAGTGG
31551 TCTGAGAACC CAGTTGTGTT CTGTGGCAAA ACACAGCTTA GGGATCCATA
31601 CCCAGCCCTC CTGTCAGCTG TTCACCTTCC AGTTCTTCAG AGACATGTGT
31651 GGCAGTGACT TTGGCCACAT AGCTGGCTGT GCCCTTTAAA GGCATTCCTT
31701 GACACAGATA TGTGGACTGG TGACGTTGCT CTCCAGCCAG GTGTTCTTCC
31751 CAGCAGGCTG GCCTGGCTGT CTCCTGCATG CCTGTACTTG TTTGTCTCCC
31801 TGCTCCCTCT CCTGGGCCTG GCCAGAGCTA CTTGCAGCAA ACAAAAGCAG
31851 GATATTGGCA ATGGAAAGGA GGGTGTGTTC TGGTGCTCCC ATGCCCTGCG
31901 GCGCACATAC CATTGCAAGG GCGTAACAGA GCCCAGGCCT GCATTTGGGT
31951 GCAAATAAGT CTGCACACAG AAGAAAAGAA GGACCTGGTG ACCAGGAGCC
32001 ATGGAACCCT TGTGCTCCCC TACCTGGGCT ACTGGTTCTT GCCACTCCTA
32051 CCATTTTCAG TTTGGAAATA TTTGTTAAGG CTTTGCTCTT CCAGGTCCTT
32101 TGCTTGGTGC TGAGTCTACC AAGAGTAAGT GGGATGCTGT TTTTGTCCTC
32151 AGGGAGCTAA CAGTCTAGTG AAGAAGAAAG ATGGTTGCCC AGGAACTTCT
32201 AAGTCAGAAG GCAGGAGGCA AGAAGGAAGC CCCTGCTCCT ACTGCCAGCC
32251 CTCTGTTGGG CACCCCATAG TTCTTCAGAA CCACATTTAA TCCTCACTGC
32301 AGGCCAGGCA TAGTGGCTCA CACCTGTAAT CGCAGCACTT CGGGAGGCCA
32351 AGGCGGGCAG ATCACTTGAG GTCGGGAGTT CGAGACCAGC CTCACCAACA
32401 TGGGGAAACC CCGTCTCTAC TAAAAATAGA AAAATTAGCC GGGTGTGGTG
```

FIGURE 3-11

```
32451 GCATGCGCCA GTAATCCCAG CTACTCAGGA GGCTGAGGTG GGAAAATCAC
32501 TTGAACTCGG GAAGCAGAGG TTGCAGTGAG CCGAGATTGT GCCACTGCAC
32551 TCCAGCCTGG GCGATAAGAG CAAAATTCCA TCTCAAAAAA AAAAAGAAAA
32601 AAGAAAAAAT CCTCACTGCT ACCTTGAAAG TAGGTGATGA CATTGCCATT
32651 TCACAAATGA GAAGTGAAGG GGCTAGCCCA AGATCACTTA GGTGGTAAAT
32701 GGTGGTGCTA AGATTAGAAC CTCAGATCAT CTAGGGAAAA ACACAGATAT
32751 GCACAGAGTT AAGGGGACCC AGGGTATTGT TTGTCCTCTT GTTTCACAGG
32801 TGGGGAAACA ACCCAGAGAG GGAAAGGGGC TTGTCCAAGG CAATTTAGCA
32851 CCCAAGAACT TGAACCCATA TCTCTCTCCT CCTCATTTAG AGCTCATCCC
32901 ACATGTATCT TATATTGAGA GGAGTGTGAG CCACATACCA AGAACAGTCT
32951 TCCCCTCTGC CTCCAACCTC ACTGTGCAGT TTTGAGACAC TTCACAGCCA
33001 TACTCTTCAT GCCATACCCA GCCCTTAAGA CCCTGAAGTT CCCCTTCCAT
33051 AAGACAAGTA GGAAAAGCTA TAGGGTAAAA ATAGCCATCA GTGTTTGTTG
33101 AGCACCCAGG AGGAATTGGG CACTCCAGAA AGATAAAGGG ATTCTCAGGG
33151 ACTTGCTTCT CTAGACTTCC CTAGCTCAGC TGCTTCAACT CATTCCTGCC
33201 CCTCTTCTCT ACCTCCCGCA GTGCTCAGAA GTAGTAGAAC TCACTGTGGC
33251 CTCTCACCTT GCATTGTTGA GTTTTATTTA GACTTTCTCT TCCTCAACTC
33301 TTCATAAGCT CATGAAAGGT GAAGTAGGGT GCCCTGTGTA TTTATCTTTT
33351 ATATCTGCAG TGCTTAGCAA GTTATAATAA TGCACTTGCC TGGCAAAAGG
33401 CTTTCTCTCA TACATTAGCT TATTTCCTCT TCACATTGGC TCTTTGTAGT
33451 AATAGGATGC TATTAGTTAT TTTCAATGAG AGAAAGCTAC TAAGAGAAGT
33501 TGTCCAGCTA GTGACAGTAA GTGGCTGATA AAGTGAGCTG CCATTACATT
33551 GTCATCATCT TTAATAGAAG TTAACACATA CTGAGTTTCT ACTATATTGG
33601 GTCTTTTTTT TTTTTTTTTT TTTTTTTTTA GAGACGGAAT CTTGCTCTGT
33651 TGTCCAGGCT GGAACGCAGT GGTGCAATTT TGGGTCACCA CAACCTCCGC
33701 TTCCCAGGTT CAAGCGATTC TCCTGCCTCA GCCTCCTGAG TAGCTGGGAC
33751 TACCAGTGCA CGCCACCACG CCCGGCTAAT TTTTGTATTT TTAGTAGAGA
33801 CAGGGTTTCA CCATGTTGGC CAGGCTGGTC TTGAACTCCT GACCTTGTGA
33851 TCTGCCCGCC TCAGCCTCCC AAAGTGCTGG GATTACAGGT GTGAGCCACC
33901 GCGCCCTGCC TATATTAGGA CTTTTATATA AGCTATCTCT AGCTAGCTAG
33951 CTAGCTAGCT ATAATGTTTT TTGAGACAGA GTCTGACTCT GTCACCCAGG
34001 CTGGAGTGCA GTGGCGTGAT CTCGACTCAC TGCAACCTCC ACCTCCTGGG
34051 TTCCAGTGAT TCTCCTGCCT CAGCCTCCCG AGTAGCTGGG ATTATAGGTG
34101 CATGCCACCA CGCCCAGCTA ATTTTTTGTA TTTTTAGTAG ACCAGGTTTC
34151 ACCATGTTGG CCAGGCTGGT CTCGAACTCC TGACTTCAAG TGATCCACCC
34201 GCCTCGGCCT CCCAAAGTGC TGGGATTATA AGCATAAGCC ACTGTGCCCA
34251 GCTGCTCTCT ATATTTTTAA TACATATTAT TTCCATTAAT TTCACAGCA
34301 GTTCATTTTA TAGATGAGGA AACTAGGCCA GAGAAGTAAA ATATCTTGCC
34351 CAAGATGATG TAACTAGTAA GTGGCAGGAT CAAGATTCAA ACCAAGCAAT
34401 GTTCAAACCT CTTGGAAGCA AGAATGTGGC CACTGTGGAA GGTGCAAGGC
34451 CTTGACAACA AGAATAGGGA AAAGAAGGAA CTAGAAGGAA AGAGATGGCA
34501 TGGGCTCAGC AGGCCAGGGA GCTCTTAGCT GTGTGTGTTG GGAAGCTCAG
34551 AAGGGAGGAA GAGGTTGTCT GTGCAGGTAA GTCCTGAGAA CACACCAGAC
34601 TTTTGAGAGG TGGAGCTTCA TAGCCAGGTC ATTAGGGGAG AAGGGAGCTA
34651 TAGATTTTTT TTTTTTTTTT TTTTTTTTTT TTTTTTTTAG AGACGGGGTC
34701 TTACTATGTT GCCCAGGCTG GTCTTGAACT CCTGGGCTCA AGTGATCCTC
34751 CCACCTCAGC CTCCCAAAGT GCTGGGATTA GAGGCATCAG CCACCCCGCC
34801 CAGCGAGCTA TGGATCTAAC ATGTACATCT TACACAGTGC TAATAGAATG
34851 TTGGGTTTCT TCCCCAATAT TTTATTTTGA AAAAAAATTC AAATATATAG
34901 AAAAGTTGAA AAATGTAGTT CAAAGAACAC CTACATACCT TTCACATAGA
34951 TTCATGATTT GTTAATGTTA TGCCACTTTG TATATATCTC TCTCCCTCCT
35001 ATCTGTATAC TTTTATTTAT TTATTTTTGC TGAACTATTT CAGAGTAACT
35051 TAAAGGCATC TTGATTTTAC CCTTGAACAG TTCAATATGT TTCTGCTAAG
35101 AATTCTCCTA TATAAGTCAG ATATCATTAC ATCTAAGAAA ATTCACGGCA
35151 ATTTTACAAT ATAATATTAT AGTCCAAATC CATATTTCCT CAGTTGTTCC
35201 AAAAAATGTT CATGGCTGTT TCCTTTTTTA ATCTAAATTT GAATCCAAGT
35251 TTGAGGCATT GTATTTGGTT GCTGTGTCTC TAGGGTTTTT AAAATCTGTG
35301 CCTTTTCTTC TCCCCATGAC TTTTTAGAAG AGTCAAGACC GGTTATTCTT
35351 ATAGAATAAC CCACATTCTA GATTTGCCTG ATTAGTTTTT TTATACTTAA
```

FIGURE 3-12

```
35401 CGTATTTTTG GCAAGAACAT TACATTGGTA ACGCTGTTGG TGATGGGTCA
35451 GTTTTGAAGA GTGGAGATGA TTAAACTGCT TTTGTTCATT GAAGTATCTG
35501 TCAAGACCAG AGATCCTTAA CTGGTGCCAT AAATAGGTTT CAGAGAATCC
35551 TTTATATATA CACCCTGTCC CCCACCTAAA TTATATACAC ATCTTCTTTA
35601 TATATTCATT TTTCTAGGGG AGGCTTCTTG GCTTTTATCA AATTCTAGA
35651 GGGCCCCAAG ACCCAAAGAG GTTATGAAAC ACTAGTCTGT CCACTGAGGC
35701 AGGCAACACA GAGCTGGTTT CTGGGGCCTT GTTCAGTCTG AACCAGCTTC
35751 CCTTGGGGAG ATAGCACAAG GCTGTAACTT TGCCCCATCT TGGCTTTGGA
35801 TCAAAGAGGA CTGTCCATTT TGTTGTCATA CCTAGGAACC AGGGACAGCT
35851 TATGTGGCCT GGTTCCAGGG ATCCAGGAGA ATTTCAGTTC TTGTCTTGCC
35901 TTTCAGGTGT TCAGAATGCC AGGATTCCCT CACCAACTGG TACTATGAGA
35951 AGGATGGGAA GCTCTACTGC CCCAAGGACT ACTGGGGGAA GTTTGGGGAG
36001 TTCTGTCATG GGTGCTCCCT GCTGATGACA GGGCCTTTTA TGGTGAGTGA
36051 ATCCCTTCAT ATCTGCCCCT CTTGGTCTTC AGAGTCCATT GACAGTGCTT
36101 CCAGTTCCCT GTGGCCTGTT AATCTTTTAG TCTTTCCATC AGCCAGGGCA
36151 TCTCCCTTTA TTTATTCATT CATTCAACTA GCAGGTATCA ATTGAGCACC
36201 TACTAAGTGA AAGGTAAGAT CCTTCCCTCA AAGACTTAAT AGTTGAACGT
36251 TGGGAGTGGG AGGAGAGGCA GGCAGAGAGG AGACACAATA TAGTTGGATA
36301 AGGACCTCCA AGGAGAGTGT TACAGGCTGA GAGGAGGATA TACTTAGGTT
36351 GTCTTTAGGG AATCAGAAAA GGAGACTCTG GAATAGGCTG GCAGAGAGAG
36401 GGGCTACCTC CTATACCTGC TCTGGACAAA CGACTTTAAG CATAGTGACA
36451 GATTTGCCAA CCCTGTATTG GAAGAACTGA TCTTTTTTAG TGGGGATGAT
36501 TACTTCTGGG GATTTCTTCT CATAACTGAG ACCAAAACAG TTTTGTGCAG
36551 TCTCAGAAAT GACAGGAGGT ACCAATCTGA CACTTCCTTT GGAAGCTCTA
36601 GGGCAGAGAG TGAAAGAGTG GATTTTGACG GGGGCCTTGC TTGGAGGTCA
36651 TTCACCCACC CCTGTCCTCA CTCCAGCAAC AGTGATAACT CACTTCCTTC
36701 CTCCCTTTGT ACACCCTTCT CCCCACCTGC TCACAGGTGG CTGGGGAGTT
36751 CAAGTACCAC CCAGAGTGCT TGCCTGTAT GAGCTGCAAG GTGATCATTG
36801 AGGATGGGGA TGCATATGCA CTGGTGCAGC ATGCCACCCT CTACTGGTAA
36851 GATAGTGGTC CTTTGTCTAT CCTCTCCCAT ATAAGAGTGG CTGGCGGGGA
36901 GGGACAGTGG CAGGGTGAGT TGGGCAGAAG GAGTGTTAGG GTAGTCAGAG
36951 CATTGGATTC TTACCACAGC AGTGCTCTTA ACCAGCTCTT TAACTTGTAA
37001 GCAGAATGAT TTACACATGT CTCTACCCTT TTTCCTTACC AACCTTGAAA
37051 ATGTCTTCAC TCTGCCCTGC AATCCTCCCA GTGGGAGGCA CTCTTCAAGG
37101 ACGATCCCAG AACATTAAAG TCAAAGACCC CTTAGAGCTC ACCCTGTCCA
37151 ACCACCTTGG TTGATAAAAG AAGTCAGCCT GGGGCCCATG GAATAGAATA
37201 GTACAAGGGC AAGGTTCTCA TTGTGAGTCA AAGGTAGAGT GAAAGAGAACC
37251 CAGACCATCT CACCCCAACC CAGGCCAGTG TTTTTCCAAA TATACCACTT
37301 GCTGCAGATC TAGCTCAGCA CCCCCAGTCC CAGCCCACCC TGAGAACCCA
37351 GGCTCCTCAT TCTGAGCAGC CAGCTAGAAT CATGACAAAG AGGGTGGTAG
37401 TGAGACTATG GGTACTGTTG CTTAAAGCCA CATGGTGCAG TGGTTGCTGG
37451 GGGGCTTCTG TGTGGGACTC TAGCATCTTA TTCCCCCCTG TGCCCTCTCC
37501 CCAGTGGGAA GTGCCACAAT GAGGTGGTGC TGGCACCCAT GTTTGAGAGA
37551 CTCTCCACAG AGTCTGTTCA GGAGCAGCTG CCCTACTCTG TCACGCTCAT
37601 CTCCATGCCG GCCACCACTG AAGGCAGGCG GGGCTTCTCC GTGTCCGTGG
37651 AGAGTGCCTG CTCCAACTAC GCCACCACTG TGCAAGTGAA AGAGTAAGTA
37701 TTTTGAGAAC CCTTCAGCAG GGGTTCTTGA GCAGAGTCTG TAAATGGGCC
37751 TCAGAGGGCT TAGACCTCCA AAGTCTCATG CAGAACTCCC TTTATTCTCA
37801 TCTCATATCT TTCTCCTGGA CCCCACTATG CTGTAACCGT ACCTGGGCCT
37851 TGGCACTTAC TGTTCTCTCT GCCCAGGCTA CTTCCTACCC GATACTTAAG
37901 GCAAGAATCA CTCACCTTTC AGGTGTCAGG TTTCAGGTCA TGTTTGCTCT
37951 TTGAAATCAT CTGGCTTGAT TATGTGTATT AGTTGTTTAT CTTCTATCCC
38001 CTCCACTAGA ATGTAAATTC CAGAAGAAAC TTGCTGTCTT ATTCAGTGCT
38051 GCATGCCCAG GGCTTGGAAG AGTACCTGGC ATATAGTAGG AGTTGATTGA
38101 TTATTATTTT GTCAGTCGAG AGAATGAATG GAGAAAATGT GGTCCATGGC
38151 CCAAAAGAAG TTAAGACCCT ATCCTAGATT CAGGCCAGAG ACCAGATGGA
38201 GAAAGAGTCT GTGTCTATCT AATACCAGTA ATGTCGTACC TCTGGCCGCT
38251 TACCATGTAA ATATTGATTG TGTATCTACC ATGTGTTGGA CACTAGGCTA
38301 GTGCTTGCAC AGCAGGTGAA AGATACTAGA GTTTGGGAAG TCAGGAGGAG
```

FIGURE 3-13

```
38351 CTAAGGTCTG TTCTACAACC TTATTAGATG AAGAGGAGAG GGAATTGTGT
38401 TCAGGGCAGA GGGAGAAGCA TTTCTCCAAA AGTAGGAGTC TTAATCATGT
38451 CTGATGTAGG TTGAGTGTGG CCAGAAAAGG GGCTGTTAAG TATAGAGGGC
38501 CTGGATTATG AAAATCCAGC AGATCCATTG AGAGTTTAAG CAGCAAGGTG
38551 TTGTGACCAA GTTAACATTT TAGAAGGATC ACTGGTATGG AGGTTGGATT
38601 GGAGAGGGGA AAGCCTAAAG GTATAGAGAC TAGTTAGGAA GCTATTGTAG
38651 GCTGGGCATG GTGGTTCATG CCTGTAATCT CAGCACTTTG GGAGGCTGAG
38701 GTGGGAGGAT TGCTTGAGGC CAGGAGTTGA AGACCAACCT GGCCAACATA
38751 GCAAGACCCC GTCTCTGTTT TTCTTAATTA AAAGAAAAGT CCAGACGTAG
38801 ACATAGTGGC TCACGCCTGT AATGCCAGCA CTTTGGGAGG CCAAGGTGGG
38851 CAGATTGCTT GAGGTCAAGA GTTTGGGATT AGGCCAGGCG CAGTGGCTCA
38901 CGCCTGTAAT CCCAGCACTT TGGGAGGCCG AGGTGGGCGG ATCACAAGGT
38951 CAGGAGATCA AGACCATCCT GGCTAACACA ATGAAACCCC GTCTCTACTA
39001 AAAGTACAAA AATTAGCCGG GCATGGTGGC GGACGCCTGT AGTCCCAGCT
39051 ACTCGGGAGG CTGAGGCAGG AGAATGGCGT GAACCTAGGA GGCGGAGCTT
39101 GCTGTGAGCA GAGATCACGC CACTGCACTC CAGCCTGAGC GACAGAGCGA
39151 GACTCCATCT CAAAAAAAAA AAAGAGTTTG GGATTAGCCT GGCCAACATG
39201 GCAAAACCCC ATCTCTACAA AAAGTACAAA AAAATTAGCT GGGTATGGTG
39251 GTGCGCGCCT GTAATCCCAG TTACTCAGGA GGCTGAGGCA TGAGAATTGC
39301 TTGAGCCTGG GAGGTGGAGG TTGCAGTGAG CCCAGATCAT GCCACTGCAC
39351 TCCAGCCTGG ATGACAGAGT AAGATGCCAT CTCAAATAAA AATTAAAAAC
39401 AAAGTTTAAA AAAAAAATAG AAGCTATTAC CGTGATCCAG GTAAGAGATG
39451 TGAATAACTA CAATGATGGA AAGAAGGCAG AGTTCTTAGA GATGGGAGTA
39501 GGAGAGATGA GGGAACTCCA GATTGGGAAG ATGATGTTCA AGTTTCTGGC
39551 TTAGGCCACA GGGTGAGTGG CAATTCCCTT CACTGAGATG GGGCATCCTG
39601 GAAAAGGTGT TGCCTTTCTG TGTGGGTATC CTGGGCCCCT TAGGGGCCAC
39651 TGGTGGCCTG GGACCTGGTA AACCTTCCCT GCACAAGCAG AATTGGTCAA
39701 GCAGGTTTTT AGGACATCTT TACCCTGCCT CAACTCTTGT CTGGCCCAGG
39751 GTCAACCGGA TGCACATCAG TCCCAACAAT CGAAACGCCA TCCACCCTGG
39801 GGACCGCATC CTGGAGATCA ATGGGACCCC CGTCCGCACA CTTCGAGTGG
39851 AGGAGGTAGA GTGTGTGTCT AATCTGTCTT GTGAGGGTGG GACATGGAAC
39901 AGATCCTCTG GGAAATCAGG CTGTAGCCTT TACCTTTTCC TACCCCCAGC
39951 CCATCTCTTT GTCTTAGCAT TGAGCCTGTG ACCACTGGTG ACCTATTTCA
40001 GCGTAACAGG TTCCCAGGGT AGCAGGGATG GTTGATGGAC GGGAGAGCTG
40051 ACAGGATGCC AGGCAGAGGG CACTGTGAGG CCACTGGCAG CTAAAGGCCA
40101 CCATTAGACA AGTTGAGCAC TGGCCACACT GTGCCTGAGT CATCTGGGTT
40151 GGCCATGGGT GGCCTGGGAT GGGGCAGCCT GTGGGAGCTT TATACTGCTC
40201 TTGGCCACAG GTGGAGGATG CAATTAGCCA GACGAGCCAG ACACTTCAGC
40251 TGTTGATTGA ACATGACCCC GTCTCCCAAC GCCTGGACCA GCTGCGGCTG
40301 GAGGCCCGGC TCGCTCCTCA CATGCAGAAT GCCGGACACC CCCACGCCCT
40351 CAGCACCCTG GACACCAAGG AGAATCTGGA GGGGACACTG AGGAGACGTT
40401 CCCTAAGGTG CCACCTCCCA CCCTGGCTCT GTTCTGTCCT ATGTCTGTCT
40451 CTCGGATGAA GCTGAGCTGG CTTTCAGAAG CCTGCAGAGT TAGGAAAGGA
40501 ACCAGCTGGC CAGGGACAGA CTATGAGGAT TGTGCTGACC CAGCTGCCCC
40551 TGTGGGGATC ACAGTTTACA GCCAGAGCCT GTGCGGACCC AGCTGTCTGC
40601 CAGGTTTCCT TAGAAACCTG AGAGTCAGTC TCTGTCCACT GAACTCCTAA
40651 GCTGGACAGG AGGCAGTGAT GCTAAACCCT GAAGGGCAAC ATGGCCTATG
40701 GAGAAAGCAT GGAGCTCAGA GCCTGGAGTA CGGGCACAGA TAGGATTGAA
40751 TAAATTGTGT AGAAAGACTT TGAAAACAAT AAAGCAAAAG ATGAATGAAC
40801 GTTTTTTTA GACTTGAGGG ACCAACAACC CCCAAACCCC AGATTCTGCC
40851 AGGTCCATGG GGAAGGAGAA GTTGCCTTGA GTGGAAGCCC CAAGTAGGGA
40901 GACTTACAGA AAAGAAGTCA AGAGCACTGG CTCCCAGGCA GAAATACTGA
40951 TACCCTACTG GGGCTTCAGG CTGAGCTCCT CCCTTCACAA ATCACTTCAT
41001 CTCTCTGAGC CTGTTTCTGC ATCTGTGACA TAAGATGGTA AGATAAAGGT
41051 GGCTGTCTCA CCAATTATGT AAGGATTAAA TGTGGAAAAG GACATAAAGT
41101 TGTATAGTGC TGCCATAGGG ACAGTGTTCA GTAAACGTGA CACATTCTTA
41151 GTATCACTAA GAATCAGGTT CTTGGCCAGG CACCGTGGCT CATGCCTGTA
41201 ATCCCAACAC TCTGGGAGGC CTAGGTCGGA GGATGGCTTG AACACAGGAG
41251 TTTGAGACCA GCCTGAGCAA CATAGTGAGA CACTGTCTCT ACAAAAAAAA
```

FIGURE 3-14

```
41301 AATAATAATA ATAATTGTTT TTAATTAGAT GGGCAGGGCA CTGTGGCTCA
41351 CACCTGTAAT CCCAGCACTT TGGGAGGCCA AGGCCGGAGG ATTGCTTGAG
41401 GCCAGGAGTT CAGGAGCAGC CTGGGCCACA TTCCTGTCTC TACAAAGAAT
41451 AAAAAAGTTA ACTGGGCATG GTGGCACATG CCTGTAATCC CAGCTACTCA
41501 AGAGGCTGAG GAGGAGGATT GCCTGAGCCC AGGAGTTCAA GACTGCAGTG
41551 AGCCTTGATC ACACCACTGT ACTACAGCTT GGGCAACAGA GTGAGACCTT
41601 GTCTCCAAAA AAAAAAGTTT GTTTTTTTTT ATCCACTCTC CTCACCAAAC
41651 AAACTGAGTA AGTTAGAGCC CTCTCAGCTG GCATGTGTTG GAAACAGTGC
41701 CCTCTCATTA AAGTGCTGCC CTCACTCCCA TTGCCTCTTG GCCTTGGTCA
41751 GTATGATGAA ATTAGTGGGA GGCAGGGCAA CAGAGGGCAG GGAAGAGCTA
41801 GAAATCCATG GCCTGGAAAA GGGAAGATTT GGGAGTGGCC AGGTATCTGT
41851 AGAGCCACCA TGCAGAGGAG GGGGGCAGCT AGCCTTGTGT GCTCTGGTGG
41901 GCATGGTCAG CAGGAGGCAG AGCAAAAGGA CAAGGGTAAG TAAACCTGTA
41951 GGTCGGACA AGCCAAGAGC CATCCAGCGT CAGTCCTCTC TGGGTAGCCC
42001 AAGTAAAGCA GGAGCATACC CCAGAGAGAA AGTTCGCAGG GCTGTTCACC
42051 TGCAGTGCTG TGGACTTCAA CCTTCTTGTT CCTTCTTCAG TAAGTGAAAA
42101 TAACAGTCAT TGACCATGAC TATTATCGAC CGCTTTTGAA AATGTAAACA
42151 TAGTGACTTT ATTGCTGTAA AAATCATACG TGTTTATCAT CTTAAAATTC
42201 AGGAAACATG GACAGGTACA AAGATGTGCA AAATATCATC CAAAATCCCA
42251 TTTGCTGGCC AGGCACGGTG GCTCACGCCT GTAATCCCAG CACATTGGGA
42301 GGCCGAGGCG GGCAAATCAC TTGAGGTCAG GAGTTTGAGA CCAGCCTGGC
42351 CAACATGGTG AAACCCTATC TCTACTAAAA ATACAATAAT TAGGCTGGGC
42401 GCAGTGGCTC ACGCCTATAA TCCCAGCACT TTGGGAGGCC GAGGTGGGCG
42451 AATCACAAGG TCAGGAGTTT GAGACTAGCC TGGCCAATAT GGTGAAACCC
42501 CATCTCTACT AAAAATACAA AAATTAGGGC CGGGTGTGGT GGCTCACGCC
42551 TGTAATCCCA GCACTTAGGG AGGCCGAGAC AGATGGATCG CGAGATCAGG
42601 AGTTCGAGAC CAACCTAGCC AACATGGTGA AACCCCATCT CTACTAAAAA
42651 AATACAAAAA TTATTCGGTT GTGGTGGCAC ACGCCTGTAA TCCCAGCTAC
42701 TTGGGAGGCT GAGGCAGGAG AATCTCTTGA ACCTGGGAGG CAGAGGTTGC
42751 AGTGAGTGGA GATCCCGCCG TTGCACTCCA GCCTGGGCGA CAGAGTGAGA
42801 CTCCATCAAA AAAAAAAAAA AAAAAAAAAA AAATTAGCCG GGCGTGGTGG
42851 CGTGCACCTA TACTCCCAGC TACTTGGGAG GCTGAGGCAG GAGAATCGCT
42901 TGAACCTGGA AGGCGGAGGT CGCAGTGAGC CGAGATCGTG CCATTGCACT
42951 TCAGCCTGGG CGACAGAGCG AGACTCTGTC TCAAAAATAA TAATAATAAC
43001 AATAACTAGC CGGGCCTGGT GGCACATGCC TGTAGTCCCA GTTACTCAGG
43051 AGGCGGAGGC ATGAGACTCA GGTGAACTAG GGAGACAGAG GTTGCAGTGA
43101 GCCAAGATCA CACCACTGCA CTCCAGCCTG GTTGACAGAG CGAGACTCTG
43151 TCTCAAAAAA AAAAAAATCC CATTTGCTCA TTTTTTGGAT ACTAGTATAA
43201 CTATCACTCT AAACCAGTTA GTACTTAAAT CAAGCAGATA TGGGAGATGG
43251 TGAATTACCA TCTACAGTGT TGTCATATAT GTCACATACT GAGCATTATC
43301 AGCTAGTAGA ATCTAGTTAA TTGTTCTATG TGTGATGTAT GCAGAGTTCC
43351 CATTTTGAAT GTGTTTTTAC TATGCTTAAA TAAATGACTG ATGTCAGCAA
43401 CCCCAAAATG ATACATCTGA TGTAAGAGCC CCTGTTCCCC AATAATAACA
43451 TCTAAACTAT AGACATTGGA ATGAACAGGT GCCCCTAAGT TTCCTCCCTC
43501 CAGGGTTTCT TGGCCGGTCT CTGAGGACTA CACATCCCTA CTCCCGTCTT
43551 TCCTCATCTT CAGGCGCAGT AACAGTATCT CCAAGTCCCC TGGCCCCAGC
43601 TCCCCAAAGG AGCCCCTGCT GTTCAGCCGT GACATCCAGC GCTCAGAATC
43651 CCTTCGTTGT TCCAGCAGCT ATTCACAGCA GATCTTCCGG CCCTGTGACC
43701 TAATCCATGG GGAGGTCCTG GGAAGGGCT TCTTTGGGCA GGCTATCAAG
43751 GTGAGCGCAG GCAACAATTG CTTTGCTCTT CTGCCCCAG TCCCTCTGTC
43801 ACTGTCTTTC GGGGATTTCT CATCACTTGG CCCACCCCA CACCATGCAG
43851 GATGCCAGGC CTCCTTCCTG GCTTTGGGTG TTGGTGTGAG AGGTATCCTT
43901 CACCCCCACC CAGGCCACCT AAGGTCAATG TTGCTGTTAC AGTGAGCTTG
43951 TGGACCTGGA GATCCAGGTT GGGTTGAGCT GTGCCTGTGG CCCTCCTGCC
44001 TCCAGTCAGT GGGTGTTTGT TAGGTGCCTG CAGACCTCAG TACCGGGCAT
44051 GCTACAAGGA GCACACAGGG GAATGGCTCC TGCCTCCCTG GTGAACAGTC
44101 TCAGGGACTA ACCTCTCTCT TTCTCTCCTC CTCCTCCTCT TCTGCTGAGA
44151 ACTGGGAGGG GGGTCAGGT AAGACGTGTG TCTCAGCTTG GGGGCAGCAG
44201 GGCTGGAGAG CTCACCCCCG ATCCACCCAG CTCCCTGGTG CATGTCTTTG
```

FIGURE 3-15

```
44251 GCACTGACCT TCCTGCCCCC AGACTTCTGT TCACTCAGGA GACTCACTTC
44301 TATGCCAAAT GACCAGAGCC CCTGCTTGGC TTGGCAGCAT CCCCTCCTGC
44351 CTTCTTCCCC ACTTCCCTTT TCTGGGTTCT TGCCTGTCCT CTGTGCATGC
44401 CCAGCTCTCC AGGAAAGAGG GTTTGCTTCC GTGTGAGTCC CATGTTGCTC
44451 CACGCTGCAT CTTCCACACA TGAACTCTGT CATTCTGACC CGGCTCAGTG
44501 TGCCCTCCAA GGGATGGGAT GGCCAGCTGC ATAGATTTTC TCAAACAGTT
44551 CTCCAGAACT TCCTCTGGTC TCAGCACCAT TAACAGTCAC CCTCCCTGTA
44601 GGTGACACAC AAAGCCACGG GCAAAGTGAT GGTCATGAAA GAGTTAATTC
44651 GATGTGATGA GGAGACCCAG AAAACTTTTC TGACTGAGGT AAGAAGATGG
44701 AGGGGGCCCG GGAGGTTGGT GTCACCATTG GAAGAGAGAA GACCTTACAA
44751 ATAATGGCTT CAAGAGAAAA TACAGTTTGG AATTACTGTC TTAAAGACTA
44801 AGCAGAAAAG AGCCCTAGAG GAATATCCCA CTCCCTCTAA ATTACAGCGT
44851 AATTATTTGT TCAATGAACA CTTACTAAAA GCAACACAAA CAGGGTACAA
44901 GGGATGCAGT AACAAAAGAT ACAGGGTTCA GAAGAGCTCT CAGGTTATGA
44951 GGATGATGGA CATGAAAACA CTCCAATTTA GTACAACTCA ATGTTATAAT
45001 CCTCACCTGA ACGCCCTGCT AAGGGAGCCT GGAGGGGAGC TCCCTGAGCA
45051 CTCACACTCC TTGGGCATTT ACAGTTTTCA CTACCCCTCC CAAGTTACTT
45101 CATGGAGTAA CTTAAGTTGG GGACACCTGT GGTCTGGGTA TTGCCCTCCA
45151 AGCCACTTGG CCACTCCCAC CCCAGTTCTC CCAATGCAGT TCCAAGGGTA
45201 AGGCCTATGA AGCCATCTCC ATCTATATGG TGGTGGTCTT CCCTCATCCT
45251 GATCTTAGTG CCCTGTCATA TCACAAGATA GGAGGTAGGA GATACAGGT
45301 GTAACACTTG TCAAGCTGAT TCCTTGGAGG GAAGAGGTAA GGAAGACAGT
45351 GAGAAGTTAA CCACCAGCTT TCCTTGGCTT CCCCCACCCC CAGGTGAAAG
45401 TGATGCGCAG CCTGGACCAC CCCAATGTGC TCAAGTTCAT TGGTGTGCTG
45451 TACAAGGATA AGAAGCTGAA CCTGCTGACA GAGTACATTG AGGGGGGCAC
45501 ACTGAAGGAC TTTCTGCGCA GTATGGTGAG CACACCACCC CATAGTCTCC
45551 AGGAGCCTTG GTGGGTTGTC AGACACCTAT GCTATCACTA CCCTAGGAGC
45601 TTAAAGGGCA GAGGGGCCCT GCTTTGCCTC CAAAGGACCA TGCTGGGTGG
45651 GACTGAGCAT ACATAGGGAG GCTTCACTGG GAGACCACAT TGACCCATGG
45701 GGCCTGGACC ACGAGTGGGA CAGGGCTCAA CAGCCTCTGA AAATCATTCC
45751 CCATTCTGCA GGATCCGTTC CCCTGGCAGC AGAAGGTCAG GTTTGCCAAA
45801 GGAATCGCCT CCGGAATGGT GAGTCCCACC AACAAACCTG CCAGCAGGGC
45851 GAGAGTAGGG AGAGGTGTGA GAATTGTGGG CTTCACTGGA AGGTAGAGAC
45901 CCCTTCCTAT GCAACTTGTG TGGGCTGGGT CAGCAGCTAT TCATTGAGTT
45951 TGTCTGTGTC ACTGAAACTG ACCCCAGCCA ACTGTTCTCA GTTCACAGCC
46001 CTGTTTTCAA AGAATTACAC ATCTCTAAAG GCAAACAGGG CACGGACAAG
46051 GCAAACTGGA GAGGCAAACT GTAGCCTGAG ATGGCCTGGG CTTGCCATCA
46101 CAGGTATTCA GGTGCTGAGG GCCCTTAGAC CAACTAGAGC ACCTCACTGC
46151 CTAGGAAATC AATGAAGGGG AAATGAGTTC TAGCGGAGCC CTGAAGGATC
46201 AGAATTGGAT AAAGTTCTTA TTGGCAGAGA GGCACCAGGA TTGAAGTGAC
46251 AGGAGCAAAG ACCTGGGAGG AAAGAGGAGA AAATCATCTA TTTCACCTGG
46301 AAACAAATGA TTCCAAGCAT AGAAATAATA ACAGCTGACA AGTACTGAGT
46351 GCCCTCTATA TGCTAGGCAC TGGGCTGAGG GATTAACATG CATGTGCATG
46401 TTTATTCCTC ATGACAACCT TGGTTTCCAG ATAAGCTGGA CTGGAAAGGG
46451 ACAGAGCTGG GATCCTGGGC TAATCAGTCT GGTCGCCAAG CCTGAGACTT
46501 TAGCCACTGC CCTTCACATG GGGGTCCATG AAAATAGTAG TAGTCTGGAA
46551 CAGTTTGGGG .GTACATCAAG GTCGCTGTGT TTTAAGCTAT GGAGTCTGGA
46601 CTATAGGAGA CAAATGTAAA AGAGTTTTTT GGTTGACTGG CTTTTTGGTT
46651 TTTTTGTTTG TTTGTTTGTT TGTTTGTTTG TTTGTTTGTT TTTTCCTGTT
46701 TCTGGGGCTT GAATCAGGAA GGAGGTTTTT TTGTTGTTGT TGTTTTGAGA
46751 AAGGATATTG CTCTGTTGCC CAGACTGGAG TGCAGTGGCA CGATCATGGC
46801 TCACTACAGC TTCGACCTCC TGGGCTCAAG CAATCCTCCT GCCTTAGCCT
46851 CCCAAGTAGC TGGACTACAG GTGTGTACCA CCACACCTAA TTTTTTGAAT
46901 TTTTTTTTCT TTTTTTTTTT TTTTTTTTT GGTAGAGACA GGTTCTCACT
46951 TTGTTGCCCA GGCCTGAATC TCAAACTCCT GGGCTCAAGC ATTCCTCCTG
47001 CCTCGCCCTC CCAAAGTGTT GGGATTACAG TTGTGAGCCA CCATGCCCGG
47051 CAGGAAAAGA TTTTTAAGCA AGAAAGCTTA AGAGCTGTGG TTTTTCCAAA
47101 ATGAGTCTGG GCTGGCACAG TGGCTCATGC CTGTAATCCC AGCACTTTTT
47151 TGGGAGGCCG AGGTGAGTGG ATCACTTGAG GTCAGGAGTT TGAGACCAGC
```

FIGURE 3-16

```
47201 CTGGCCAACT GGTGAAACCC CTGTTTCTAC TAAAGAAAAA AATGCAAAAA
47251 TTAGCTGGGC GTGGTGGTGC ACGCCTGTAG TCCCAGCTAC TCAGGAGGCC
47301 GAGGCAGGAG AATAGCTTGA ACCTGGGAGG CAGAAGTTGC AGTGAGCCAA
47351 GATCACACCA CTGCATTCCA GCCTGGGTGA CAGAGTGAGA CTTCATCTCA
47401 AAAAAAAAAA AAAAGAGAGA CTGATATGGT TAGTACATTG GGGTGGAATG
47451 CGGAGGGTCC AGGGAATGGA GCCCTGCATA GGGGGCTAAT GAAACATTTC
47501 AGATTTCTGA ATTAAGGTAG TGGCTGTGGG GACAGGAGCC TGGGAGGCAG
47551 GGTGGAGTCA GAATGGAGAG ACTGGTTGGC AATGAGGGAA CAGGAGGAGG
47601 AGGAGGAGGA GTTACGAGTG GCTTGAGGTG TCACTTACCA GACATTTGGG
47651 GGATGGGGGA TAGCCGTGAT TGTTGAGCAA CTGGTTTGGG AAGAGCTAGC
47701 ATTGATCCCT GCTGTTCTGT GCTAGCAGAA CCTATCAGCA TCTTCTGGGC
47751 AGGAAACTGG CTCCATGAGA CTGGCTTAGG GAGAGGCTGC TAGTCACCTA
47801 ATCTGCAGAG AAGGGGCAGC TGGAGCTGTG GGACAGAAGA GGCATCCATG
47851 TAGCTGGTGG GGGTGTCTCA GCTTGTGAAG AGGAGATGGC TTTGAGCAGG
47901 GCTGACACTG AAAAGGCTGG AAGAAAAAAA CAGACACACA AGAGTCTCAG
47951 GATCAGGTAG CATAGGAAAG TTGTGGACAG TCTTTGAGGA GCACTCCCTC
48001 AGGCAGGCAG GCAGGCAGGT CATGAGCTAT AGCGATTCAG GAAGAGCTCC
48051 CTGGGTGTGT GAGCAGCTCC AGGAGCCTAA GGGATGAAAG TAGTATTGCA
48101 GGGGGCTGGA GAGCAAGGAG TGGCTCCTTC TACATTTGCA AGGGAAGGAG
48151 AAAGGAAGTT GCTCCTGAGA GTGGTAAGAG TCAGTGGTGG AGGCCTGGAG
48201 AGGAGACATA ACAAACAAAT TTGTTGACAA ACATTTTGGT AGGAAGGGGG
48251 AGAGCTTAAA GTTTAGACAG TGGGGAAGGT GGAGTCTTAG AGGAGGTGAA
48301 TGTCTGAAAG ACAGAGCTAG CTGGAGCAAG AAGTCACTTC TCTGTTGCAG
48351 GCAGGAAGGA TCCAAAGTGG CTCAAGCCAG AGATTGGGAG AGTGGGAGG
48401 AGGGAGCAGC CTGGATCTAA GTAAAATGGG TAGAGGTGGA GGGGGTGCTG
48451 CAACGGCCAG GGTTTTCTGA AGTTGGGGAC ATTAGGAGAG AGCTGTGAGG
48501 GCTTTGGCCA GCCACTGTGC TAGTGATTGG TGAACCAAAG GATGGGCAGG
48551 AGATGGCAGC AGGGAAGCAG AGGAAGTCCA GGCTTCCTGT TGGTATTGGG
48601 ACAAGGGAGA GGCCATAGGA GGCCCTGGCC CTGTTGTCCA GGTTGGGTTC
48651 TGAAGCTGGG TGGGCATGGC CTGGTAGGAG AGCATCTATG GCGCCCAATT
48701 CCAGATTCAG GGTCTAGTTG ATTTGCTGGC CCTGTAGCCT CAGCTCATGC
48751 TTCTGTTCCA GGCCTATTTG CACTCTATGT GCATCATCCA CCGGGATCTG
48801 AACTCGCACA ACTGCCTCAT CAAGTTGGTA TGTCCCACTG CTCTGGGCCT
48851 GGCCTCCAGG GTCCTATCCT TCCTGGCTTC CTTGTCACAA AGGAGGCTGA
48901 CTTGTCCCCT CTGGCTAGAG GGCAGAGGTG TTGCCTAGGA GCTCCTATCT
48951 TTCCCTTCCT GCTTCTTCCA ATGCCCTTCT CTGTCCTCTG GGAGCTCCGA
49001 GACACACACA GACATAATTT CACCTTCTCT CATTAGCAAC CTTTGAAATA
49051 ATTTGATTAG AAGGGACTTC AGAAGTTTGT TGACTATATG TAGAAAACCC
49101 TGTCATTTTA CCTGCTTTTG CCCCATAGTA GTCTTGTAAA ACAGTTTCATT
49151 GCTGACCCCA TTTTACAGTG GTGGCACCTG AAGCCTCAGC CTGAGGCCAC
49201 CGAGCTAGTA AATTTACAGG GACCAGTTTG AGACCAGCAT TCCTCCCACT
49251 GCCCCTCAGC TGTGGTGGTT ACAATGTTGT TTGTCTTACT GACTTGCTAT
49301 CTGGCTTCCT GGGTGTCTAC CGGCTGGCCC TGGCTCTGCC CTCTAGACCC
49351 ACACCACGCA ATCTTCATTC CTTTCCCACA TGACTGCCCT GTAGCTATTC
49401 AAAGAGCTTG TCTCCCCCAA GTCTCCCCAT CTACTGCCTC CACCTTGCCT
49451 TTTTCTGTCT TATCCTGGTT CTAGCCACTG CCTGAAATCA TTTTAGGAAT
49501 AAGACAGGAC AGGGAAAAAC AAAAGCAACC CCCTGTCCCA CCTCTGAGTT
49551 CCACTCTCCA AGTCCCTGAG CCTCACCTCC AGGGCTCCAG TGGCTCTGCC
49601 ATGAACCCAC TGTGGGCTGG GAGTCTGCTG TGCACAGATA CCAGACCCTC
49651 AGAAACACAA ATGCCAAGTG TGTCTGTTTT TTTGTTTTGT TTTGTTTTGT
49701 TTTTTAGATG GAGTCTCATT CTGTTTCCCA GGCTGGAGTG CAGTGGTGCA
49751 ATCTTGGCTT ACTGCAGCCT CTACCTCCCG GGTTCTAGTG ATTGTTCTGC
49801 TTCAGCCTCC CAGTAGCTAG GACTACAGGC GTGTGCCACC ACGCCCAGCT
49851 AATTTTTTTT TTTTTTTTTT TGTATTTTTA GTAGAGACAG GGTTTTGCCA
49901 TGTTGGCCAG GCTGGTCTTG AACTCCTGAC CTCAGGTGAT TCACCCGCCT
49951 TGGCCTCCCA AAGTTCTGGG ATTACAGGTG GAAGCCACCG TGCCTGGCCT
50001 GAGTGTGTCT ATTTGATAGA GCTTTCTGCT CTGATTCTCC CTTGCTATAC
50051 ACCTTTTCTC CCCTTCTCAG TGGCTTCTCT TGCCTATGCT TCCTCCCCAG
50101 GGCCAGGTTT GAGAACATCC CCATGAAGTC CTGACCTGTC TTTTATCCTA
```

FIGURE 3-17

```
50151 CCAGGACAAG ACTGTGGTGG TGGCAGACTT TGGGCTGTCA CGGCTCATAG
50201 TGGAAGAGAG GAAAAGGGCC CCCATGGAGA AGGCCACCAC CAAGAAACGC
50251 ACCTTGCGCA AGAACGACCG CAAGAAGCGC TACACGGTGG TGGGAAACCC
50301 CTACTGGATG GCCCCTGAGA TGCTGAACGG TGAGTCCTGA AGCCCTGGAG
50351 GGGACACCCG CAGAGGGAGG ACAGATGCTG CCCTTGCATC AGAGCCCTGG
50401 GAATTCCAGG GGAGGCCTGT GAAGCGTAGG ACCGGATACC CAGAGCTGAG
50451 GATATTTTTC CCTTGCCAGG TGGGGCCTCA CGATTTAGCT CCTGAGCTCA
50501 GGGGGCTGGG AACTGATCAG TGTCCCATCA TGGGGATAA GGTGAGTTCT
50551 GACTGTGGCA TTTGTGCCTC AGGGATCGCT AAGAGCTCAG GCTATTGTCC
50601 CAGCTTTAGC CTTCTCTCTC CATGGTGAGA ACTGAAGTGT GGTGCCCTCT
50651 GGTGGATAAT GCTCAAACCA ACCAGAGATG CTGGTTGGGA TTCTTGAAAT
50701 CAGGGTTGTG AGGCCTCAGA AATGGTCTGA ATACAATCCA TTTTGGAGTC
50751 TGAGGCCCAG AGAAGTTCAG TGAATTGCCT AGGAGCATAC AGCTGCCTAA
50801 TGGCAGAGGC TAGATGAACC CTAGTCTGGT TCTTTTCCAC TTTAACGTGC
50851 AGTTTCATCC TAGGCAGTGT TATGTTATAA GGGCTCTCCA AGGCAGTTCA
50901 CCTACGGCTG AGGAAGGACT ATTTTCAGGT GGTGTCTGCG CAGGACAGCC
50951 TGTGGGGTGT CCCTACAGAA CCTGTTCTAG CCCTAGTTCT TAGCTGTGGC
51001 TTAGATTGAC CCTAGACCCA GTGCAGAGCA GGTAAGGGAT GTAAACTTAA
51051 CAGTGTGCTC TCCTGTGTTC CCCAAGGAAA GAGCTATGAT GAGACGGTGG
51101 ATATCTTCTC CTTTGGGATC GTTCTCTGTG AGGTGAGCTC TGGCACCAAG
51151 GCCATGCCCG AGGCAGCAGG CCTAGCAGCT CTGCCTTCCC TCCGAACTGG
51201 GGCATCTCCT CCTAGGGATG ACTAGCTTGA CTAAAATCAA CATGGGTGTA
51251 GGGTTTTATG GTTTATAACG CATCTGCACA TCTTTGCCAC GTTCGTGTTT
51301 CATTGGTCTT AAGAGAAGGA CTGGCAGGGT TTTTTTGTTT TAGATGGAGC
51351 CTCACTTCGT TGCCCAGGCT GGAGTGCAGT GGCACAATCT GGGCTCACTG
51401 CAACCTCTGC CTTCTGGGTT CAAGTGATTC TCCTGCCTCA GCCTCCCAAG
51451 TAGCTGGGAC TACCGGCACA CACCACCATG CCCGGCTAAT TTTTGTATTT
51501 TTAGTAGAGA CAGGGTTTCA CCATGTTGGC CAGGCTGGTC TTGAACTCCG
51551 GACCTCAGGT GATCCGCCTG CCTCAGCCTC TAAAAGTGCT GGAATTAATA
51601 GGCGTGAGCT ACCTCGCCCG GCCAGGTTTT TTTTTTTTTT TTTTTAGTTG
51651 AGGAAACTGA GGCTTGGAAG AGGGCAGTGG CTTGCACATG GTCGATAAGG
51701 GGCAGATGAG ACTCAGAATT CCAGAAGGAA GGGCAAGAGA CTGTTCATGT
51751 GGCTGTCTAG CTAGCTCTTG GGCCAAATGT AGCCCTTCTC AGTTCCCTTC
51801 AAGTAGAAGT AGCCACTCTA GGAAGTGTCA GCCCTGTGCC AGGTACCACG
51851 TGGACAGAGT GAGGAATCTT GGAAAGATTC CTACCTTTAG GAGTTTAGTC
51901 AGGTGACAGC ATATCTCAGC GACTCAAACA CACACACATT CAAAGCCTTC
51951 TGTAATTCCT ACAAAGTTGT GAGGGGTAGA GGAGAGGAGA GACAAGGGAT
52001 GGTTAGGATA ATGAAGGAAT GTTTTGTTTT TGTTTTTGTT TTTGAGATGG
52051 AGTTTCACTC TGTCACCCAG GCTGGAGTGC AGAGGTGCAA TCTTGGCTCA
52101 CTGCAGCCTC CGCCTCCCAG GTTCAAGCAA TCCTCCTGCC TCAGCCTCCC
52151 AAGTAGCTGG GACTACAGGT GTGCGCCACC ACGCCTGGCT AATTTTTGTA
52201 TTTTCAGTAG AGACAGGGTT TCGCCATATT GGCCAGGCTG GTCTCAAATG
52251 CCTGACCTCA GGTGATACAC CCGCTTCAGC CTCCCAAAGT GCTGAGATTA
52301 CAGGCATGAG CTACCGTGCC TGGCCATGAA GGAAGATTTG TTTTAAAAAA
52351 TTGTTTTCTT TAATATTAAT TGAACACCTC TGTTCAGAGC ACTGGGCTGG
52401 TGCCAGAGGG TTTCAGACAT GAATCAGATC CAGCACCTCA TAGAGCCTTA
52451 ATCTGGCACA CACACACAGC CACAAGGAGA CACAGACAAG GCAGGGTAGG
52501 ATGAGTGGAA GCTAGGAGCA GATGCTGATT TGGAACACTT GGCTTCTGCA
52551 GTGAAGCCCC TTCTTAGTCC TCTTCAGTAA CCCAGCTCTC AGTGGATACA
52601 GGTCTGGATT AGTAAGATTT GGAGAGATGA TTGGGGATTG GGGAGAGCTC
52651 TCTAACCTAT TTACCACCT CCTCTTCTGC CATTCTTCCT GTCCACATCC
52701 CCAGCATCCC TTTCCCTTGC CAAGTATCTG TGGCCTCTGT AGTCCTTTGT
52751 AAACAGCTGT CTTCTTACCC TACAGATCAT TGGGCAGGTG TATGCAGATC
52801 CTGACTGCCT TCCCCGAACA CTGGACTTTG GCCTCAACGT GAAGCTTTTC
52851 TGGGAGAAGT TTGTTCCCAC AGATTGTCCC CCGGCCTTCT TCCCGCTGGC
52901 CGCCATCTGC TGCAGACTGG AGCCTGAGAG CAGGTTGGTA TCCTGCCTTT
52951 TTCTCCCAGC TCACAGGGTC CTGGGACGTT TGCCTCTGTC TAAGGCCACC
53001 CCTGAGCCCT CTGCAAGCAC AGGGGTGAGA GAAGCCTTGA GGTCAAGAAT
53051 GTGGCTGTCA ACCCCTGAGC CATCTGACAA CACATATGTA CAGGTTGGAG
```

FIGURE 3-18

```
53101 AAGAGAGAGG TAAAGACATA GCAGCAAGTA ATCTGGATAG GACACAGAAA
53151 CACAGCCATT AAAAGAAAGT TTAAAAGAAG GAAATTCACC CAAACCATTT
53201 GAATACAGTA AGTGTATTCA TCTTTCGATA TTCCCCTGTC CATATCTACA
53251 CATATACTTT TTTTTATAGT AAATAGTTCT GTATTTTGCC CTGCATTTCC
53301 CTTGTGTTTA CTATCCAGTC TTCCTGTTTA TCATTTTTGT CGACAACATG
53351 AAATTCTATT GAGAGACTGT CTGAACATAT TGTAATGTAG ATGTTCAGGT
53401 TTTTCCAGTT TCTCTTTACA ATAGGTATTT AACTACAGTG AGCAGTTTTA
53451 TGCATTTAGC TAATTTCTCC TTTGAGGAAG TATTTTCAAA ATTACCTTTA
53501 TTCTTCTCAG GTAATAATTT CATTATTACC AAAGTTACCC TAGGTCTTTT
53551 CAAGTGTGTG GTTAAAAAAC GAGAATCTGG CTGGGCGCGA TGGCTCACAC
53601 CTGTAATCCC AGCACTTTGG GAGGCTGAGG CTGGTGGATC ACCTGAGGTC
53651 TGGAGTTCGA GACCAGCCTG GCCAACATGG TGAAACCCCA TCTCTACTAA
53701 AAATACAAAA CTTAGCCAGG CATGGTGGCA GGTGCCTGTA ACCCCAGCTA
53751 CTTGGGAGGC TGAGGCAGGA GAATTGCTTG AACCCAGGGG CGGAGGTTGC
53801 AGTGAGCCGA TATCACGCCA TTGCACTCCA GCCTCGGCAA CAAGAGTGAA
53851 ACTCTGTCTC AAAAATGGGG TTCTTTTCCT GCCATCAAAA ATCATGTTTC
53901 TTTTAAAAAC AAGTTCAAAC ATTACCAAAG TTTATAGCAC AGGAAATACG
53951 TCTTCTGTAA TCTCCCTTAA CCAATATATC CCTCAACATT CTCCTCACCC
54001 CCAACTCCAC CCTCCCAGGA TAACCAGTTG GGACATAATC TTTATTTAAA
54051 AATGGTTTCC GGATAGAGAA AGCGCTTCGG CGGCGGCAGC CCCGGCGGCG
54101 GCCGCAGGGG ACAAAGGGCG GCGGATCGG CGGGGAGGGG GCGGGGGCG
54151 ACCAGGCCAG GCCCGGGGGC TCCGCATGCT GCAGCTGCCT CTCGGGCGCC
54201 CCCGCCGCCG CCCTCGCCGC GGAGCCGGCG AGCTAACCTG AGCCAGCCGG
54251 CGGGCGTCAC GGAGGCGGCG GCACAAGGAG GGGCCCCACG CGCGCACGTG
54301 GCCCCGGAGG CCGCCGTGGC GGACAGCGGC ACCGCGGGGG GCGCGGCGTT
54351 GGCGGCCCCG GCCCCGGCCC CCAGGCCAGG CAGTGGCGGC CAAGGACCAC
54401 GCATCTACTT TCAGAGCCCC CCCCGGGGCC GCAGGAGAGG GCCCGGGCTG
54451 GGCGGATGAT GAGGGCCCAG TGAGGCGCCA AGGGAAGGTC ACCATCAAGT
54501 ATGACCCCAA GGAGCTACGG AAGCACCTCA ACCTAGAGGA GTGGATCCTG
54551 GAGCAGCTCA CGCGCCTCTA CGACTGCCAG GAAGAGGAGA TCTCAGAACT
54601 AGAGATTGAC GTGGATGAGC TCCTGGACAT GGAGAGTGAC GATGCCTGGG
54651 CTTCCAGGGT CAAGGAGCTG CTGGTTGACT GTTACAAACC CACAGAGGCC
54701 TTCATCTCTG GCCTGCTGGA CAAGATCCGG GCCATGCAGA AGCTGAGCAC
54751 ACCCCAGAAG AAGTGAGGGT CCCCGACCCA GGCGAACGGT GGCTCCCATA
54801 GGACAATCGC TACCCCCCGA CCTCGTAGCA ACAGCAATAC CGGGGGACCC
54851 TGCGGCCAGG CCTGGTTCCA TGAGCAGGGC TCCTCGTGCC CCTGGCCCAG
54901 GGGTCTCTTC CCCTGCCCCC TCAGTTTTCC ACTTTTGGAT TTTTTTATTG
54951 TTATTAAACT GATGGGACTT TGTGTTTTTA TATTGACTCT GCGGCACGGG
55001 CCCTTTAATA AAGCGAGGTA GGGTACGCCT TTGGTGCAGC TCAAAAAAAA
55051 AAAAAAAAAT GATTTCCAGC GGTCCACATT AGAGTTGAAA TTTTCTGGTG
55101 GGAGAATCTA TACCTTGTTC CTTTATAGGC CAAGGACCGC AGTCCTTCAG
55151 TAACACCAGT GTAAAAGCTT GAGGAGAAAT TGTGAAGCTA CACAGTATTT
55201 GTTTTCTAAT ACCTCTTGTC ATTCTAAATA TCTTTAATTT ATTAAAAAAT
55251 ATATATATAC AGTATTGAAT GCCTACTGTG TGCTAGGTAC AGTTCTAAAC
55301 ACTTGGGTTA CAGCAGCGAA CAAAATAAAG GTGCTTACCC TCATAGAACA
55351 TAGATTCTAG CATGGTATCT ACTGTATCAT ACAGTAGATA CAATAAGTAA
55401 ACTATATTGA ATATTAGAAT GTGGCAGATG CTATGGAAAA AGAGTCAAGA
55451 CAAGTAAAGA CGATTGTTCA GGGTACCAGT TGCAATTTTA AATATGGTCG
55501 TCAGAGCAGG CCTCACTGAG GTGACATGAC ATTTAAGCAT AAACATGGAG
55551 GAGGAGGAGT AAGCCTGAGC TGTCTTAGGC TTCCGGGGCA GCCAAGCCAT
55601 TTCCGTGGCA CTAGGAGCCT GGTGTTTCCG ATTCCACCTT TGATAACTGC
55651 ATTTTCTCTA AGATATGGGA GGGAAGTTTT TCTCCTATTG TTTTTAAGTA
55701 TTAACTCCAG CTAGTCCAGC CTTGTTATAG TGTTACCTAA TCTTTATAGC
55751 AAATATATGA GGTACCGGTA ACATTATGCC CATTTCTCAC AGAGGCACTA
55801 CTAGGTGAAG GAGTTTGCCT GACGTTATAC AACCAGGAAG TAGCTGAGCC
55851 TAGATCCCTT CCACCCACCC CATGGCCCTG CTCATGTTCC ACCTGCCTCT
55901 AATTTACCTC TTTTCCTTCT AGACCAGCAT TCTCGAAATT GGAGGACTCC
55951 TTTGAGGCCC TCTCCCTGTA CCTGGGGGAG CTGGGCATCC CGCTGCCTGC
56001 AGAGCTGGAG GAGTTGGACC ACACTGTGAG CATGCAGTAC GGCCTGACCC
```

FIGURE 3-19

```
56051 GGGACTCACC TCCCTAGCCC TGGCCCAGCC CCCTGCAGGG GGGTGTTCTA
56101 CAGCCAGCAT TGCCCCTCTG TGCCCCATTC CTGCTGTGAG CAGGGCCGTC
56151 CGGGCTTCCT GTGGATTGGC GGAATGTTTA GAAGCAGAAC AAGCCATTCC
56201 TATTACCTCC CCAGGAGGCA AGTGGGCGCA GCACCAGGGA AATGTATCTC
56251 CACAGGTTCT GGGGCCTAGT TACTGTCTGT AAATCCAATA CTTGCCTGAA
56301 AGCTGTGAAG AAGAAAAAAA CCCCTGGCCT TTGGGCCAGG AGGAATCTGT
56351 TACTCGAATC CACCCAGGAA CTCCCTGGCA GTGGATTGTG GGAGGCTCTT
56401 GCTTACACTA ATCAGCGTGA CCTGGACCTG CTGGGCAGGA TCCCAGGGTG
56451 AACCTGCCTG TGAACTCTGA AGTCACTAGT CCAGCTGGGT GCAGGAGGAC
56501 TTCAAGTGTG TGGACGAAAG AAAGACTGAT GGCTCAAAGG GTGTGAAAAA
56551 GTCAGTGATG CTCCCCCTTT CTACTCCAGA TCCTGTCCTT CCTGGAGCAA
56601 GGTTGAGGGA GTAGGTTTTG AAGAGTCCCT TAATATGTGG TGGAACAGGC
56651 CAGGAGTTAG AGAAAGGGCT GGCTTCTGTT TACCTGCTCA CTGGCTCTAG
56701 CCAGCCCAGG GACCACATCA ATGTGAGAGG AAGCCTCCAC CTCATGTTTT
56751 CAAACTTAAT ACTGGAGACT GGCTGAGAAC TTACGGACAA CATCCTTTCT
56801 GTCTGAAACA AACAGTCACA AGCACAGGAA GAGGCTGGGG GACTAGAAAG
56851 AGGCCCTGCC CTCTAGAAAG CTCAGATCTT GGCTTCTGTT ACTCATACTC
56901 GGGTGGGCTC CTTAGTCAGA TGCCTAAAAC ATTTTGCCTA AAGCTCGATG
56951 GGTTCTGGAG GACAGTGTGG CTTGTCACAG GCCTAGAGTC TGAGGGAGGG
57001 GAGTGGGAGT CTCAGCAATC TCTTGGTCTT GGCTTCATGG CAACCACTGC
57051 TCACCCTTCA ACATGCCTGG TTTAGGCAGC AGCTTGGGCT GGGAAGAGGT
57101 GGTGGCAGAG TCTCAAAGCT GAGATGCTGA GAGAGATAGC TCCCTGAGCT
57151 GGGCCATCTG ACTTCTACCT CCCATGTTTG CTCTCCCAAC TCATTAGCTC
57201 CTGGGCAGCA TCCTCCTGAG CCACATGTGC AGGTACTGGA AAACCTCCAT
57251 CTTGGCTCCC AGAGCTCTAG GAACTCTTCA TCACAACTAG ATTTGCCTCT
57301 TCTAAGTGTC TATGAGCTTG CACCATATTT AATAAATTGG GAATGGGTTT
57351 GGGGTATTAA TGCAATGTGT GGTGGTTGTA TTGGAGCAGG GGGAATTGAT
57401 AAAGGAGAGT GGTTGCTGTT AATATTATCT TATCTATTGG GTGGTATGTG
57451 AAATATTGTA CATAGACCTG ATGAGTTGTG GGACCAGATG TCATCTCTGG
57501 TCAGAGTTTA CTTGCTATAT AGACTGTACT TATGTGTGAA GTTTGCAAGC
57551 TTGCTTTAGG GCTGAGCCCT GGACTCCAG CAGCAGCACA GTTCAGCATT
57601 GTGTGGCTGG TTGTTTCCTG GCTGTCCCA GCAAGTGTAG GAGTGGTGGG
57651 CCTGAACTGG GCCATTGATC AGACTAAATA AATTAAGCAG TTAACATAAC
57701 TGGCAATATG GAGAGTGAAA ACATGATTGG CTCAGGGACA TAAATGTAGA
57751 GGGTCTGCTA GCCACCTTCT GGCCTAGCCC ACACAAACTC CCCATAGCAG
57801 AGAGTTTTCA TGCACCCAAG TCTAAAACCC TCAAGCAGAC ACCCATCTGC
57851 TCTAGAGAAT ATGTACATCC CACCTGAGGC AGCCCCTTCC TTGCAGCAGG
57901 TGTGACTGAC TATGACCTTT TCCTGGCCTG GCTCTCACAT GCCAGCTGAG
57951 TCATTCCTTA GGAGCCCTAC CCTTTCATCC TCTCTATATG AATACTTCCA
58001 TAGCCTGGGT ATCCTGGCTT GCTTTCCTCA GTGCTGGGTG CCACCTTTGC
58051 AATGGGAAGA AATGAATGCA AGTCACCCCA CCCCTTGTGT TTCCTTACAA
58101 GTGCTTGAGA GGAGAAGACC AGTTTCTTCT TGCTTCTGCA TGTGGGGGAT
58151 GTCGTAGAAG AGTGACCATT GGGAAGGACA ATGCTATCTG GTTAGTGGGG
58201 CCTTGGGCAC AATATAAATC TGTAAACCCA AAGGTGTTTT CTCCCAGGCA
58251 CTCTCAAAGC TTGAAGAATC CAACTTAAGG ACAGAATATG GTTCCCGAAA
58301 AAAACTGATG ATCTGGAGTA CGCATTGCTG GCAGAACCAC AGAGCAATGG
58351 CTGGGCATGG GCAGAGGTCA TCTGGGTGTT CCTGAGGCTG ATAACCTGTG
58401 GCTGAAATCC CTTGCTAAAA GTCCAGGAGA CACTCCTGTT GGTATCTTTT
58451 CTTCTGGAGT CATAGTAGTC ACCTTGCAGG GAACTTCCTC AGCCCAGGGC
58501 TGCTGCAGGC AGCCCAGTGA CCCTTCCTCC TCTGCAGTTA TTCCCCCTTT
58551 GGCTGCTGCA GCACCACCCC CGTCACCCAC CACCCAACCC CTGCCGCACT
58601 CCAGCCTTTA ACAAGGGCTG TCTAGATATT CATTTTAACT ACCTCCACCT
58651 TGGAAACAAT TGCTGAAGGG GAGAGGATTT GCAATGACCA ACCACCTTGT
58701 TGGGACGCCT GCACACCTGT CTTTCCTGCT TCAACCTGAA AGATTCCTGA
58751 TGATGATAAT CTGGACACAG AAGCCGGGCA CGGTGGCTCT AGCCTGTAAT
58801 CTCAGCACTT TGGGAGGCCT CAGCAGGTGG ATCACCTGAG ATCAAGAGTT
58851 TGAGAACAGC CTGACCAACA TGGTGAAACC CCGTCTCTAC TAAAAATACA
58901 AAAATTAGCC AGGTGTGGTG GCACATACCT GTAATCCCAG CTACTCTGGA
58951 GGCTGAGGCA GGAGAATCGC TTGAACCCAC AAGGCAGAGG TTGCAGTGAG
```

FIGURE 3-20

```
59001 GCGAGATCAT GCCATTGCAC TCCAGCCTGT GCAACAAGAG CCAAACTCCA
59051 TCTCAAAAAA AAAAA  (SEQ ID NO:3)
```

FEATURES:
Start:   3000
Exon:    3000-3044
Intron:  3045-45393
Exon:    45394-45525
Intron:  45526-45761
Exon:    45762-45818
Intron:  45819-50154
Exon:    50155-50329
Intron:  50330-51076
Exon:    51077-51132
Intron:  51133-52775
Exon:    52776-52933
Intron:  52934-55922
Exon:    55923-56064
Stop:    56065

CHROMOSOME MAP POSITION:
Chromosome 22

ALLELIC VARIANTS (SNPs):
DNA

| Position | Major | Minor | Domain |
|---|---|---|---|
| 941 | A | T | Beyond ORF(5') |
| 2612 | G | A | Beyond ORF(5') |
| 5080 | G | A | Intron |
| 6599 | - | A C | Intron |
| 6983 | C | G | Intron |
| 9885 | A | - | Intron |
| 12538 | G | T | Intron |
| 17707 | T | C | Intron |
| 18219 | - | A | Intron |
| 19670 | C | T | Intron |
| 21153 | G | T | Intron |
| 24566 | C | - | Intron |
| 26604 | G | A | Intron |
| 27255 | C | G | Intron |
| 27399 | T | C | Intron |
| 28088 | G | A | Intron |
| 28734 | G | A | Intron |
| 29246 | - | T | Intron |
| 29490 | G | A | Intron |
| 29934 | T | C | Intron |
| 34480 | A | G | Intron |
| 38812 | T | C | Intron |
| 40731 | C | G | Intron |
| 41303 | T | A | Intron |
| 41305 | - | A | Intron |
| 41457 | G | C | Intron |
| 43168 | A | - T | Intron |
| 43357 | T | G | Intron |
| 45664 | T | C | Intron |
| 47549 | A | C | Intron |

FIGURE 3-21

| | | | |
|---|---|---|---|
| 47908 | C | A | Intron |
| 52267 | C | A | Intron |
| 54654 | T | C | Intron |
| 54679 | C | G | Intron |
| 54693 | A | C | Intron |
| 54706 | T | C | Intron |
| 54712 | T | C | Intron |
| 54799 | T | C | Intron |
| 54819 | G | A | Intron |
| 55499 | C | T | Intron |
| 56825 | C | A | Beyond ORF(3') |
| 58871 | T | A | Beyond ORF(3') |

Context:

DNA
Position

941
GAGTAAGTGGGTGGTCAGGTTACAGACTTAATTTTGGGTTAAAAAAGTAAAAACAAGAAAC
AAGGTGTGGCTCTAAAATAATGAGATGTGCTGGGGGTGGGGCATGGCAGCTCATAAACTG
ACCCTGAAAGCTCTTACATGTAAGAGTTCCAAAAATATTTCCAAAACTTGGAAGATTCAT
TTGGATGTTTGTGTTCATTAAAATCTCTCACTAATTCATTGTCTTGTCCACTGTCCGTAA
CCCAACCTGGGATTGGTTTGAGTGAGTCTCTCAGACTTTCTGCCTTGGAGTTTGTGAGAG
[A,T]
GATGGCATACTCTGTGACCACTGTCACCCTAAAACCAAAAAGGCCCCTCTTGACAAGGAG
TCTGAGGATTTTAGACCCAGGAAGAATGAGTGATGGGCATATATATATCCTATTACTGAG
GCATGAGAAGAGTGGAATGGGTGGGTTGAGGTGGTGTTTTAAGGCCTCTTGCCAGCTTGT
TTAACTCTTCTCTGGGGAACGAGGGGGACAACTGTGTACATTGGCTGCTCCAGAATGATG
TTGAGCAATCTTGAAGTGCCAGGAGCTGTGCTTTGTCTATTCATGGCCCCTGTGCCTGTG

2612
TGAGTTGGAACAGTTTTGATACCAAAACCATCCCCCCGCCCCCCAACCCCCAGCCTAGGGT
CCGTGGAAAAATTGGCCCCTGGTGCCAAAAAGGTTGAGGACTGCTGATCTAGAGGACCAA
TTTATTCAATGTTGGTTGAGTAAATGAGCTCTTGGATTAGGTGATGGAAAAATCTGAAAA
AACAGGGCTTTTGAGGAATAGGAAAAGGCAGTAACATGTTTAACCCAGAGAGAAGTTTCT
GGCTGTTGGCTGGGAATAGTCATAGGAAGGGCTGACACTGAAAAGAAGGAGATTGTGTTC
[G,A]
TTTCTTCTTCTCAGAGCTATAAGCAAAGGCTGAAAGTTCTAGAAAAAGGCAAGTTTTGTT
TCAGTAGAAAAAAGGATAATCAGAACCATTTTTAGAAAATGGAATGAGACTACTTTTGAG
GCCATGAGTTCCTTGTCCCTGGAGAGATGAGCAGAGGTTGGACAAGTGCTTACCAGAGAT
CTTGTGGAGGCAGAAACTGTGCATCTAGCAGAGCATTGGCCTAACCCTTTCAAATGAGAT
GCTGTTAACTCAGTCTTATTCTACATGGTAGGAATCCTGTCCCTTTGCCTCCTGCTACTT

5080
ACAACGTAAAATAGTTGAAATTTGTTGGTGGAAAGAAGAGCAGTCCACTCCAGAGGCTGG
ATGGGCATGCCTGGCCCCCAAGGTCTGAAGTGGTAGGGCTGTGCCTATATCCTGAGAATG
AGATAGACTAGGCAGGCACCTTGTGCTGTAGATTCCAGCTCCTGCACATAGCTCTTGTTG
TAAAACATCCCTGTGCTTATACCAAGTAATTGAGTTGACCTTTAAACACTTGCCTCTTCC
CTGGGAACCATATAGGGGATTGGCCTGGAGACGTCTGGCCTCTGGAAGAGTTGGAAAGCA
[G,A]
CCATCATTATTATCCTTTTCCTTTCAGCTATAACTCAGAGCTCTCAAGTCTTTTCTGTGGA
TCTTATTGCCTTGGTTCTTGCCCCTTTTACTCCCAGGGAAGTTGATTCTGTCTTTTCTGT
TCCATTTAGTATGACAGGAGCAGAGAATGTCAGAGCTGTAAGGGACCTTATAGTTAAAGC
CTTTGGCTGGTCCTTTCATTTTATAGCTGGGACTAATAAGTAACGTCAAAACCCAATGAG
TTCACAGATTGGGTCTCGCCTTGGCATGTAACCCATATGTTCATATTCTTGCTGTTTTCC

6599
CTGTAATCCTAGCACTCTGGGAGGCCGAGGCAGAAGGATCGCTTGAGCCCATGAGCCCAG
GAGTTTGAGACCAGCCTGGCCAACATGGCAAAACTCCACCTCTACAAAAAATACAAAAAT
ATTAGCCAGGCGTGATGGCACACACCTGTAGTCCCAGCTACTTGGGAAGCTGAGGAGCGA
TGATTACCTGAGCCCAGGGATATCAAGGCTGTAGTGAGCTGTGATCATGCCACTGTACTC
CATCCAGCTGGGGGACAGAGTGAAACCCCTGTCTCAAAACAAAACAAATGAAAAAAAAAA
[-,A,C]

FIGURE 3-22

```
         CCTTAATAATCAGTAACTGTCACTTTATATTATGTTGTGAGTGTGTGTCTATATACACCT
         ATATGTATACATTTCTCTTATTACACATTCATTGGTGATCTGATGTGGAGCCCCAGGGAT
         TAAGGGCAACTTTGAACTACCCTGACACAATCAAGCCAAATATCATTCCCGTGGAGGAAG
         TAGAGTATCTAGGTTCTGTCTCCTAGTTGCAGCTTTACCTTGAGGACAGAGACTCTAATC
         CAGCTGTGCTGAAGGAGCACATCTCCTGACTTCTGAGCTTTCCCCTGGTAAATTCAAACT

6983   CACATTCATTGGTGATCTGATGTGGAGCCCCAGGGATTAAGGGCAACTTTGAACTACCCT
         GACACAATCAAGCCAAATATCATTCCCGTGGAGGAAGTAGAGTATCTAGGTTCTGTCTCC
         TAGTTGCAGCTTTACCTTGAGGACAGAGACTCTAATCCAGCTGTGCTGAAGGAGCACATC
         TCCTGACTTCTGAGCTTTCCCCTGGTAAATTCAAACTGGATGTCACGGCGCCCTCAGATA
         GAGCCTGGTAATTTGCCCTGGGGAGAGTGACTGTCTTTTGGATCTAATTTGACTTTTGCC
         [C,G]
         CAGTTGGAGGAAAATCTTCAGGGCTAGGAAGGATTGTATTTGTCTGACCCCAGAGATAAC
         CTGGGTTTTGAGGAACATGGGGCATCAACCTGAATGGTCTTGTAAGATCTCTCCCACGCC
         AGCTTGCCAGTGTTTCTCTGATGAATTTAGAGTACCTGAGTAGTGCAGGCCTGCTGGGAG
         GAGGACTCTCCCTCTGTGCTACTCAGAGAAATTCATTCTTCAAGGCCCCCTTCCAGCCTT
         GCTCTTACCCAGCTGGGCTACAGTTACAATAAAGGAAATGACTTTTCTTCTCCCCTTCCC

9885   GGCGTGCCACCACACCTTGCCATTTTTTTTTATTTTAAGTAGAAACAAGGTCTTATTAAT
         ACTATGTTGCCCAGGCTGGTCTTGAACTCCAGCGATCCTCCTGCCCCAGCCTCCCAAAGT
         GCTTGGGATTACGGAAGTAAGCCACTGTGCCTGGCCAGTGCAACCCCCATTTTATACTAA
         AACAGGAAGGCCCAGAAAGGTTTGGAGTAACTTGTCCAGGGTCACACAGATGATATTTGA
         ACTCAGGTCTCCCTGGCTCCCAAGAGAGTCTGCTTTCCACTAGGACTCCCAGGAGAAAAA
         [A,-]
         AAAAAAAAAAAACAGTAGACTTGGAGACAGAAAATCTGATTTGAGTCTTAGTTGAGCTAGG
         CTAACTGTGTAACTGTGGGCAAGTTCCTTAGCCCCTGTGAGCCTCAGTTTCTTATCTGTA
         AAATGTCATAAAAGAAATCCATCTCATGGAGTAGTTGTGATGATCAAGGACTCTGAAAAC
         ATTAGAATGGTTTAATGTGAAGGATTAGCAGCAGCACATGGCAACATTGTGCATCTTATA
         TTAACTATCCAAATATATCAAGCGTCATTTGCTATATATAAAAGTCATCAAATTAGGCAC

12538   ACTTGGGAGGCTGAGGCAGGAGAATCACTTGAACCTGGGAGGCAGAGGTTGCAGTGAGCC
         CAGATCACGCCACTGCACTCCAGCCTGGTGACAGAGTAAGACTCCATCTCAAAAAAAAAA
         AAAAAAAAAAAAATTCCTTAATTTTGGCCTACAGTAGAGCCCTCCGTAATGTGGCCTCTCT
         CCACATCTCCACAACCTCCTGCTCCCTGCACTTCAGCCTCACCTCTCTTCTGGACAGGCC
         CTCCTTCTGACAAGGGCTTTGTTCATTCTGCTCCCTCTGCCTAGAATGCCCCCTTACTCT
         [G,T]
         TTCACTTAACTCCTGCTTATCGTTTAGATCTTTACCTGGATGGCTCAGAGAAATATAGAA
         GTAATTCCTCACCCTGAAAAATAGGTTAGGTCCCTGTTTTATGTTTTCATAGACCTTTCC
         TTTGAGGCTTTTTTTTAAAAAAGTAGTTTTAATCTCACATTTATTCATGTGATCATCTCCT
         TAATGATATCTTAAGACCTCTAATAGAACAATTTGGTCATGGACTGTGGGGTTTTTGCCC
         CTCATTGTGTCAGCACTGAGCATAT.TGTTGGCATAGGAGGGATATTTGTTGAATGAATTG

17707   GTAGTGGGTGCTCAGAGTGTTTGCTGGGTGAATGATGTATTTGTTGAACGACTCTTTGGA
         CACTTGAATAAAGTCCATCCAGTATGCACCATTACCATCTCTTCGCTCTACAATATTCTT
         TTAGGCAAGAGCTTATCTTTTGAGGTGATAAGATAAGCTCAAACTTATGTAGACTAAGAC
         CTCAGTCTGTAAATGTCATCCCTAAGTCTTAAACCATCAAAACCAGGGCCTCAAGGAATG
         GCATGCCTTCTGCAACTGTAGCAACCTGCTGTGCTTATTTTGCCGTGTTTTTCATTTTTC
         [T,C]
         CCCAAAAGCTAGAGTCCCTTCTCCCATGGGCAGTGCTGGAAGTGTGCTAACAAATTCTTT
         CTCCATACTGCTTACGATTACAAAAAAAAACCCTCAGCATCTCATGCCAGACTTGAGTTAA
         GGTTGTTTTCTTTTGTGTGTCAGCTGTATTCTGGTCATGACTTCCTGATGATGCCCTATA
         GAGATTTTGCTGAGATCAGAGGGTGCTCCACTGCCATCAGTAGCACTGACTCTTGCAGAA
         GCACCGTTTCTGAAGTTGGCTAATGTCATCCCTCACGTTTGTTTGTTTGAAATTTGTTTT

18219   TGCCATCAGTAGCACTGACTCTTGCAGAAGCACCGTTTCTGAAGTTGGCTAATGTCATCC
         CTCACGTTTGTTTGTTTGAAATTTGTTTTAGTTCCAGAGATAGCACTTTCATGGAATGAC
         GCTATCTTCTAGAATCACTTTTTTTTTTTTTTTTGAGTTGGAGTCTCGCTGTGTCGCCAGG
         CTGGAGTGCAGTGGCACAATCTCAGCTCACTGCAATCTCCACCTTCCGGGTTCAAGTGAT
         TCCCCTGCCTCAGCCTCCCGAGGAGCTGTTACTACAGGCGCACACCCCCACTCCTGGCTA
```

FIGURE 3-23

```
         [-,A]
         TTTTATGTGTTTTAGTAGAGACGGGGTTTCACCGTGTTGGCCAGGATGGTCTCGATCTCC
         TGACTTTGTGATCTGCCTGCTTCAGCCTCCCAAAGTGCTGGGATTACAGGTGTGAGTCAC
         CGCGCCTGGCCTAGAATCACCTTTTTATACCATAACGTGAGCACCACTGCCGCGTCACCA
         AGGAAAGAGAGAGGCAGCTACTGTGGGGTTACAAATGGGTAAGAGTGGCACCAGGAAGGT
         GAAAGTCTCTACTTAGCCAAGGCTTAACAAAATGTCAATCACCAAACATTTATTTATTAA

19670    GACCCCCATGATGAGCAACTATAGCACTAGAACAGTGATAATAACTAATGTTTATAATGC
         ATCTTCAGTTTACAGAGGGCTTTTGTACTCATCATCTAGTTTAGTTCCTGCAACAACCTC
         TTGAGGAATATAGCACAAGCAGGACAAGGGAAGCCCAGAGATGTTAAATAATTTATCCAA
         GTTTATGCTGCTGGGAAGGGCAGCACTGAAATTAAAAGAAAAGTTTTCTGAGCTCAAATC
         CCATGCCCTTTCCTCAATGTGAGCTCTAGCAAGGTATTCAGGAATCCTGCCTCTACAGTT
         [C,T]
         AGAGCCTCAAATTGCTGGGTATGTTGAGTTCTTGTATCTGATTTTTCTAGATTTCCTGCC
         CACATTCTTACTGTCTGGATATCAGGAAAGAGTTTATCAAATGCCTGTGGAAATCCAAGA
         TAAGGTCTCATGATGAGTAACCCAGTGAAAACATGAAGTCAAGTCTAACTAGTCACTACT
         ATTTCACTACTGCTGACTCCTGATGATCAGCTCCTTTTCTAAGTGCTTACTGTCCACTTA
         TTCCATCATCTGCCTAGAATTTATGTGAAGGAATCAAAGCAAAAGGATCATAAGGCTTCC

21153    GGACCCTTGTTTTAGAAGGATGACTGCTGCTATAATGTAGAAAGTGATTTGGAAGAGGGG
         AGGAGTGGGGCACGAAAGATGGTTAGTAGATGGGGGTGGTAATGCTTACCTTTCAGTATT
         TGGAGGCTTCGGAGTCCTCAAAAATTCTCTTCCTTGATTGGAGTCCTCCCAGCCAATAGA
         GGGCTTCACACAAACAGTTTCTTGGGTTTTGAATTGTTTGACCAGAGCTTTCTTCCGACA
         AAAGGTTGGGGTGATTCATTCACTTACCACACCTTGCCTGAACATTCACTTGGGGCTGCC
         [G,T]
         GTTATGAAGGCTATTGTTCTCCAGCCTGTCACAGACGCTTTGAAGACCTGTGCCTCAGCT
         GGTTCTAAGGAGTCAGTTTGTTCAGCTCCGTGCCAGGTTTCCAACTTATGAAATGTGCTG
         GAGATTAACACCTCTCCTGCCATTTTATCCCTACTATAATTGCCAGTCAAAGGATTCCTG
         CAGTTGCCTCTGGCAGCCATAACTGATGAATGTTCTGCCAGCTGCTCTGAGGACCTAGAA
         GAGCAGTTTTCTATCCAGGACCAGTTTCCAAGGGTGGGAGGGTGAAATATATCCTCCAGT

24566    CTACTCTGGAGGCTGAGGTGAGAGGATCACTTGAGTCCAGAAGGTCGAGGTCAAGATTGT
         AGTGAGCCATGATGGCATCACCGCACTCCAGCCTGAGTGACAGAGAGAGACCCTGACTCA
         AAAAAAAAAAAACAAAAAAAAAAAACACCCTCACCACTTATCAGCTATTTGTCTTGAGAA
         TAGTGACATAACCCCTCAGAACCTATTTCCTAATCTGTTAAATGAGGCTGATGACGTTTC
         CTCCTTTTACTGGCAATTTAAACATGATGGATAATAAATGCTAAGCACTTAACACAGGGC
         [C,-]
         TAGAAGATATTAACTGCTCAATAAATGGTAGCTTCTTAACAGTATTCAAACCCATGTGCT
         CTTATCACATGCATTGTTGTCCCTGTGTCCAGTTGGTGGAATGGGAAAAGGCTCCCTTGT
         AACCCCATCTACCATCTTTATCAGACTTTCCTGCCATGGTTCACAGTAAGAGATAGAAGC
         TGCACGGTGACTTCTGGCTCTTTACAATGGTGAGCGGTGTGTGCCTGGTAAGGGAGAGCT
         GATGTCACTGCCCCAAATCCAGTAGTGAGATCTGAGTGTTCTGGTTTCCTCCAGCAGCCT

26604    GATTTGCAGCTGAGCCTGTCTATCTGGTGTGGGAAGAAGATGGGGAGTTACTTGTCAGTC
         CCGGCTTACTTCACCTCCAGAGACCTGTTTCGGTGAGTTGGTCTCCGAGTTCCCCTCTCC
         ATCTCTCCTGGCCCCTGGTCCTGAGAGGAGGGTGGTCTCCCTAAATCTCCTTCTCACTTA
         GTCCTTTACCATCGGTTCTGCCGGGCAGAAGCCAGCGGAGGTTATACCCAAGGAGAATCG
         GCCTTGTGAGGTACCCCCATTATGTCCTGGAAGTGGTGAGGGGAGGGATATACCCAGAAG
         [G,A]
         AACTTCTTAGGGAGCTCCAGCTCCCCTTCTATCCCAGACAAACCTGAAGGAGCCTCCAAA
         AGATGCCACTGACCTGCCCATTGTAGATGTTACTGCTTCCGGGGGGAATAGCCCAAATAG
         AGTGCTGTTTCCAGCTCTCACATGTCTTACCTGCGGGCCATGCTGCCTGCCCAGGAATTT
         GTCCCAACAAGCAGGATGGGCAGGTTTTGCCAAACTGTGGAAACTGGCAAGTCCTGGGTG
         TGGGTAGCCTGGTACACAGTAGGCACCTTATAAACGTTTGTTCTCTTAATGGCAGGCACA

27255    TGGGGAAAGACCTGGGCGAGTGCTTCTAAGACTGGAGCAATGGGCTTTAGAGTGTTCCTG
         AGCTGCTGGGCCAGCCCCCACACCTCCTCAGTCCCTAGGCCTAAGTACCTCCACGAGCCT
         CTCTCTGTGGGCTTCTCAGAGGGAGATGTGGAAACTCTACCTCTAACCTGGCTTTCTTT
         GCTCATTGCCCCACTCCACCTCCCATAGAAACTCCCCAGGGGGTTTCTGGCCCTCTGGGT
```

FIGURE 3-24

```
            CCCTTCTGAATGGAGCCATTCCAGGCTAGGGTGGGGTTTGTTTTCATTCTTTGGGAGCAG
            [C,G]
            CTGTTGTTCCAAAAAGGCTGCCTCCCCCTCACCAGTGGTCCTGGTCGACTTTTCCCTTCT
            GGCTTCTCTAAGCTAGGTCCAGTGCCCAGATCTTGCTGCCGGGATACTAGTCAGGTGGCC
            AGGCCCTGGGCAGAAAAGCAGTGTACCATGTGGTTTTGTGGAATGACCGGACCCTGGTAG
            ATTGCTGGGAAGTGTCTGGACAGGGGGAAGGGGGAAGGGAACTGGTCCTCAATGCTGACT
            CTACCAAGCGCCCTGCTAGACACTTTATCCTTTAATCTCTCAACAGCCTAAAGAGATTAT

27399       AGATGTGGAAACTCTACCTCTAACCTGGCTTTCTTTGCTCATTGCCCCACTCCACCTCCC
            ATAGAAACTCCCCAGGGGGTTTCTGGCCCTCTGGGTCCCTTCTGAATGGAGCCATTCCAG
            GCTAGGGTGGGGTTTGTTTTCATTCTTTGGGAGCAGCCTGTTGTTCCAAAAAGGCTGCCT
            CCCCCTCACCAGTGGTCCTGGTCGACTTTTCCCTTCTGGCTTCTCTAAGCTAGGTCCAGT
            GCCCAGATCTTGCTGCCGGGATACTAGTCAGGTGGCCAGGCCCTGGGCAGAAAAGCAGTG
            [T,C]
            ACCATGTGGTTTTGTGGAATGACCGGACCCTGGTAGATTGCTGGGAAGTGTCTGGACAGG
            GGGAAGGGGGAAGGGAACTGGTCCTCAATGCTGACTCTACCAAGCGCCCTGCTAGACACT
            TTATCCTTTAATCTCTCAACAGCCTAAAGAGATTATATATCCCCATTTTACAGATGAGGC
            AACCAGTTTTCAACAGAGTTAACATATGGAGCCTCACTGGGCAGCTTTTTCTGTCTTCCTG
            ACTTTCTCTCATCCTTCAGGGGGCTGCAGGTTTGTTTTCTTCTCCTAGTGGAGAGGAAAT

28088       AAGAGCCAATGGAAATTGATCTTGAGTTTAGGAGAAAGCTTTTACATGTGGAATTAAGAT
            GCCAAGTGTTGAAGTAGCCACATTTCAGGTCCTCATTAATTTCTCTTAATCCTGGGAAGG
            CAGCTTAGGAGAAGGGTTGTTCCTTTAGGAGCCAGGAACTATACCCCTTTTACCCTTGGA
            GAGGCAGGGAAGCCAGGGAGGACACAACTTCTCAGGAAGAGGAGAAGCTAGAGCAGATAG
            TGAACTCTCAACCTGAACCTTTAAGGGCCAGACCACTAATGCCACCCAAGTCCACCTGCC
            [G,A]
            TTTGTCTTGTTCTGTCCCAGGCTTTCTGGAGAACCTGATCTTCTTGCCCCTACCCCCAAG
            CTCCGTTTGCCCAGCTAGAGTCTGGGGGGTACTGACTGACTTTCGTAGACATTCTTCCCT
            TCCCCAAATAAGAGGCCACATTCCTGAAGTCACTTCTGAAGAGATAGCTGCCACACAGGG
            CTCTTTCCCCCCAGGGAGGGACCACCCAGACCCTCTGCTCTCCCAGGTATCCGTTACCAC
            ATCACTACCTGGTCAGAAAGCTGTTTCTGCCATTAGCCCCTCCCTCTTTTATTATAGGAT

28734       AAGTAGAAGCTAGACTTCTTGGGCTCCTGAACAGGGTCCTTGCTGGATTCTGTGAAACAA
            ATTAAGTTCTTGACCCTAGGCCTCTGGGGGAGTACAAAGTCTATGGGAGTTCTGGGGCTG
            TGGTTGCAAGGAAAGTGACGCAACCAGATTCCATGGGGACATGATCAGGCGTGACATGTG
            AGGGAGGAAGAGGGAGCAAGGGAATGAAGAATACAACTTCTGTGTCCCATACACCCCTGC
            CTGACAGGCCATACATACTCAGCAGAGAATGCACTGTCTTTCCTACCACACTAGCGTGAG
            [G,A]
            AGTGAGCTGCAATTACCACTGTGCTTCCAAGTAAGAAAATACCTCAAATTGGAATTTACA
            AAAGAGGTAAATTAGGGAGTGGCTTTTGTCGGACATCTTTAAAGCATTTTTCTTTTTATA
            GAATTTCACTTAATGTCCAATACTGATTTAATGAGCTTGGGTTTACACATTATCTCTTGA
            AGAAAACAAATGAACCTTTGTGTTCCAAAGCAATCCATGTTTAAAGGGAAAAAATTATGC
            ATAACTCTGCCCAGCTTCACAGTAACCTTTGGCAGGTGCCTTAGGTCCTCTGGGACTCTT

29246       AATCCATGTTTAAAGGGAAAAAATTATGCATAACTCTGCCCAGCTTCACAGTAACCTTTG
            GCAGGTGCCTTAGGTCCTCTGGGACTCTTTTCCTTATCTGAAAAATGAAGGACTTGGATC
            AGGTGAATGGTTCCCAGCTCTGCAACTTATGTGGCTCCTCAGAGGCACACAAGCTCTTTT
            CCATTATTTGCCAAATAATGGAGGCCCTGTCTTTAACTGCAGTACAACTACACAAAATAC
            TTGAAACTACAGTCTTCCTGGTTTTTGGTTGGAACTGAATCAGTGCACTCTAGCAACACT
            [-,T]
            ATTTCTTGCTGTTCGTAGGCTTCATTATGTGTTTGGTTAATTTTTTAAAACAACAATAAC
            ATATTCCATAATAATTACAGCTTAATTGGCAGACTGTTTCAGTCTATAGGATCTGCAGGA
            AGGAGGAGTAATAAAGGGATTTTTGACTGAGCTCTTATGGAACAGAGTCTCTCTAGGCCC
            CTGTCATATCTGCCCTTCTGGGCCCTGGGAAAAGTTGGCATCCCCAGTTGTGGTGCTCT
            CCAGGTGCCCTCAGGCTGTGGTGGAGGGAGCTTCCCATTCTCTCCTTCAGCCCACTCAAT

29490       AACTACAGTCTTCCTGGTTTTTGGTTGGAACTGAATCAGTGCACTCTAGCAACACTTATT
            TCTTGCTGTTCGTAGGCTTCATTATGTGTTTGGTTAATTTTTTAAAACAACAATAACATA
            TTCCATAATAATTACAGCTTAATTGGCAGACTGTTTCAGTCTATAGGATCTGCAGGAAGG
```

FIGURE 3-25

```
         AGGAGTAATAAAGGGATTTTTGACTGAGCTCTTATGGAACAGAGTCTCTCTAGGCCCCTG
         TCATATCTGCCCTTCTGGGCCCTGGGGAAAAGTTGGCATCCCCAGTTGTGGTGCTCTCCA
         [G,A]
         GTGCCCTCAGGCTGTGGTGGAGGGAGCTTCCCATTCTCTCCTTCAGCCCACTCAATTCAG
         AGGCTAGGGGCTGAAAGAAGCTTCTCTACAACTGGCTGTTCACTGGGAGGTTAAGGGATG
         ACCATCCAGCCAGGCCTTCCTCAGGACATGGGAGGGCTTATGCTTTAACATGTGTAAATC
         CACTGCAATAATGACTGGTTCTTTTACCCCATAAGGTTGAGAATTTACCTGTAAACATTT
         TTGTCTGAAGAATTTGGATGTAAGTGAGGGCTGGGCCTCTATCTTATCTCACTTGGCTTC

29934    GGACATGGGAGGGCTTATGCTTTAACATGTGTAAATCCACTGCAATAATGACTGGTTCTT
         TTACCCCATAAGGTTGAGAATTTACCTGTAAACATTTTTGTCTGAAGAATTTGGATGTAA
         GTGAGGGCTGGGCCTCTATCTTATCTCACTTGGCTTCTCTCAGCACAGCACCTTGCCTGC
         TTGTTCTTACACATCCAGATGCACAGTAACTATTTCCTAATTATTAGAAATCTATTAGA
         ATCAATTGATTTCAGCTGGGCTTGGTGGCTCCTTCCTGTAATCCCAGCACTTTGGGAGGC
         [T,C]
         AAGGCTGGAGGATCACCTGAGTCCAGGAGTTTAAGACCAGCCTGGGCAACATAGGGAGAC
         CCTGTCTCTACAAAAAATAAAAAATTAGCCAGGCATGGTGGTGTGCACCTGTAGTCCCAG
         CTACTCAGGAGGCTGAGGCAGGAGGATCTCTTGAGCCTGGGAGGTCAGACTACAGTGAGC
         AATGATTGTGCCACTGCACTCCAGCCTGGGTGACAGAGTAAGACTCTGTCTCTTAAAAAA
         AAAAAAAAAAAAAGTTGATTTCTATTTGGATAGATAAATAATTCATTTTAGGACCTTTCTT

34480    CTGACTTCAAGTGATCCACCCGCCTCGGCCTCCCAAAGTGCTGGGATTATAAGCATAAGC
         CACTGTGCCCAGCTGCTCTCTATATTTTTAATACATATTATTTCCATTAATTTTCACAGC
         AGTTCATTTTATAGATGAGGAAACTAGGCCAGAGAAGTAAAATATCTTGCCCAAGATGAT
         GTAACTAGTAAGTGGCAGGATCAAGATTCAAACCAAGCAATGTTCAAACCTCTTGGAAGC
         AAGAATGTGGCCACTGTGGAAGGTGCAAGGCCTTGACAACAAGAATAGGGAAAAGAAGGA
         [A,G]
         CTAGAAGGAAAGAGATGGCATGGGCTCAGCAGGCCAGGGAGCTCTTAGCTGTGTGTGTTG
         GGAAGCTCAGAAGGGAGGAAGAGGTTGTCTGTGCAGGTAAGTCCTGAGAACACACCAGAC
         TTTTGAGAGGTGGAGCTTCATAGCCAGGTCATTAGGGGAGAAGGGAGCTATAGATTTTTT
         TTTTTTTTTTTTTTTTTTTTTTTTAGAGACGGGGTCTTACTATGTTGCCCAGGCTG
         GTCTTGAACTCCTGGGCTCAAGTGATCCTCCCACCTCAGCCTCCCAAAGTGCTGGGATTA

38812    AAATCCAGCAGATCCATTGAGAGTTTAAGCAGCAAGGTGTTGTGACCAAGTTAACATTTT
         AGAAGGATCACTGGTATGGAGGTTGGATTGGAGAGGGGAAAGCCTAAAGGTATAGAGACT
         AGTTAGGAAGCTATTGTAGGCTGGGCATGGTGGTTCATGCCTGTAATCTCAGCACTTTGG
         GAGGCTGAGGTGGGAGGATTGCTTGAGGCCAGGAGTTGAAGACCAACCTGGCCAACATAG
         CAAGACCCCGTCTCTGTTTTTCTTAATTAAAAGAAAAGTCCAGACGTAGACATAGTGGCT
         [T,C]
         ACGCCTGTAATGCCAGCACTTTGGGAGGCCAAGGTGGGCAGATTGCTTGAGGTCAAGAGT
         TTGGGATTAGGCCAGGCGCAGTGGCTCACGCCTGTAATCCCAGCACTTTGGGAGGCCGAG
         GTGGGCGGATCACAAGGTCAGGAGATCAAGACCATCCTGGCTAACACAATGAAACCCCGT
         CTCTACTAAAAGTACAAAAATTAGCCGGGCATGGTGGCGGACGCCTGTAGTCCCAGCTAC
         TCGGGAGGCTGAGGCAGGAGAATGGCGTGAACCTAGGAGGCGGAGCTTGCTGTGAGCAGA

40731    GTTCTGTCCTATGTCTGTCTCTCGGATGAAGCTGAGCTGGCTTTCAGAAGCCTGCAGAGT
         TAGGAAAGGAACCAGCTGGCCAGGGACAGACTATGAGGATTGTGCTGACCCAGCTGCCCC
         TGTGGGGATCACAGTTTACAGCCAGAGCCTGTGCGGACCCAGCTGTCTGCCAGGTTTCCT
         TAGAAACCTGAGAGTCAGTCTCTGTCCACTGAACTCCTAAGCTGGACAGGAGGCAGTGAT
         GCTAAACCCTGAAGGGCAACATGGCCTATGGAGAAAGCATGGAGCTCAGAGCCTGGAGTA
         [C,G]
         GGGCACAGATAGGATTGAATAAATTGTGTAGAAAGACTTTGAAAACAATAAAGCAAAAGA
         TGAATGAACGTTTTTTTTTAGACTTGAGGGACCAACAACCCCCAAACCCCAGATTCTGCCA
         GGTCCATGGGGAAGGAGAAGTTGCCTTGAGTGGAAGCCCCAAGTAGGGAGACTTACAGAA
         AAGAAGTCAAGAGCACTGGCTCCCAGGCAGAAATACTGATACCCTACTGGGGCTTCAGGC
         TGAGCTCCTCCCTTCACAAATCACTTCATCTCTCTGAGCCTGTTTCTGCATCTGTGACAT

41303    CTCTGAGCCTGTTTCTGCATCTGTGACATAAGATGGTAAGATAAAGGTGGCTGTCTCACC
         AATTATGTAAGGATTAAATGTGGAAAAGGACATAAAGTTGTATAGTGCTGCCATAGGGAC
```

FIGURE 3-26

```
         AGTGTTCAGTAAACGTGACACATTCTTAGTATCACTAAGAATCAGGTTCTTGGCCAGGCA
         CCGTGGCTCATGCCTGTAATCCCAACACTCTGGGAGGCCTAGGTCGGAGGATGGCTTGAA
         CACAGGAGTTTGAGACCAGCCTGAGCAACATAGTGAGACACTGTCTCTACAAAAAAAAAA
         [T,A]
         AATAATAATAATTGTTTTTAATTAGATGGGCAGGGCACTGTGGCTCACACCTGTAATCCC
         AGCACTTTGGGAGGCCAAGGCCGGAGGATTGCTTGAGGCCAGGAGTTCAGGAGCAGCCTG
         GGCCACATTCCTGTCTCTACAAAGAATAAAAAAGTTAACTGGGCATGGTGGCACATGCCT
         GTAATCCCAGCTACTCAAGAGGCTGAGGAGGAGGATTGCCTGAGCCCAGGAGTTCAAGAC
         TGCAGTGAGCCTTGATCACACCACTGTACTACAGCTTGGGCAACAGAGTGAGACCTTGTC

41305    CTGAGCCTGTTTCTGCATCTGTGACATAAGATGGTAAGATAAAGGTGGCTGTCTCACCAA
         TTATGTAAGGATTAAATGTGGAAAAGGACATAAAGTTGTATAGTGCTGCCATAGGGACAG
         TGTTCAGTAAACGTGACACATTCTTAGTATCACTAAGAATCAGGTTCTTGGCCAGGCACC
         GTGGCTCATGCCTGTAATCCCAACACTCTGGGAGGCCTAGGTCGGAGGATGGCTTGAACA
         CAGGAGTTTGAGACCAGCCTGAGCAACATAGTGAGACACTGTCTCTACAAAAAAAAAATA
         [-,A]
         TAATAATAATTGTTTTTAATTAGATGGGCAGGGCACTGTGGCTCACACCTGTAATCCCAG
         CACTTTGGGAGGCCAAGGCCGGAGGATTGCTTGAGGCCAGGAGTTCAGGAGCAGCCTGGG
         CCACATTCCTGTCTCTACAAAGAATAAAAAAGTTAACTGGGCATGGTGGCACATGCCTGT
         AATCCCAGCTACTCAAGAGGCTGAGGAGGAGGATTGCCTGAGCCCAGGAGTTCAAGACTG
         CAGTGAGCCTTGATCACACCACTGTACTACAGCTTGGGCAACAGAGTGAGACCTTGTCTC

41457    CTAAGAATCAGGTTCTTGGCCAGGCACCGTGGCTCATGCCTGTAATCCCAACACTCTGGG
         AGGCCTAGGTCGGAGGATGGCTTGAACACAGGAGTTTGAGACCAGCCTGAGCAACATAGT
         GAGACACTGTCTCTACAAAAAAAAAATAATAATAATAATTGTTTTTAATTAGATGGGCAG
         GGCACTGTGGCTCACACCTGTAATCCCAGCACTTTGGGAGGCCAAGGCCGGAGGATTGCT
         TGAGGCCAGGAGTTCAGGAGCAGCCTGGGCCACATTCCTGTCTCTACAAAGAATAAAAAA
         [G,C]
         TTAACTGGGCATGGTGGCACATGCCTGTAATCCCAGCTACTCAAGAGGCTGAGGAGGAGG
         ATTGCCTGAGCCCAGGAGTTCAAGACTGCAGTGAGCCTTGATCACACCACTGTACTACAG
         CTTGGGCAACAGAGTGAGACCTTGTCTCCAAAAAAAAAAAGTTTGTTTTTTTTTATCCACT
         CTCCTCACCAAACAAACTGAGTAAGTTAGAGCCCTCTCAGCTGGCATGTGTTGGAAACAG
         TGCCCTCTCATTAAAGTGCTGCCCTCACTCCCATTGCCTCTTGGCCTTGGTCAGTATGAT

43168    AGCTACTTGGGAGGCTGAGGCAGGAGAATCGCTTGAACCTGGAAGGCGGAGGTCGCAGTG
         AGCCGAGATCGTGCCATTGCACTTCAGCCTGGGCGACAGAGCGAGACTCTGTCTCAAAAA
         TAATAATAATAACAATAACTAGCCGGGCCTGGTGGCACATGCCTGTAGTCCCAGTTACTC
         AGGAGGCGGAGGCATGAGACTCAGGTGAACTAGGGAGACAGAGGTTGCAGTGAGCCAAGA
         TCACACCACTGCACTCCAGCCTGGTTGACAGAGCGAGACTCTGTCTCAAAAAAAAAAAAA
         [A,-,T]
         CCCATTTGCTCATTTTTTGGATACTAGTATAACTATCACTCTAAACCAGTTAGTACTTAA
         ATCAAGCAGATATGGGAGATGGTGAATTACCATCTACAGTGTTGTCATATATGTCACATA
         CTGAGCATTATCAGCTAGTAGAATCTAGTTAATTGTTCTATGTGTGATGTATGCAGAGTT
         CCCATTTTGAATGTGTTTTTACTATGCTTAAATAAATGACTGATGTCAGCAACCCCAAAA
         TGATACATCTGATGTAAGAGCCCCTGTTCCCCAATAATAACATCTAAACTATAGACATTG

43357    AGGCATGAGACTCAGGTGAACTAGGGAGACAGAGGTTGCAGTGAGCCAAGATCACACCAC
         TGCACTCCAGCCTGGTTGACAGAGCGAGACTCTGTCTCAAAAAAAAAAAAATCCCATTTG
         CTCATTTTTTGGATACTAGTATAACTATCACTCTAAACCAGTTAGTACTTAAATCAAGCA
         GATATGGGAGATGGTGAATTACCATCTACAGTGTTGTCATATATGTCACATACTGAGCAT
         TATCAGCTAGTAGAATCTAGTTAATTGTTCTATGTGTGATGTATGCAGAGTTCCCATTTT
         [T,G]
         AATGTGTTTTTACTATGCTTAAATAAATGACTGATGTCAGCAACCCCAAAATGATACATC
         TGATGTAAGAGCCCCTGTTCCCCAATAATAACATCTAAACTATAGACATTGGAATGAACA
         GGTGCCCCTAAGTTTCCTCCCTCCAGGGTTTCTTGGCCGGTCTCTGAGGACTACACATCC
         CTACTCCCGTCTTTCCTCATCTTCAGGCGCAGTAACAGTATCTCCAAGTCCCCTGGCCCC
         AGCTCCCCAAAGGAGCCCCTGCTGTTCAGCCGTGACATCAGCCGCTCAGAATCCCTTCGT

45664    CCAGCTTTCCTTGGCTTCCCCCACCCCCAGGTGAAAGTGATGCGCAGCCTGGACCACCCC
```

FIGURE 3-27

```
        AATGTGCTCAAGTTCATTGGTGTGCTGTACAAGGATAAGAAGCTGAACCTGCTGACAGAG
        TACATTGAGGGGGGCACACTGAAGGACTTTCTGCGCAGTATGGTGAGCACACCACCCCAT
        AGTCTCCAGGAGCCTTGGTGGGTTGTCAGACACCTATGCTATCACTACCCTAGGAGCTTA
        AAGGGCAGAGGGGCCCTGCTTTGCCTCCAAAGGACCATGCTGGGTGGGACTGAGCATACA
        [T,C]
        AGGGAGGCTTCACTGGGAGACCACATTGACCCATGGGGCCTGGACCACGAGTGGGACAGG
        GCTCAACAGCCTCTGAAAATCATTCCCCATTCTGCAGGATCCGTTCCCCTGGCAGCAGAA
        GGTCAGGTTTGCCAAAGGAATCGCCTCCGGAATGGTGAGTCCCACCAACAAACCTGCCAG
        CAGGGCGAGAGTAGGGAGAGGTGTGAGAATTGTGGGCTTCACTGGAAGGTAGAGACCCCT
        TCCTATGCAACTTGTGTGGGCTGGGTCAGCAGCTATTCATTGAGTTTGTCTGTGTCACTG

47549   AATTAGCTGGGCGTGGTGGTGCACGCCTGTAGTCCCAGCTACTCAGGAGGCCGAGGCAGG
        AGAATAGCTTGAACCTGGGAGGCAGAAGTTGCAGTGAGCCAAGATCACACCACTGCATTC
        CAGCCTGGGTGACAGAGTGAGACTTCATCTCAAAAAAAAAAAAAAAGAGAGACTGATATG
        GTTAGTACATTGGGGTGGAATGCGGAGGGTCCAGGGAATGGAGCCCTGCATAGGGGGCTA
        ATGAAACATTTCAGATTTCTGAATTAAGGTAGTGGCTGTGGGGACAGGAGCCTGGGAGGC
        [A,C]
        GGGTGGAGTCAGAATGGAGAGACTGGTTGGCAATGAGGGAACAGGAGGAGGAGGAGGAGG
        AGTTACGAGTGGCTTGAGGTGTCACTTACCAGACATTTGGGGGATGGGGGATAGCCGTGA
        TTGTTGAGCAACTGGTTTGGGAAGAGCTAGCATTGATCCCTGCTGTTCTGTGCTAGCAGA
        ACCTATCAGCATCTTCTGGGCAGGAAACTGGCTCCATGAGACTGGCTTAGGGAGAGGCTG
        CTAGTCACCTAATCTGCAGAGAAGGGGCAGCTGGAGCTGTGGGACAGAAGAGGCATCCAT

47908   GGAGTTACGAGTGGCTTGAGGTGTCACTTACCAGACATTTGGGGGATGGGGGATAGCCGT
        GATTGTTGAGCAACTGGTTTGGGAAGAGCTAGCATTGATCCCTGCTGTTCTGTGCTAGCA
        GAACCTATCAGCATCTTCTGGGCAGGAAACTGGCTCCATGAGACTGGCTTAGGGAGAGGC
        TGCTAGTCACCTAATCTGCAGAGAAGGGGCAGCTGGAGCTGTGGGACAGAAGAGGCATCC
        ATGTAGCTGGTGGGGGTGTCTCAGCTTGTGAAGAGGAGATGGCTTTGAGCAGGGCTGACA
        [C,A]
        TGAAAAGGCTGGAAGAAAAAAACAGACACACAAGAGTCTCAGGATCAGGTAGCATAGGAA
        AGTTGTGGACAGTCTTTGAGGAGCACTCCCTCAGGCAGGCAGGCAGGCAGGTCATGAGCT
        ATAGCGATTCAGGAAGAGCTCCCTGGGTGTGTGAGCAGCTCCAGGAGCCTAAGGGATGAA
        AGTAGTATTGCAGGGGGCTGGAGAGCAAGGAGTGGCTCCTTCTACATTTGCAAGGGAAGG
        AGAAAGGAAGTTGCTCCTGAGAGTGGTAAGAGTCAGTGGTGGAGGCCTGGAGAGGAGACA

52267   TTGTGAGGGGTAGAGGAGAGGAGAGACAAGGGATGGTTAGGATAATGAAGGAATGTTTTG
        TTTTTGTTTTTGTTTTTGAGATGGAGTTTCACTCTGTCACCCAGGCTGGAGTGCAGAGGT
        GCAATCTTGGCTCACTGCAGCCTCCGCCTCCCAGGTTCAAGCAATCCTCCTGCCTCAGCC
        TCCCAAGTAGCTGGGACTACAGGTGTGCGCCACCACGCCTGGCTAATTTTTTGTATTTTCA
        GTAGAGACAGGGTTTCGCCATATTGGCCAGGCTGGTCTCAAATGCCTGACCTCAGGTGAT
        [C,A]
        CACCCGCTTCAGCCTCCCAAAGTGCTGAGATTACAGGCATGAGCTACCGTGCCTGGCCAT
        GAAGGAAGATTTGTTTTAAAAAATTGTTTTCTTTAATATTAATTGAACACCTCTGTTCAG
        AGCACTGGGCTGGTGCCAGAGGGTTTCAGACATGAATCAGATCCAGCACCTCATAGAGCC
        TTAATCTGGCACACACACACAGCCACAAGGAGACACAGACAAGGCAGGGTAGGATGAGTG
        GAAGCTAGGAGCAGATGCTGATTTGGAACACTTGGCTTCTGCAGTGAAGCCCCTTCTTAG

54654   GGCCCCGGCCCCGGCCCCCAGGCCAGGCAGTGGCGGCCAAGGACCACGCATCTACTTTCA
        GAGCCCCCCCGGGGCCGCAGGAGAGGGCCCGGGCTGGGCGGATGATGAGGGCCCAGTGA
        GGCGCCAAGGGAAGGTCACCATCAAGTATGACCCCAAGGAGCTACGAAGCACCTCAACC
        TAGAGGAGTGGATCCTGGAGCAGCTCACGCGCCTCTACGACTGCCAGGAAGAGGAGATCT
        CAGAACTAGAGATTGACGTGGATGAGCTCCTGGACATGGAGAGTGACGATGCCTGGGCTT
        [T,C]
        CAGGGTCAAGGAGCTGCTGGTTGACTGTTACAAACCCACAGAGGCCTTCATCTCTGGCCT
        GCTGGACAAGATCCGGGCCATGCAGAAGCTGAGCACACCCCAGAAGAAGTGAGGGTCCCC
        GACCCAGGCGAACGGTGGCTCCCATAGGACAATCGCTACCCCCCGACCTCGTAGCAACAG
        CAATACCGGGGGACCCTGCGGCCAGGCCTGGTTCCATGAGCAGGGCTCCTCGTGCCCCTG
        GCCCAGGGGTCTCTTCCCCTGCCCCCTCAGTTTTCCACTTTTGGATTTTTTATTGTTAT
```

FIGURE 3-28

54679   GGCAGTGGCGGCCAAGGACCACGCATCTACTTTCAGAGCCCCCCCGGGGCCGCAGGAGA
        GGGCCCGGGCTGGGCGGATGATGAGGGCCCAGTGAGGCGCCAAGGGAAGGTCACCATCAA
        GTATGACCCCAAGGAGCTACGGAAGCACCTCAACCTAGAGGAGTGGATCCTGGAGCAGCT
        CACGCGCCTCTACGACTGCCAGGAAGAGGAGATCTCAGAACTAGAGATTGACGTGGATGA
        GCTCCTGGACATGGAGAGTGACGATGCCTGGGCTTCCAGGGTCAAGGAGCTGCTGGTTGA
        [C,G]
        TGTTACAAACCCACAGAGGCCTTCATCTCTGGCCTGCTGGACAAGATCCGGGCCATGCAG
        AAGCTGAGCACACCCCAGAAGAAGTGAGGGTCCCCGACCCAGGCGAACGGTGGCTCCCAT
        AGGACAATCGCTACCCCCCGACCTCGTAGCAACAGCAATACCGGGGGACCCTGCGGCCAG
        GCCTGGTTCCATGAGCAGGGCTCCTCGTGCCCCTGGCCCAGGGGTCTCTTCCCCTGCCCC
        CTCAGTTTTCCACTTTTGGATTTTTTTATTGTTATTAAACTGATGGGACTTTGTGTTTTT

54693   AGGACCACGCATCTACTTTCAGAGCCCCCCCGGGGCCGCAGGAGAGGGCCCGGGCTGGG
        CGGATGATGAGGGCCCAGTGAGGCGCCAAGGGAAGGTCACCATCAAGTATGACCCCAAGG
        AGCTACGGAAGCACCTCAACCTAGAGGAGTGGATCCTGGAGCAGCTCACGCGCCTCTACG
        ACTGCCAGGAAGAGGAGATCTCAGAACTAGAGATTGACGTGGATGAGCTCCTGGACATGG
        AGAGTGACGATGCCTGGGCTTCCAGGGTCAAGGAGCTGCTGGTTGACTGTTACAAACCCA
        [A,C]
        AGAGGCCTTCATCTCTGGCCTGCTGGACAAGATCCGGGCCATGCAGAAGCTGAGCACACC
        CCAGAAGAAGTGAGGGTCCCCGACCCAGGCGAACGGTGGCTCCCATAGGACAATCGCTAC
        CCCCCGACCTCGTAGCAACAGCAATACCGGGGGACCCTGCGGCCAGGCCTGGTTCCATGA
        GCAGGGCTCCTCGTGCCCCTGGCCCAGGGGTCTCTTCCCCTGCCCCCTCAGTTTTCCACT
        TTTGGATTTTTTTATTGTTATTAAACTGATGGGACTTTGTGTTTTTATATTGACTCTGCG

54706   TACTTTCAGAGCCCCCCCGGGGCCGCAGGAGAGGGCCCGGGCTGGGCGGATGATGAGGG
        CCCAGTGAGGCGCCAAGGGAAGGTCACCATCAAGTATGACCCCAAGGAGCTACGGAAGCA
        CCTCAACCTAGAGGAGTGGATCCTGGAGCAGCTCACGCGCCTCTACGACTGCCAGGAAGA
        GGAGATCTCAGAACTAGAGATTGACGTGGATGAGCTCCTGGACATGGAGAGTGACGATGC
        CTGGGCTTCCAGGGTCAAGGAGCTGCTGGTTGACTGTTACAAACCCACAGAGGCCTTCAT
        [T,C]
        TCTGGCCTGCTGGACAAGATCCGGGCCATGCAGAAGCTGAGCACACCCCAGAAGAAGTGA
        GGGTCCCCGACCCAGGCGAACGGTGGCTCCCATAGGACAATCGCTACCCCCCGACCTCGT
        AGCAACAGCAATACCGGGGGACCCTGCGGCCAGGCCTGGTTCCATGAGCAGGGCTCCTCG
        TGCCCCTGGCCCAGGGGTCTCTTCCCCTGCCCCCTCAGTTTTCCACTTTTGGATTTTTTT
        ATTGTTATTAAACTGATGGGACTTTGTGTTTTTATATTGACTCTGCGGCACGGGCCCTTT

54712   CAGAGCCCCCCCGGGGCCGCAGGAGAGGGCCCGGGCTGGGCGGATGATGAGGGCCCAGT
        GAGGCGCCAAGGGAAGGTCACCATCAAGTATGACCCCAAGGAGCTACGGAAGCACCTCAA
        CCTAGAGGAGTGGATCCTGGAGCAGCTCACGCGCCTCTACGACTGCCAGGAAGAGGAGAT
        CTCAGAACTAGAGATTGACGTGGATGAGCTCCTGGACATGGAGAGTGACGATGCCTGGGC
        TTCCAGGGTCAAGGAGCTGCTGGTTGACTGTTACAAACCCACAGAGGCCTTCATCTCTGG
        [T,C]
        CTGCTGGACAAGATCCGGGCCATGCAGAAGCTGAGCACACCCCAGAAGAAGTGAGGGTCC
        CCGACCCAGGCGAACGGTGGCTCCCATAGGACAATCGCTACCCCCCGACCTCGTAGCAAC
        AGCAATACCGGGGGACCCTGCGGCCAGGCCTGGTTCCATGAGCAGGGCTCCTCGTGCCCC
        TGGCCCAGGGGTCTCTTCCCCTGCCCCCTCAGTTTTCCACTTTTGGATTTTTTTATTGTT
        ATTAAACTGATGGGACTTTGTGTTTTTATATTGACTCTGCGGCACGGGCCCTTTAATAAA

54799   GTATGACCCCAAGGAGCTACGGAAGCACCTCAACCTAGAGGAGTGGATCCTGGAGCAGCT
        CACGCGCCTCTACGACTGCCAGGAAGAGGAGATCTCAGAACTAGAGATTGACGTGGATGA
        GCTCCTGGACATGGAGAGTGACGATGCCTGGGCTTCCAGGGTCAAGGAGCTGCTGGTTGA
        CTGTTACAAACCCACAGAGGCCTTCATCTCTGGCCTGCTGGACAAGATCCGGGCCATGCA
        GAAGCTGAGCACACCCCAGAAGAAGTGAGGGTCCCCGACCCAGGCGAACGGTGGCTCCCA
        [T,C]
        AGGACAATCGCTACCCCCCGACCTCGTAGCAACAGCAATACCGGGGGACCCTGCGGCCAG
        GCCTGGTTCCATGAGCAGGGCTCCTCGTGCCCCTGGCCCAGGGGTCTCTTCCCCTGCCCC
        CTCAGTTTTCCACTTTTGGATTTTTTTATTGTTATTAAACTGATGGGACTTTGTGTTTTT
        ATATTGACTCTGCGGCACGGGCCCTTTAATAAAGCGAGGTAGGGTACGCCTTTGGTGCAG
        CTCAAAAAAAAAAAAAAAAAAATGATTTCCAGCGGTCCACATTAGAGTTGAAATTTTCTGGT

FIGURE 3-29

54819   GGAAGCACCTCAACCTAGAGGAGTGGATCCTGGAGCAGCTCACGCGCCTCTACGACTGCC
AGGAAGAGGAGATCTCAGAACTAGAGATTGACGTGGATGAGCTCCTGGACATGGAGAGTG
ACGATGCCTGGGCTTCCAGGGTCAAGGAGCTGCTGGTTGACTGTTACAAACCCACAGAGG
CCTTCATCTCTGGCCTGCTGGACAAGATCCGGGCCATGCAGAAGCTGAGCACACCCCAGA
AGAAGTGAGGGTCCCCGACCCAGGCGAACGGTGGCTCCCATAGGACAATCGCTACCCCCC
[G,A]
ACCTCGTAGCAACAGCAATACCGGGGGACCCTGCGGCCAGGCCTGGTTCCATGAGCAGGG
CTCCTCGTGCCCCTGGCCCAGGGGTCTCTTCCCCTGCCCCCTCAGTTTTCCACTTTTGGA
TTTTTTTATTGTTATTAAACTGATGGGACTTTGTGTTTTTATATTGACTCTGCGGCACGG
GCCCTTTAATAAAGCGAGGTAGGGTACGCCTTTGGTGCAGCTCAAAAAAAAAAAAAAAAA
TGATTTCCAGCGGTCCACATTAGAGTTGAAATTTTCTGGTGGGAGAATCTATACCTTGTT

55499   TTGTTTTCTAATACCTCTTGTCATTCTAAATATCTTTAATTTATTAAAAAATATATATAT
ACAGTATTGAATGCCTACTGTGTGCTAGGTACAGTTCTAAACACTTGGGTTACAGCAGCG
AACAAAATAAAGGTGCTTACCCTCATAGAACATAGATTCTAGCATGGTATCTACTGTATC
ATACAGTAGATACAATAAGTAAACTATATTGAATATTAGAATGTGGCAGATGCTATGGAA
AAAGAGTCAAGACAAGTAAAGACGATTGTTCAGGGTACCAGTTGCAATTTTTAAATATGGT
[C,T]
GTCAGAGCAGGCCTCACTGAGGTGACATGACATTTAAGCATAAACATGGAGGAGGAGGAG
TAAGCCTGAGCTGTCTTAGGCTTCCGGGGCAGCCAAGCCATTTCCGTGGCACTAGGAGCC
TGGTGTTTCCGATTCCACCTTTGATAACTGCATTTTCTCTAAGATATGGGAGGGAAGTTT
TTCTCCTATTGTTTTTAAGTATTAACTCCAGCTAGTCCAGCCTTGTTATAGTGTTACCTA
ATCTTTATAGCAAATATATGAGGTACCGGTAACATTATGCCCATTTCTCACAGAGGCACT

56825   ACTGATGGCTCAAAGGGTGTGAAAAAGTCAGTGATGCTCCCCCTTTCTACTCCAGATCCT
GTCCTTCCTGGAGCAAGGTTGAGGGAGTAGGTTTTGAAGAGTCCCTTAATATGTGGTGGA
ACAGGCCAGGAGTTAGAGAAAGGGCTGGCTTCTGTTTACCTGCTCACTGGCTCTAGCCAG
CCCAGGGACCACATCAATGTGAGAGGAAGCCTCCACCTCATGTTTTCAAACTTAATACTG
GAGACTGGCTGAGAACTTACGGACAACATCCTTTCTGTCTGAAACAAACAGTCACAAGCA
[C,A]
AGGAAGAGGCTGGGGGACTAGAAAGAGGCCCTGCCCTCTAGAAAGCTCAGATCTTGGCTT
CTGTTACTCATACTCGGGTGGGCTCCTTAGTCAGATGCCTAAAACATTTTGCCTAAAGCT
CGATGGGTTCTGGAGGACAGTGTGGCTTGTCACAGGCCTAGAGTCTGAGGGAGGGGAGTG
GGAGTCTCAGCAATCTCTTGGTCTTGGCTTCATGGCAACCACTGCTCACCCTTCAACATG
CCTGGTTTAGGCAGCAGCTTGGGCTGGGAAGAGGTGGTGGCAGAGTCTCAAAGCTGAGAT

58871   CGTCACCCACCACCCAACCCCTGCCGCACTCCAGCCTTTAACAAGGGCTGTCTAGATATT
CATTTTAACTACCTCCACCTTGGAAACAATTGCTGAAGGGGAGAGGATTTGCAATGACCA
ACCACCTTGTTGGGACGCCTGCACACCTGTCTTTCCTGCTTCAACCTGAAAGATTCCTGA
TGATGATAATCTGGACACAGAAGCCGGGCACGGTGGCTCTAGCCTGTAATCTCAGCACTT
TGGGAGGCCTCAGCAGGTGGATCACCTGAGATCAAGAGTTTGAGAACAGCCTGACCAACA
[T,A]
GGTGAAACCCCGTCTCTACTAAAAATACAAAAATTAGCCAGGTGTGGTGGCACATACCTG
TAATCCCAGCTACTCTGGAGGCTGAGGCAGGAGAATCGCTTGAACCCACAAGGCAGAGGT
TGCAGTGAGGCGAGATCATGCCATTGCACTCCAGCCTGTGCAACAAGAGCCAAACTCCAT
CTCAAAAAAAAA

FIGURE 3-30

SEQUENCE LISTING

<160> NUMBER OF SEQ ID NOS: 4

<210> SEQ ID NO 1
<211> LENGTH: 2320
<212> TYPE: DNA
<213> ORGANISM: Homo sapiens

<400> SEQUENCE: 1

```
cccagggcgc cgtaggcggt gcatcccgtt cgcgcctggg gctgtggtct tcccgcgcct      60
gaggcggcgg cggcaggagc tgaggggagt tgtagggaac tgaggggagc tgctgtgtcc     120
cccgcctcct cctccccatt tccgcgctcc cgggaccatg tccgcgctgg cgggtgaaga     180
tgtctggagg tgtccaggct gtggggacca cattgctcca agccagatat ggtacaggac     240
tgtcaacgaa acctggcacg gctcttgctt ccggtgaaag tgatgcgcag cctggaccac     300
cccaatgtgc tcaagttcat tggtgtgctg tacaaggata agaagctgaa cctgctgaca     360
```

```
gagtacattg agggggcac actgaaggac tttctgcgca gtatggatcc gttcccctgg    420
cagcagaagg tcaggtttgc caaggaatc gcctccggaa tggacaagac tgtggtggtg    480
gcagactttg ggctgtcacg gctcatagtg aagagagga aagggcccc catggagaag    540 gccaccacca gaaacgcac cttgcgcaag aacgaccgca agaagcgcta cacggtggtg    600
ggaaacccct actggatggc ccctgagatg ctgaacggaa gagctatga tgagacggtg    660 gatatcttct cctttgggat cgttctctgt gagatcattg gcaggtgta tgcagatcct    720 gactgccttc cccgaacact ggactttggc ctcaacgtga agcttttctg ggagaagttt    780
gttcccacag attgtccccc ggccttcttc ccgctggccg ccatctgctg cagactggag    840
cctgagagca gaccagcatt ctcgaaattg aggactcct tgaggccct ctccctgtac    900 ctggggagc tgggcatccc gctgcctgca gagctggagg agttggacca cactgtgagc    960
atgcagtacg gcctgacccg ggactcacct ccctagccct ggcccagccc ctgcaggggg   1020
ggtgttctac agccagcatt gcccctctgt gccccattcc tgctgtgagc agggccgtcc   1080
gggcttcctg tggattggcg aatgtttag aagcagaaca aaccattcct attacctccc   1140
caggaggcaa gtgggcgcag caccagggaa atgtatctcc acaggttctg ggcctagtt   1200 actgtctgta atccaatac ttgcctgaaa gctgtgaaga gaaaaaaac ccctggcctt   1260 tgggccagga ggaatctgtt actcgaatcc acccaggaac tccctggcag tggattgtgg   1320
gaggctcttg cttacactaa tcagcgtgac ctggacctgc tgggcaggat cccagggtga   1380
acctgcctgt gaactctgaa gtcactagtc cagctgggtg caggaggact tcaagtgtgt   1440
ggacgaaaga aagactgatg gctcaaaggg tgtgaaaaag tcagtgatgc tccccctttc   1500
tactccagat cctgtccttc ctggagcaag gttgagggag taggttttga agagtccctt   1560
aatatgtggt ggaacaggcc aggagttaga gaaagggctg gcttctgttt acctgctcac   1620
tggctctagc cagcccaggg accacatcaa tgtgagagga agcctccacc tcatgttttc   1680
aaacttaata ctggagactg gctgagaact tacggacaac atcctttctg tctgaaacaa   1740
acagtcacaa gcacaggaag aggctggggg actagaaaga ggccctgccc tctagaaagc   1800
tcagatcttg gcttctgtta ctcatactcg ggtgggctcc ttagtcagat gcctaaaaca   1860
ttttgcctaa agctcgatgg gttctggagg acagtgtggc ttgtcacagg cctagagtct   1920
gagggagggg agtgggagtc tcagcaatct cttggtcttg gcttcatggc aaccactgct   1980 caccttcaa catgcctggt ttaggcagca gcttgggctg ggaagaggtg gtggcagagt   2040
ctcaaagctg agatgctgag agagatagct ccctgagctg ggccatctga cttctacctc   2100
ccatgtttgc tctcccaact cattagctcc tgggcagcat cctcctgagc cacatgtgca   2160
ggtactggaa aacctccatc ttggctccca gagctctagg aactcttcat cacaactaga   2220
tttgcctctt ctaagtgtct atgagcttgc accatattta ataaattggg aatgggtttg   2280
gggtattaaa aaaaaaaaa aaaaaaaaa aaaaaaaaa                            2320
```

<210> SEQ ID NO 2
<211> LENGTH: 255
<212> TYPE: PRT
<213> ORGANISM: Homo sapiens

<400> SEQUENCE: 2

Met Val Gln Asp Cys Gln Arg Asn Leu Ala Arg Leu Leu Leu Pro Val
1               5                   10                  15

Lys Val Met Arg Ser Leu Asp His Pro Asn Val Leu Lys Phe Ile Gly

```
                   20                  25                  30
Val Leu Tyr Lys Asp Lys Lys Leu Asn Leu Leu Thr Glu Tyr Ile Glu
                35                  40                  45
Gly Gly Thr Leu Lys Asp Phe Leu Arg Ser Met Asp Pro Phe Pro Trp
     50                  55                  60
Gln Gln Lys Val Arg Phe Ala Lys Gly Ile Ala Ser Gly Met Asp Lys
 65                  70                  75                  80
Thr Val Val Ala Asp Phe Gly Leu Ser Arg Leu Ile Val Glu Glu
                85                  90                  95
Arg Lys Arg Ala Pro Met Glu Lys Ala Thr Thr Lys Lys Arg Thr Leu
                100                 105                 110
Arg Lys Asn Asp Arg Lys Lys Arg Tyr Thr Val Val Gly Asn Pro Tyr
                115                 120                 125
Trp Met Ala Pro Glu Met Leu Asn Gly Lys Ser Tyr Asp Glu Thr Val
            130                 135                 140
Asp Ile Phe Ser Phe Gly Ile Val Leu Cys Glu Ile Ile Gly Gln Val
145                 150                 155                 160
Tyr Ala Asp Pro Asp Cys Leu Pro Arg Thr Leu Asp Phe Gly Leu Asn
                165                 170                 175
Val Lys Leu Phe Trp Glu Lys Phe Val Pro Thr Asp Cys Pro Pro Ala
            180                 185                 190
Phe Phe Pro Leu Ala Ala Ile Cys Cys Arg Leu Glu Pro Glu Ser Arg
        195                 200                 205
Pro Ala Phe Ser Lys Leu Glu Asp Ser Phe Glu Ala Leu Ser Leu Tyr
    210                 215                 220
Leu Gly Glu Leu Gly Ile Pro Leu Pro Ala Glu Leu Glu Glu Leu Asp
225                 230                 235                 240
His Thr Val Ser Met Gln Tyr Gly Leu Thr Arg Asp Ser Pro Pro
                245                 250                 255

<210> SEQ ID NO 3
<211> LENGTH: 59065
<212> TYPE: DNA
<213> ORGANISM: Homo sapiens

<400> SEQUENCE: 3
tcatccttgc gcaggggcca tgctaacctt ctgtgtctca gtccaatttt aatgtatgtg      60
ctgctgaagc gagagtacca gaggttttttt tgatggcagt gacttgaact tatttaaaag    120
ataaggagga gccagtgagg gagagggtg ctgtaaagat aactaaaagt gcacttcttc      180
taagaagtaa gatggaatgg gatccagaac agggtgtca taccgagtag cccagccttt      240
gttccgtgga cactggggag tctaacccag agctgagata gcttgcagtg tggatgagcc    300
agctgagtac agcagatagg gaaagaagc caaaaatctg aagtagggct ggggtgaagg     360
acagggaagg gctagagaga catttggaaa gtgaaccag gtggatatga gaggagagag     420
tagagggtct tgatttcggg tctttcatgc ttaacccaaa gcaggtacta agtatgtgt      480 tgattgaatg tctttgggtt tctcaagact ggagaaagca gggcaagctc tggagggtat    540
ggcaataaca agttatcttg aatatcctca tggtggaaag tcctgatcct gtttgaattt     600
tggaaataga aatcattcag agccaagaga ttgaattgtt gagtaagtgg gtggtcaggt    660
tacagactta attttgggtt aaaaagtaaa aacaagaaac aaggtgtggc tctaaaataa    720
tgagatgtgc tgggggtggg gcatggcagc tcataaactg accctgaaag ctcttacatg    780
taagagttcc aaaaatattt ccaaaacttg gaagattcat ttggatgttt gtgttcatta    840
```

-continued

```
aaatctctca ctaattcatt gtcttgtcca ctgtccgtaa cccaacctgg gattggtttg    900
agtgagtctc tcagactttc tgccttggag tttgtgagag agatggcata ctctgtgacc    960
actgtcaccc taaaaccaaa aaggcccctc ttgacaagga gtctgaggat tttagaccca   1020
ggaagaatga gtgatgggca tatatatatc ctattactga ggcatgagaa gagtggaatg   1080
ggtgggttga ggtggtgttt taaggcctct tgccagcttg tttaactctt ctctggggaa   1140
cgaggggggac aactgtgtac attggctgct ccagaatgat gttgagcaat cttgaagtgc  1200
caggagctgt gctttgtcta ttcatggccc ctgtgcctgt gaaacagggt tcggtgactg   1260
tcactgtgcc tgtggcagtc tgtagttacc agagagaac aaagctgcat acacagagcg    1320
cacaagggag tcttgtaaca accttgtcct gctttctagg gctgagtcag gtaccacagc   1380
ttgatctcag ctgtcctctt tatttcaaga agttgacatc tgagccatac caggagtatt   1440
gtattttgtt tgaggcctct cttttggag gaacatggac cgactctgtg cttttgtcta    1500
tgctggtctc tgagctcaca caaccttca ccctcctttc tcagccagtg ataggtaagt    1560
cttccctatc ttgcaaggct cagctcaagt gtcagcttcc tctacaaaga cttttcctggt  1620
tcccctcatt ggagtgaaca agagttgaca tggtagaatg gaaagagcag aagctttaga   1680
atgagccaga cctgagtatg aatgctagat ccaccactta gctagtcaac cctgccccct   1740
gcctcaagtt ttaattttcc tatccattaa gtgaatataa taatacctgt gtcacaggat   1800
tattttgaga attaaatgag attaggtcta tgaaagcacc tagcagagtt cttggcatat   1860
aggaggcatt cattaaatat ttgttcttcc ccttttatac ccattacttt tcttttttctg  1920
aactaaaata atacttggtt ctatctctga ataacatcc aagtgaaaaa tcaacaacat    1980
gaaagagcag ttcttttcca gtggatttgc ttcttaagga gcagagatta tgtaatctaa   2040
cagcctccaa catacaaaga gctttgtatc tagaacaggg gtccccagcc cctgaccgc    2100
caactggtac gggtctgtag cctgttagga accaggctgc acagcaggag gtgagcggcg   2160
ggccagtgag cattgctgcc tgagctctgc ctcctgtcag atcagtggtg gcattagatt   2220
ctcataggag tgtgaaccct attgtgaact gcacatgcaa gggatctggg ttgcatgctc   2280
cttatgagaa tctcactaat ggctgatgat ctgagttgga acagtttgat accaaaacca   2340
tccccccgcc ccccaacccc cagcctaggg tccgtggaaa aattggcccc tggtgccaaa   2400
aaggttgagg actgctgatc tagaggacca atttattcaa tgttggttga gtaaatgagc   2460
tcttggatta ggtgatggaa aaatctgaaa aaacagggct tttgaggaat aggaaaaggc   2520
agtaacatgt ttaacccaga gagaagtttc tggctgttgg ctgggaatag tcataggaag   2580
ggctgacact gaaaagaagg agattgtgtt cgtttcttct tctcagagct ataagcaaag   2640
gctgaaagtt ctagaaaaag gcaagtttg tttcagtaga aaaaggata atcagaacca    2700
tttttagaaa atgaatgag actacttttg aggccatgag ttccttgtcc ctggagagat    2760
gagcagaggt tggacaagtg cttaccagag atcttgtgga ggcagaaact gtgcatctag   2820
cagagcattg gcctaaccct ttcaaatgag atgctgttaa ctcagtctta ttctacatgg   2880
taggaatcct gtcccttttgc ctcctgctac tttgggcctc tcaacctctt ggttttgtgt  2940
gcaggtgaaa atgtctggag gtgtccaggc tgtgggacc acattgctcc aagccagata    3000
tggtacagga ctgtcaacga aacctggcac ggctcttgct tccggtaggt gggcctatcc   3060
tcccatcttt accagtgtac tatgggccaa gcactatttc atgttctgat ggaaaacaca   3120
gaaacaagct tctgagttga gaatttcaat cttagggtgg ggaaaggaat gtaccaagga   3180
```

-continued

```
agagctcatg accaaacctc aagtgtggcc ccctgaacc caggttaaat tggaagagcc    3240
ataaatgggc cagctggagg cagggtgggg ggatgagagg agccctttcc agggttgtcc    3300
catatccctc actttatggg tgaggaaact gaggcccagg aagagtgact ttcctgtggc    3360
tgcactacag attatgcagg tacttcaaga gttgtttgta ttcttatttt attttatttt    3420
attttatttt attttatttt attttatgag agggattctt gctgttgccc aggctggagt    3480
gcagtggtgc aatctcggct cactgcaatc tctgcctgct gggttcaagt gattttctg    3540
ccttagcttc ctgagtagct gagatgcag gcacctgcca ccatgcgcag ctaattttg     3600
tattttagtg gagacggggg tttcaacatg ttggtcaggc tggtcttgaa ctcctgacct    3660
caaatgatgc acccacctcg acctcccaaa gtgctggaat tacaggcgtg aaccactgtg   3720
cccagccaag agttgttttt agtgtggttg gcagagccag ctcttccttc accacaggat   3780
gcctccctag gttcctactt tttgttacta gcttttatta tagctatatt attattatta   3840
ttattattat tattattatt attattgaga cagagtctcg ctctgtcgcc caggctggtg   3900
tacagtggtg cgatcccggg ctcactgcaa cctctgcctc ccgagttcaa gcagttctcc   3960
tgcctcagcc ccccgagtag gtgggactac aggcgcctgc caccacaccc ggctaattt   4020
tgtattttta gtagagacgg ggtttcacct tgttgaccag gctggtctgg agctcctgac   4080
ctcaggtaag tgctagaatc acaggcgtga accactgcgc ccagccaaga gttgttttta   4140
gtgtggttgg cagagccagc tcttcctcac cacaggttgc ctccctaggt tcctactttt    4200
tgttactagc tttattatag ctacattatt attattattg ttattattat tgagacagag   4260
tctcgctctg tcgcccaggc tggtgtacag tgatgtgatc ttggctcact gcaacctctg   4320
cccccgagt tcaagcaatt ctcctgcttc agcccccta gtaggtggga ctccaggcac    4380
ctgccaccac gcccagctaa tttttgtatt tttagtagag gcggggtttc accttgttgg   4440
ccaggctggt ctcaaactcc tgacctcagg tgatccgcct gcctcggcct cccaaaatgt   4500
tgggattaca ggcatgagcc accgcgccct gcctatagct acattatttt tgtaggcagc   4560
tcagtttctt aaaaattata cagacttcaa atcagatttg ttcctgctgt ctgaggctca   4620
gtttcttcat ctggaaaatg gatggtaata atcttgttga gattgaatga aataatatat   4680
gcagtgtatc cagtacatgg tagacaccca gtgaatggtt attccttcct cccatcggat   4740
tggaattctc aagggtggga acttgtcttt atattcttca caacgtaaaa tagttgaaat   4800
ttgttggtgg aaagaagagc agtccactcc agaggctgga tgggcatgcc tggcccccaa   4860
ggtctgaagt ggtagggctg tgcctatatc ctgagaatga gatagactag gcaggcacct   4920
tgtgctgtag attccagctc ctgcacatag ctcttgttgt aaaacatccc tgtgcttata   4980
ccaagtaatt gagttgacct ttaaacactt gcctcttccc tgggaaccat atagggatt    5040
ggcctggaga cgtctggcct ctggaagagt tggaaagcag ccatcattat tatcctttcc   5100
tttcagctat aactcagagc tctcaagtct tttctgtgga tcttattgcc ttggttcttg   5160
cccctttttac tcccagggaa gttgattctg tcttttctgt tccatttagt atgacaggag   5220
cagagaatgt cagagctgta aggaccttaa tagttaaagc ctttggctgg tcctttcatt   5280
ttatagctgg gactaataag taacgtcaaa acccaatgag ttcacagatt gggtctcgcc   5340
ttggcatgta acccatatgt tcatattctt gctgttttcc tatgtgtatg aatattttct   5400
atccaaaata agcaggacag ggtagagcaa gttaatcttt ggaatttctg gattctctta   5460
gagctaaaaa acttcagaac tagaagaaac cacccactat atggtataac ccattcatat   5520
cacagatgag gcctgaaacc aaaaagactt gctcaggcca tggatgacaa gagctggccc   5580
```

```
tagcactgaa ctcttgggtc atttgtaggt ctagtcagat gctagcttgt tagctctgtg    5640
cgtgcgtgtg tgtgtgtgtg tgtgtgtgtg tgtgtgagat agagacagaa agataacata    5700
tgtacacaaa tacataaaga ggaagtagac acgttagcat ggtagataag agtacaggca    5760
ggccaggcgt ggtggctcac gcctgtaatc ccagcacttt gggaggccaa ggcaggtgga    5820
tcacctgagg tcaggaattc gagaccagcc tgaccaacat ggtgaaaccc catctctact    5880
aaatacagaa aaaattagc ttggcatggt ggcacatgcc tgtaatccca gctacttggg     5940
aagctgaagc aggagaatcg cttgaatccg ggaagcagaa gttgcagtga gccgagattg    6000
tgccattaca gtctagcctg gcaacaaga gggaaactcc atcgcaaaaa aacaaccacc     6060
accaagagta caggctatgg aatgagacta tggttttaaa tcctggcttt gcaatttatt    6120
aactagcctt aagtgacttc cctgagcttc aggcaccaat ctgtaaaatg aggataagaa    6180
tattactcat gccacatggt tgttagggag gattaaatgt gataacctat ataaagtggc    6240
tagcatagca tctgacatat agaaaactct taatagggcc ggacgtggtg gcttatgcct    6300
gtaatcctag cactctggga ggccgaggca aaggatcgc ttgagcccat gagcccagga     6360
gtttgagacc agcctggcca acatggcaaa actccacctc tacaaaaaat acaaaaatat    6420
tagccaggcg tgatggcaca cacctgtagt cccagctact ggggaagctg aggagcgatg    6480
attacctgag cccagggata tcaaggctgt agtgagctgt gatcatgcca ctgtactcca    6540
tccagctggg gacagagtg aaacccctgt ctcaaaacaa aacaaatgaa aaaaaaaacc      6600
cttaataatc agtaactgtc actttatatt atgttgtgag tgtgtgtcta tatacaccta    6660
tatgtataca tttctcttat tacacattca ttggtgatct gatgtggagc cccagggatt    6720
aagggcaact ttgaactacc ctgacacaat caagccaaat atcattcccg tggaggaagt    6780
agagtatcta ggttctgtct cctagttgca gctttacctt gaggacagag actctaatcc    6840
agctgtgctg aaggagcaca tctcctgact tctgagcttt cccctggtaa attcaaactg    6900
gatgtcacgg cgccctcaga tagagcctgg taatttgccc tggggagagt gactgtcttt    6960
tggatctaat ttgacttttg ccccagttgg aggaaaatct tcagggctag gaaggattgt    7020
atttgtctga ccccagagat aacctggggtt ttgaggaaca tggggcatca acctgaatgg   7080
tcttgtaaga tctctcccac gccagcttgc cagtgttttct ctgatgaatt tagagtacct   7140
gagtagtgca ggcctgctgg gaggaggact ctccctctgt gctactcaga gaaattcatt    7200
cttcaaggcc ccttccagc cttgctctta cccagctggg ctacagttac aataaaggaa     7260
atgacttttc ttctccccctt cccccagtac ctttgttttc ctagtcacag ggtggggctg   7320
gatattgaat ggagaaattg ctgggggtcca tcctaaactc ctcccctcat ctctcccta    7380 cattacccca ttcttctgtc tgcagccaca tccataatcc tgcctctgtt agccttccga    7440
cagaccctca ggtgcccagg acaacaggaa gctacttaaa gctggaacct cagactgtgc    7500
aatggaggcc agtgacaaaa ctgaaagtag ctctgtcagt aattgtgctg gtgcgattag    7560
gcagctggca agaatctttt ggatctcctg gacatatggc tgactagtcc tcccaagcct    7620
tcccaacagg cctctttttt ttccttttt tcttttcttt ttttcttttc tttctttctt     7680
tctttttttt ttttttttag gctagtgaag tgaaattgtg ggagtggaaa aggaacaaag    7740
aaatcggtaa ctggtagtga tcaattactt gtaaacacta ttgtacttgg accagcccag    7800
taggcctttt ttaaaactct gagttacctc tcttcccttt ccttgagcag tgccattaat    7860
tctgtatctg gggcaatcct ttctgatgtt ctctggacct ggctctctct ccttaggaga    7920
```

-continued

```
ggccaggaga gtagccagag agcatgtcat ttgtagctga ggttaaagtg tggagctatc    7980
aatggtgacc tggcctcttg gcatgttagc aagccagagg accttgacaa cttttttgat    8040
gattgtccgt tcaccctgat caaaggtgtt tggcttagga ggagggaaga aaagctaccc    8100
ctattagtct tgatggcccc agcgtgggtc tctattgctt gacctggttc ctagcagcat    8160
tatcagaagg aaaatccacc gctcttaagg ctcctgggaa cttcaggac ttcctttctc     8220
aggattgcaa acataagact atttgagctt tcactttga aaagcggtta ctaataccta     8280
tactctggga aagggctaat gcagatagaa gactgtggtc actgcatcag gcaacagacc    8340
atttccgcta aatttagtga ctccaggaag gccagtgaag aaataacaca cgtagcaacc    8400
agagactgtg ttgtaatatg ttggctgaca gcagggtact ttctgtgatg ctgaaagcca    8460
cattcatttt ctctcccctc atcccatct aagcaagcct ggtagaatca taattacagt     8520
aataggtacc acttattgag tactctgtgc cagacaccct cctgagcata cgacatgcat    8580
agcacattta atccttacaa tgacttaata aaatgtagta ctagtcttac ctacttcgag    8640
aatagggaaa tggaggttac ttgtttaaag tcacagagct aataggtagc atagctgaga    8700
tttgaactca ggcattctta ctccttgcct gcaagagtct cttggcattc ttgaatgcaa    8760
gcatatttct taacctcact gaggctcagt ttcctcttat ataatatggg gtaaagagcc    8820
ctcaccctgc ctgccacaca ctggtagtgt cagataacat tgaagggtgt tagtttaaag   8880
gcttcatgga ctctataatg tcaacaaaag tgctgttaac tttcttctgg gtctcaggct    8940
cctgatgtag agtcagtgga gcaaccctgc catctgctgt tatgctgttg atgttgctgc    9000
cacacttact aacctaaacc tttgattctg gctgtggcct tctccagaag gtgtttactc    9060
atttgtccag tttatctttt aggaaacagc cagcccgtag atcattaagg ctggctattg    9120
gacaggggc tggggcctgc ctgacagagg aaggaagggc agacatctgg ttcttcctct     9180
gcccctacaa gagactccag cctgaccaca gagtggtact cctaggatgt agcagcagca    9240
tatgagcttg aatgtgcctt aatcctgctc tttactttga gaagagaga ctaaggaccc     9300
acagatgttt cacagcttct ataggaggca gaggtagaaa aatggagaga gatgaggcca    9360
gagatagata actgatatta attaaacgtt gtattaagaa cctcacttag attatctgat    9420
tcaatcttca taataaccct gcaaccccca cctttttttg agaacagggt cttgctctgt    9480
tgtccaggct acagtgcact ggtacaatca tagttcactg cagtgtcaac ctcctgagct    9540
caagcaatcc tccccctca gccttgcaag cagcttggac tacaggcgtg ccaccacacc     9600
ttgccatttt ttttttatttt aagtagaaac aaggtcttat taatactatg ttgcccaggc   9660
tggtcttgaa ctccagcgat cctcctgccc cagcctccca aagtgcttgg gattacggaa    9720
gtaagccact gtgcctggcc agtgcaaccc ccattttata ctaaaacagg aaggcccaga    9780
aaggtttgga gtaacttgtc cagggtcaca cagatgatat ttgaactcag gtctccctgg    9840
ctcccaagag agtctgcttt ccactaggac tcccaggaga aaaaaaaaa aaaaaacagt     9900
agacttggag acagaaaatc tgatttgagt cttagttgag ctaggctaac tgtgtaactg    9960
tgggcaagtt ccttagcccc tgtgagcctc agtttcttat ctgtaaaatg tcataaaaga   10020
aatccatctc atggagtagt tgtgatgatc aaggactctg aaaacattag aatggtttaa   10080
tgtgaaggat tagcagcagc acatggcaac attgtgcatc ttatattaac tatccaaata   10140
tatcaagcgt catttgctat atataaaagt catcaaatta ggcactgtgg gggatacgga   10200
gttggcatac tagcctggcc tcttaattaa ttcattaatt agcttattta tttttgagat   10260
aggtcttgct ctattgccca ggctggagtg cagtggcatg atgatagctt actatagcct   10320
```

```
caatctccca ggcttaaaca atcctcctga gtagctggga ctacaggcac acactaccat   10380
gcccagctaa ttttttttta attttttgta gagacagggt cttgctctgt tgcccaggct   10440
ggtctcaaac tcctgggctc gagatcctcc cacctgggcc tcacaaagtg ttgggattac   10500
aggtatgagc cacggcacct ggcctggtct cttaactggt tccctaagac agctggaaat   10560
agagaatgtc atggagcatt cctaaccatg ggctccagcc tggctttcat tctgtttctc   10620
ccctgaaaca acattccttt agtaatattc cgaataacag cttcatcagt ctgtctaccg   10680
accactcttc aggcttcatc ttatatgacc tcccaaactg cactaagggt tgtattagag   10740
aaaagtggat aaagttcgga gtcaggctgc ttgagcttaa atgccagctt cacttaccag   10800
ccacctgacc atgagtcagc tgcttaacca ttctttgcca cagtttcctt gtctatgaaa   10860
agggaaatgg ctcccacctc aaaaagttgt taacattaaa ttcaatcatg tattcaaagt   10920
cctgagcaga atgtctggcc atgactggga cttaacagat gttagcattt attattagta   10980
tctgtcagtc ttgaaatgtt ctcttccctt ggctttcatg acattccaca ctctcctggt   11040
tttctcttac ctctctggta atacctgttt gcttatcctt ctttgtccag ctctgggatg   11100
ttaccattcc ttcaggcgtg ctgttttctc cttaggcagt cttacacaca ctcatgactt   11160
ccttccattg tcctccacac actgatgacc ctaaaatcag tatctccagc ctaaaccttt   11220
ccactgagtt ctagacccat atgttgtact atcaacctgg cttgtccatt tgaatgtctt   11280
ccaggcactt cagactctct tctctagact ttgctggact ttcactcttc ccctaaaac   11340 tggctcctct tccactgaaa catgtatgtc attgagaggc accaccatcc acccagtgcc   11400
taagccagaa acctaggaat ccttgatacc tgttctctct catcctgcat atccaagcct   11460
atcagtttta tctctaaatt atattttggt aggtttactt cttcctttt ctcccaccac   11520 caccctgctc caagctacca tcatctcacc tggatgtctg caatagcctc atctcccaca   11580
gccactctgc acccctaat ctgttctcta tagagcagtt ggaaggagtg attttgttg   11640 tttgttttgt tttgttttag acagagtctc actctgttcc ccaaggctgg agtgcagtgg   11700
cacaatttcg gctcactgca acttctgcct cccgggttta agcaattctc ctgcctcagc   11760
ctcccaagta gctgggatta aggcaccggc cccataccc agctaatttt tatatttta   11820 gtagagatgg ggttttgcca tgttggccaa gctagtctcg aactcctgac ctcaagtgat   11880
ccacctgcct cggcctccca aagtgctggg attacaggtg tgagccactg cacctggctg   11940
gaaggagtga tcttaaaaaa aaaaaaaca aaaaaaaact tgactgtgtc actctgtgtt   12000
gtctctccta ccttgtatac ttccacaact tcccagtgtt cttggataaa gaccaaaatc   12060
cttaacttgg ccaggcgcgg tggctcacac ctatcatctc agcactttgg gaggccgagg   12120
caggcagatc atgaagtcaa gagattgaga ccatcctggc caacatggtg aaaccccatc   12180
tctactaaaa atacaaaaat tagctggtcg tggtggcgtg tgcctgtagt cccagctact   12240
tgggaggctg aggcaggaga atcacttgaa cctgggaggc agaggttgca gtgagcccag   12300
atcacgccac tgcactccag cctggtgaca gagtaagact ccatctcaaa aaaaaaaaa   12360 aaaaaaaaa ttccttaatt tggcctacag tagagccctc cgtaatgtgg cctctctcca   12420
catctccaca acctcctgct ccctgcactt cagcctcacc tctcttctgg acaggccctc   12480
cttctgacaa gggctttgtt cattctgctc cctctgccta gaatgccccc ttactctgtt   12540
cacttaactc ctgcttatcg tttagatctt tacctggatg gctcagagaa atatagaagt   12600
aattcctcac cctgaaaaat aggttaggtc cctgttttat gttttcatag accttccctt   12660
```

-continued

```
tgaggctttt tttaaaaaag tagtttaat  ctcacattta ttcatgtgat catctcctta   12720
atgatatctt aagacctcta atagaacaat ttggtcatgg actgtggggt ttttgcccct   12780
cattgtgtca gcactgagca tattgttggc ataggaggga tatttgttga atgaattgct   12840
agaggtggcc aagagatatg atgtaagtca ggcttttccc tgcccttccc cttccccttc   12900
cccacatcct tcctatagca gccaccgtgg ctgcagttac tgtaaatggc aagacggaat   12960
cagttccgga cattgggttg ttttagaaaa ttgcctgcaa gtgtcagggt gataagttaa   13020
agctttgtct tttgccctca gaggagctat cccatagtga gtagaagcca gagaagctga   13080
ccccaggagt ccttctttcc agcagcaggt cttgagctgc acttctctgt agctacaatc   13140
caggcaggaa caagccctag gtacctccgg agaggagggc aagagaggaa gaatgagttc   13200
agctactcta gccaccaaac tgattatgaa ttgccctgaa atctgaaaaa tttcaattcc   13260
aatcgtaagt ttgttttgtt tcattttgtt ttcttaaatt gtatatttga aagatggcat   13320
taactaaaga tatatattca atatagagtg gaaaaaatgg aatacttgca tagtatcttt   13380
tacttatagg tgatttatga tggggagtgg ggtggatagg ttggcagttc ccccaagaag   13440
ttggaaatga agtttgtcct ctgtgagttg aactaattag atccacaagt aatgaaagca   13500
gtattgtgtt gtagttaaga gcacactcta gaaccagatt gcttagtttc aaatcctggt   13560
tctgcctttt attatctgtg tactttgggc aagttacttg ccctttgtgt gcttcatttt   13620
tctcatctag aaaatggaga ggccaggcgt agtggctcat gcctataatc ccagcacttt   13680
gggaggccga ggcgggcaga tcacctgagg tgagaagttc aagaccagcc tggccaacat   13740
ggtgaaaccc tgtctctaca aaatacaaaa aattagccag gcatgatggc gggtgcctgt   13800
aatcccagct acccaggagc ctgaggcggg agaaacactt gaacctggaa ggcagaggtt   13860
gtagtgagcc aggattgcac cactgcactc cagcctgggt gacaagagct agactcagtc   13920
taaaaaaaaa aaaaaaaaac aaactggaga tacaggctgg gtgcagggct tacacttata   13980
atatcagcac tttgggaggc ctaggcggga ggattgcttg aactcaggag tttcaagatc   14040
agtctgggta acagagcaag acctcatccc cacaaaaaat caaaaattta gccaggcatg   14100
gtggctcatg cctgtggtcc cagctactca ggaggctgag gcgagaggat gcttgagcc    14160 caggaggttg aggctgcagt gaaccatgac tgcaccacta catgccagcc tggatgacag   14220
agcaagaccc tatctcaaaa aaaaaaaaa  aaagaaacga gccaggcgcg tttgctcacg   14280
ccagtaatcc cagcactttg ggaggccaag gcaggtggat cacttgaggt caggagatcg   14340
agactagcct ggccaacatg gtgaaacccc atctcaactg aaaatacaaa aattagccag   14400
gcatggtggc atgctcctgt agtcccagct actcacttgg aggctgaggc acgagaatcg   14460
cttgaaccca ggaggcggag gttgcagtgg gccaacatca tgtcactgca ctccagcctg   14520
ggagacagag cgagactctg tctcaataaa taaataaaca taaaataaaa taaaataaaa   14580
taaaataaaa taaaaaaata tggaggccag caggcacggt ggctcacgca tgtaatccca   14640
gcactttggg aggccgaggg gggcggatca caaggtcagg agatcgagac catcctggct   14700
aacacagtga aaccgcgtct ctactaaaaa tacacaaaat tagccaggca tggtggcagg   14760
cacctgtagt ccctgctact caggaggctg aggcaggaga atggcgtgaa cccgggaggc   14820
ggagcttgca gtgagctgag atcgcgccac tgcagtccag cctgggcgac agagcaagac   14880
tctgtctcaa aaaaaaaaa  aaaaatggag gttgggcgcg gtggctcgcg cctgtaatcc   14940
cagcactttg ggaggtcgag gcgggcggat cacctgaggt caggagttcc agaccagcct   15000
ggccaacatg gtgaaacctt gtctctacta aaattacaaa aattagccag gcacgatggc   15060
```

```
aggcacctgt aatcccagct acttaggaga ctaaggcagg agaatagctt gaacctggga    15120
gatggaggtt gcagtgtgct gagatcgcgc cactgccctc cagtagagtg agattccgtc    15180
tcaaaaaaaa aaaaaagaa gaaatggaga tacaaactta ctacctacct ccttacaacc     15240
taccctcaca gtattactgt gaataaaagt gtgtgtagca ctgggaacac tattcacaga    15300
gcactcatga atgtttgttc tttgttatta gttactagag aggcaaatgt ctgccagggc    15360
tgaataatat gtgtgaattg gtgattgtcg cacatatcta aagaagtagt tatttttttc    15420
aattaaaact tagtttaaaa accaatataa ggccgagcgc agtggctcac acctgtaatc    15480
ccagcacttt gggaggccga ggtgggcaga tcatttgagg tcaggagttc gagactagcc    15540
tggccaacat ggtgaaaccc tgtctctgct aaaaaaaaaa aaaagtaca aaattagcc      15600 aggcatgatg gcaggtccct gtaatcccag ctacttggga ggccgaggca ggagaattgc    15660
ttgaacccag gaggtggagg ttgtagtgag ccgagtttgt gccactgcac ttcagcctgg    15720
gtgacagagg gagacactgt ctcaaaaaaa aaaaaaaaa accaaaacca atataataaa     15780
taagtggcca gcaatgaaac agaaagtgaa agttagtga agcaaaacta gtactgtatt     15840
cagataaaga tgctgaatct agatttggtc accagaatag ggtcctttgt ggcaacctgg    15900
gctagtttgg ctgactcacc actgccagga tgaaatttct ttcagtggct actcatttcc    15960 cttttatttta agtccatgct cacagagcaa ccttctgatg cctaattcag cttcctggga   16020
tacttaataa caggaagggt ctggaagtag tacctgtata ggggatatga gtgttctgat    16080
tttaatagtc aattcataag tgtacagagg gtttgataaa tggttaggtc agaaccatca    16140
cagaatgtct acacctcttt ggacattagg aaggtcaaaa acctgaaagg ccaaaagcta    16200
ggcctagatt agggtcattc accaagaaaa catcagcctt gaagagttct ctgggtggtc    16260
caccagtcaa ccttcctttg atcacacctc cttcctcgtt gcttctttaa gcattgacct    16320
gtaatgggta tggaatttttt tgctcaccta actccttcct tttacagagg aagaagttga    16380
agcccagaga gatttaatgg cttgcctaag atcacacgca gattttctgt taaccagggt    16440
gatttttcag gtgttccctg ccagacgagg gctttttcc ttgaattgcc tagagatttc     16500
ttgagatatc cgaagcattt tcccagtgc agcctggaga aggatgtccc tgtcaacaca    16560
gcatttgtta ctcaatgtta gacattcaat tttctaatta gtatcatgga gcaacagtgg    16620
atgattatct ataaggggtt gcaattccat gcttatgtgc ttacagccca tatagacaaa   16680
tatcagctgt taaaatgaca aggcagtaga gatgtggccc caggacaaag gcatactctg    16740
ctgttagtga acactagttg gccagcaaat ttcacatggg catatacacg gccaactgta   16800
gactttaggc atttataccc attcagagag ccaaactggc aactaaagat cagcattctc    16860
tttggcattt cagctttgcg ttctgttaaa aatcactgct tgcttaaata cctctgatag    16920
ctcttcactg cctgtaggca actctttagc ctagcagact tggtctttag tgctctgccc    16980
ctactctctt ccaccattct ggcctcctgt ctaattgctg cccatatgtg ccatgcacta    17040
gagcttacag acctgctcag cgttatatga gcataccata ctctttatgc ctcagtgcat    17100
ttgcacatgt tgttccttca ggccagaatg cctgttactg cctggcaatc agcctattag    17160
agtctgccaa taccatccca tcttctgtgg aggagccccc cgccaaatcc acccatacct    17220
ctccccacca atcagagact tcttctctct tgttattct cttcgttatt ctcttcatac     17280
ctcagttata tccatttcag tatttgttta cacatctagc atcactctta gagtgtgaaa    17340
ttctccaagt gtggagccgt atctagtttg tctttgtatc ccagagctta gcaaagtgcc    17400
```

```
tagaatgtag tgggtgctca gagtgtttgc tgggtgaatg atgtatttgt tgaacgactc   17460
tttggacact tgaataaagt ccatccagta tgcaccatta ccatctcttc gctctacaat   17520
attcttttag gcaagagctt atcttttgag gtgataagat aagctcaaac ttatgtagac   17580
taagacctca gtctgtaaat gtcatccctc agtcttaaac catcaaaacc agggcctcaa   17640
ggaatggcat gccttctgca actgtagcaa cctgctgtgc ttattttgcc gtgttttca    17700 ttttttcccc aaaagctaga gtcccttctc ccatgggcag tgctggaagt gtgctaacaa   17760 attcttctc catactgctt acgattacaa aaaaaccct cagcatctca tgccagactt     17820
gagttaaggt tgttttcttt tgtgtgtcag ctgtattctg gtcatgactt cctgatgatg   17880
ccctatagag attttgctga gatcagaggg tgctccactg ccatcagtag cactgactct   17940
tgcagaagca ccgtttctga agttggctaa tgtcatccct cacgtttgtt tgtttgaaat   18000
ttgttttagt tccagagata gcactttcat ggaatgacgc tatcttctag aatcactttt   18060
tttttttttt tgagttggag tctcgctgtg tcgccaggct ggagtgcagt ggcacaatct   18120
cagctcactg caatctccac cttccgggtt caagtgattc ccctgcctca gcctcccgag   18180
gagctgttac tacaggcgca cacccccact cctggctaat tttatgtgtt ttagtagaga   18240
cggggtttca ccgtgttggc caggatggtc tcgatctcct gactttgtga tctgcctgct   18300
tcagcctccc aaagtgctgg gattacaggt gtgagtcacc gcgcctggcc tagaatcacc   18360
tttttatacc ataacgtgag caccactgcc gcgtcaccaa ggaaagagag aggcagctac   18420
tgtggggtta caaatgggta agagtggcac caggaaggtg aaagtctcta cttagccaag   18480
gcttaacaaa atgtcaatca ccaaacattt atttattaag ctacgttcag gataagaaga   18540
tgaacaagct atctgtacat tcattttctc gtttgtaaca aggtaatgat agtgatctat   18600
cctgcctgcc tctgagggtt attgtgagaa taaaatgaaa tcaagtggaa aagcacttag   18660
gaaaaagaaa agcattggtt ttcaattgtt agtgtggatc agaaacactg gggcttgttt   18720
aaaatgcaga ttcttagccc cagtctcagc gattctgatt ctgtatatct gaagtgggac   18780
tcaggaatct tgattttcaa caagctgacc agagggtcca atgctgctat tcctttagtt   18840
acactttcag aaatattact gtaaatcaaa tggcaagaat aaaatagtta tttgaggcag   18900
ttttagtatg ttggacctgg agtccaaaga cttgggtcaa actccagctt tgtcagttcc   18960
tagacctgtg accttaaaca gcaaccttct ctgtgaacct tagttccctc aggaacggct   19020
ctggtcacct cctgctgtac tccattgatg actcaccaca taaggctccc tgggagtccc   19080
ccaaaccttt gctctcttaa ctccttttac agcctcctac atctcctgca ggtgctgtct   19140
tctcctcctt tttccaggcc ctgctctgac acagcattca ttctcctctg ggaagggttc   19200
cttcaatgtg tctccaagca catcacaccc aggaaggacc ctgtggccat atctgtctat   19260
caccagatca aactacgtga aggcaggcac taggtactgt cagtgcccag cataggcctg   19320
gcccatacca ggtgtccaca gatgcctagt aaagaaacct atgattcagg accccccatga  19380 tgagcaacta tagcactaga acagtgataa taactaatgt ttataatgca tcttcagttt   19440
acagagggct tttgtactca tcatctagtt tagttcctgc aacaacctct tgaggaatat    19500
agcacaagca ggacaaggga agcccagaga tgttaaataa tttatccaag tttatgctgc   19560
tgggaagggc agcactgaaa ttaaaagaaa agttttctga gctcaaatcc catgcccttt   19620
cctcaatgtg agctctagca aggtattcag gaatcctgcc tctacagttc agagcctcaa   19680
attgctgggt atgttgagtt cttgtatctg atttttctag atttcctgcc cacattctta   19740
ctgtctggat atcaggaaag agtttatcaa atgcctgtgg aaatccaaga taaggtctca   19800
```

```
tgatgagtaa cccagtgaaa acatgaagtc aagtctaact agtcactact atttcactac   19860
tgctgactcc tgatgatcag ctcctttct aagtgcttac tgtccactta ttccatcatc    19920
tgcctagaat ttatgtgaag gaatcaaagc aaaaggatca taaggcttcc ttttttccagt  19980 atgttttcc tcctttttga aaactgggcc agttagctat ctccattttt atttcatgaa    20040
tacatcccca gcgcctggta tatagtagat atggaacatt acactttgga gatattgcac   20100
ccattctcca gtttctccaa agttactaac aatggttcca tcactgtgcc aacatatttt   20160
cttttttcaa tatattggga aataattctc ccagtctgaa atctgaaca catttcatgt    20220 gacttggtat cctcatatgt cttgggcttc caattctcca ttcctagttt caagttcatg   20280
aactgtaaaa caaaggatta gactaaatct ctaaagttct atccagatgc caaattcttt   20340
tctctttcca tgatacctaa gatagatgcc aaatattgtc ttttacctgg tgtttgtgaa   20400
catgacatca cattacagga gtagcagata ctaaactctc actctgtaaa acactgactg   20460
agttccatga gccagatact gaagtgagct tgttcacata tgttctcatt taatgctcat   20520
aaccctgtga agctgggaat tgctgggaca ttttatttat ttatttattg agacggagtc   20580
tggctctgtc acctaggctg gtgtgcaatg gcatgatctt ggctcaccgc aacctccgcc   20640
tcccgggttc aagcgattct cttgcctcag cctccgcagt agctgggatt acggggcaca   20700
caccaccaca tccagctaat tttgtatttt tagcagagat ggagtttctc catgttggcc   20760
aggttggtca cgaacacttg acctcaagtg atctgcctgc ctcagcctcc caaagtgctg   20820
ggattacagg catgagccac catgcctgcc cgggacccct gttttagaag gatgactgct   20880
gctataatgt agaaagtgat ttggaagagg ggaggagtgg ggcacgaaag atggttagta   20940
gatgggggtg gtaatgctta cctttcagta tttggaggct tcggagtcct caaaaattct   21000
cttccttgat tggagtcctc ccagccaata gagggcttca cacaaacagt ttcttgggtt   21060
ttgaattgtt tgaccagagc tttcttccga caaaaggttg gggtgattca ttcacttacc   21120
acaccttgcc tgaacattca cttggggctg ccggttatga aggctattgt tctccagcct   21180
gtcacagacg ctttgaagac ctgtgcctca gctggttcta aggagtcagt ttgttcagct   21240
ccgtgccagg tttccaactt atgaaatgtg ctggagatta cacctctcc tgccattta    21300 tccctactat aattgccagt caaaggattc ctgcagttgc ctctggcagc cataactgat   21360
gaatgttctg ccagctgctc tgaggaccta gaagagcagt tttctatcca ggaccagttt   21420
ccaagggtgg gagggtgaaa tatatcctcc agtgtgacat ttcatctccc agtgatgggt   21480
ggcttgggcc ctttgaagtt ggctctgagg aaccacacac ttgggtctga gcagccagca   21540
gcttatcaca tctggtgatc aatccttcaa aggttcctcc tgaagtctga attttttggag 21600 gtcaaatgga ttccacctgg gaggggcttc tgcttcaact caggacatgg ggagaaggct   21660
gttcctcttc caggggggagg cagttttcat ggcattgaga tgtcctctca cttattcccc  21720
acccacccac caagtccttt gtaagaggag taggggggaga ggagagcgcc tgcagcctcc  21780
tgctcacatt cctagacacc gactcactga gcccgtcgcc gctggaacag cagagctgtg   21840
tgaaatgtca agaggagtta tgctcatagg ctccctggcc tcagtctctt tgtggcttgc   21900
atattcttcc attagtactg tgttcatcac atggaaatca gagggtacaa ttaaaagata   21960
atttgctagt cccagactta atttggggcc cccttcttgc ctgattgaat tacaggggaa   22020
cataatagat ttttggtgag aaatagttgt ctgtgtggct gggagaaaga ttgctcccag   22080
ctctccagct gggcagccct ttcagtatcc cgtatgttat ttccccactt ccagcccacc   22140
```

```
tcacctcctc tgtggccctt gtgtgtcccc tcggctagga tcctgacctc ctgctcaaga    22200
gtttaaactc aacttgagac ccaaggaaaa tagagagccc tctgcaacct catagggtg     22260 aaaaatgttg atgctgggag ctatttagag acctaaccaa ggcccagaca gagagagtga    22320
cttgctaaag gccacatagc tagcccacag tagttgtaac aatagtctta atgatattaa    22380
tggctaacat ttatcaacct ttaatgtgtc ccagactttg tgccaagggc ttacatgcag    22440
tgcattgtcg cattcaaacc cagacagtct ggctctgggc ccaggctgag ctttggtata    22500
gcatggtaga acgttgtcta taatgtctag tctgggttca aatcctggct tcacttctca    22560
catttacagc tgagtgacct caggcaagtg atttaacctc cctgtacctc agttgcttta    22620
tctgtaaaga gaaaaatcac agcactgtgg aatagtgggg gttaaaattc attcatacaa    22680
gtagtgctgc aagcaatgtt taatacaggg tgagcacctg ttcagtgctt ccttcttctg    22740
gctgcctctg gggctagagt gtggtgtctt cgtggtatag atagatagat atggctgagc    22800
tctgcacaaa caccaagagc tgttcttcac tattagaggt agtaaacaga gtggttgagc    22860
tctgtggttc tagaacagag gccggcaagc tatgggccat tgcctatttt aatacggcct    22920
gtgattgatt gattttttt ttcttttga dacagagttt cactcttgtt gcccaggctg      22980
gaatgcaatg gcacgaactc agctcaccgc aacctctgcc tcctgggttc aagcgattct    23040
cctgtctcag cctctcgagt agctgggatt acaggcatgt gccaccacgc ctggctaatt    23100
tttgtatttt tagtagagac agggtttctc catgttggtc aggctagtct cgaacttcca    23160
acctcaggtg atctgcccgc ctcagccttc caaagtgctg ggattacagg cgtgagccac    23220
catgactggc ctgattgact gatttttta gtagagatag ggtcttggtt tgttacccag     23280
gctggtctca aacttctggc ttcaagcagt cctccctcct tggcctctcg aatgctggga    23340
ttataggcat gagccactat gcctggccta tatgacctgt gatttttaat ggttagggga    23400 aaaaagcaa aagaatgctt tgtgacatgt ggaaattaca tgaaactcaa atatcagtgt      23460
cccagcctgg gcaacaaagt gagaccctgt ctctacaaaa aataaaaaaa aataagccag    23520
ggccgggcgc agtggctcac acctataatc tcagcacttt gggaggccga ggcaagtgga    23580
tcacctgagg tcaggagttc aagaccagcc tgaccaatat ggtgaaaccc tgtctgtact    23640
aaaaacacaa aaattagccg agcatggtgg catgcgcctg tagtcccagc tacttgggag    23700
gctgagacaa gagaattgct tgaacctggg aggcggaggt tgcagtgagc caagatcgcg    23760
acactacact gcagcctggg caacagacg agactccgac acacgcacgc acgcacacac     23820
acacacacac acacacacac acgctgggta tggtggccag cacgtgtggt cccaggatgc    23880
actggaggct taggtaggag gatcacttga gcttaggtgg ttgagactac aatgaaccat    23940
gtttatacca ctgcactta gccagggcaa cagtgtgaga ctgaatctca aaagaaaaaa     24000 aaaaaaaga aaaaatctt tccataagta aatatctgtt ggaacatagc catgtccctt      24060
agtttatgtt ttatatatgg ctgcttttgc cctataatga cacaattgag tggccacgac    24120
agtctgtatg gcctgcagag cctaagatat ttgctctctg gcccttaca gaaaaagtgc     24180 cttgacctgt gctctagagc catatgtacc aggtttgaaa ctcagcctca cagctgggtg    24240
tgatggcacg catctgtagt cccagctact ctggaggctg aggtgagagg atcacttgag    24300
tccagaaggt cgaggtcaag attgtagtga gccatgatgg catcaccgca ctccagcctg    24360
agtgacagag agagccctg actcaaaaaa aaaaaacaa aaaaaaaaa caccctcacc       24420 acttatcagc tatttgtctt gagaatagtg acataacccc tcagaaccta tttcctaatc    24480
tgttaaatga ggctgatgac gtttcctcct tttactggca atttaaacat gatggataat    24540
```

```
aaatgctaag cacttaacac agggcctaga agatattaac tgctcaataa atggtagctt   24600
cttaacagta ttcaaaccca tgtgctctta tcacatgcat tgttgtccct gtgtccagtt   24660
ggtggaatgg gaaaaggctc ccttgtaacc ccatctacca tctttatcag actttcctgc   24720
catggttcac agtaagagat agaagctgca cggtgacttc tggctcttta caatggtgag   24780
cggtgtgtgc ctggtaaggg agagctgatg tcactgcccc aaatccagta gtgagatctg   24840
agtgttctgg tttcctccag cagccttgct ttttccttta caatcctgca ggcagggaga   24900
caagggcttt ctacatggta ggctctggtt tggtcatcgt cacaactggg ggctgttcag   24960
gtgggctccc attccagata cctaggctta tcaatccctt ttggcacccc aggcctttt    25020 ctccctcatg ccccattttt cagtttgaaa agcatggtta tcacaggaca agtagaagaa   25080
gctccactgt ccactgaggc caatggatgg tgttctgcat gtgaacactc agtgaatagt   25140
gagtgaatga gagtaacctg ggctccatcc tatttgcaga gagctttgga aaagattttt   25200
ctccttaaag agccagaatg aagcctggta gtgggagagc tccagctcta gagtcacatg   25260
agcctacatt taaattccag ccctgccact gactcccttt tgaccttga gtgagttacc    25320 taatctctct gtacctcact tttcttgtct gtagagtggg aataattcct gtctcagaga   25380
aataaaagag tgcatatagt gtttgccaca tggagacaca tcaggtgtag gttaatactc   25440
tgggccttgt ttccttattt gcaacacagc cctgccctgg agtggaagtg gcacctccca   25500
ttggtcagct cttgaggctg tccccaggac aggcagaggg agggaatgaa tgggagccct   25560
agtgccagga cagaacagat ggcagctcag agctaggatg gctctctgga cctgtctctc   25620
ctaccagagg tcccccgtc tggtgtggct cttcctggac ctggcatcct ctgctttttt    25680 ttttttttcca cctccaagca gaattactgt cctgtaggca gctcctctgc ttgaggacat   25740
ctggggccag atatgttcac actctatcct gccttgccct tccctgagct caggatggac   25800
gctcaattgg tcccagttat tgtctgcagc gcctgcctgc agcctcgatc cagcccagct   25860
ccaccccttg cctgcaaggt ctgtttccta acagctgctc caaccacaca cctcggttct   25920
gcgggagccc ctcctcttcc tccctccctc cctcattcag gggtgggact gaagaagaag   25980
gctaacttga cagcagcgct tctttcttag ctagtcaccg gccctgctc aagaatgcca    26040 gtgtgtgtgt agcctccaca gagaggtcgt tttctcggag tccagagggg ccgcctgagc   26100
ttctgagaac tagggaggag ccatcccagc catgagcccc tgtgggaatc tgctgggggc   26160
caagtggcct ggagtcctca ggctcccgca gctgctccgg agggagaggt gagctcaggg   26220
cagcctgcct gcagccagag gtgccggag ccccgggcct gtcatggtgg ccatctacag    26280
ccggcctgag gcagtcacag acggatttgc agctgagcct gtctatctgg tgtgggaaga   26340
agatggggag ttacttgtca gtcccggctt acttcacctc cagagacctg tttcggtgag   26400
ttggtctccg agttcccctc tccatctctc ctggcccctg gtcctgagag gagggtggtc   26460
tccctaaatc tccttctcac ttagtccttt accatcggtt ctgccgggca gaagccagcg   26520
gaggttatac ccaaggagaa tcggccttgt gaggtacccc cattatgtcc tggaagtggt   26580
gaggggaggg atatacccag aaggaacttc ttagggagct ccagctcccc ttctatccca   26640
gacaaacctg aaggagcctc caaaagatgc cactgacctg cccattgtag atgttactgc   26700
ttccgggggg aatagcccaa atagagtgct gtttccagct ctcacatgtc ttacctgcgg   26760
gccatgctgc ctgcccagga atttgtccca acaagcagga tgggcaggtt ttgccaaact   26820
gtggaaactg gcaagtcctg ggtgtgggta gcctggtaca cagtaggcac cttataaacg   26880
```

```
tttgttctct taatggcagg cacatttgcc tctggccttg aagggcttct gagctcccag   26940
gtgaatgtag ttgctgggga agacctgggc cgagtgcttc taagactgga gcaatgggct   27000
ttagagtgtt cctgagctgc tgggccagcc cccacacctc ctcagtccct aggcctaagt   27060
acctccacga gcctctctct gtggggcttc tcagagggag atgtggaaac tctacctcta   27120
acctggcttt ctttgctcat tgccccactc cacctcccat agaaactccc caggggcttt   27180
ctggccctct gggtcccttc tgaatggagc cattccaggc tagggtgggg tttgttttca   27240
ttctttggga gcagcctgtt gttccaaaaa ggctgcctcc ccctcaccag tggtcctggt   27300 cgactttcc cttctggctt ctctaagcta ggtccagtgc ccagatcttg ctgccgggat    27360
actagtcagg tggccaggcc ctgggcagaa aagcagtgta ccatgtggtt ttgtggaatg   27420
accggaccct ggtagattgc tgggaagtgt ctggacaggg ggaaggggga agggaactgg   27480
tcctcaatgc tgactctacc aagcgccctg ctagacactt tatcctttaa tctctcaaca   27540
gcctaaagag attatatatc cccatttttac agatgaggca accagtttca acagagttaa   27600
catatggagc ctcactgggc agcttttct gtcttcctga cttctctca tccttcaggg     27660 ggctgcaggt ttgttttctt ctcctagtgg agaggaaatt ctcaggtttg ttttcctctc   27720
ctagcagaga gtaaaaaaag ggatagtttg cctgacttgt tgaaggtgtg gctgagattg   27780
ttttctaaag agccaatgga aattgatctt gagtttagga gaaagctttt acatgtggaa   27840
ttaagatgcc aagtgttgaa gtagccacat ttcaggtcct cattaatttc tcttaatcct   27900
gggaaggcag cttaggagaa gggttgttcc tttaggagcc aggaactata cccctttac    27960 ccttggagag gcagggaagc cagggaggac acaacttctc aggaagagga gaagctagag   28020
cagatagtga actctcaacc tgaacctta agggccagac cactaatgcc acccaagtcc    28080
acctgccgtt tgtcttgttc tgtcccaggc tttctggaga acctgatctt cttgccccta   28140 ccccaagct ccgtttgccc agctagagtc tgggggtac tgactgactt tcgtagacat     28200
tcttcccttc cccaaataag aggccacatt cctgaagtca cttctgaaga gatagctgcc   28260
acacagggct ctttccccccc agggagggac cacccagacc ctctgctctc ccaggtatcc  28320
gttaccacat cactacctgg tcagaaagct gtttctgcca ttagcccctc cctctttat    28380 tataggatat cctcaagggc tcctctttgg gcctcagttt catccttggc agaaagtaga   28440
agctagactt cttgggctcc tgaacagggt ccttgctgga ttctgtgaaa caaattaagt   28500
tcttgaccct aggcctctgg gggagtacaa agtctatggg agttctgggg ctgtggttgc   28560
aaggaaagtg acgcaaccag attccatggg gacatgatca ggcgtgacat gtgagggagg   28620
aagagggagc aagggaatga agaatacaac ttctgtgtcc catacacccc tgcctgacag   28680
gccatacata ctcagcagag aatgcactgt cttcctacc acactagcgt gaggagtgag    28740
ctgcaattac cactgtgctt ccaagtaaga aaatacctca aattggaatt tacaaaagag   28800
gtaaattagg gagtggcttt tgtcggacat ctttaaagca ttttctttt tatagaattt    28860 cacttaatgt ccaatactga tttaatgagc ttgggtttac acattatctc ttgaagaaaa   28920
caaatgaacc tttgtgttcc aaagcaatcc atgtttaaag ggaaaaaatt atgcataact   28980
ctgcccagct tcacagtaac ctttggcagg tgccttaggt cctctgggac tcttttcctt   29040
atctgaaaaa tgaaggactt ggatcaggtg aatggttccc agctctgcaa cttatgtggc   29100
tcctcagagg cacacaagct cttttccatt atttgccaaa taatgaggc cctgtctta     29160 actgcagtac aactacacaa aatacttgaa actacagtct tcctggtttt tggttggaac   29220
tgaatcagtg cactctagca acacttattt cttgctgttc gtaggcttca ttatgtgttt   29280
```

```
ggttaatttt ttaaaacaac aataacatat tccataataa ttacagctta attggcagac  29340
tgtttcagtc tataggatct gcaggaagga ggagtaataa agggattttt gactgagctc  29400
ttatggaaca gagtctctct aggcccctgt catatctgcc cttctgggcc ctggggaaaa  29460
gttggcatcc ccagttgtgg tgctctccag gtgccctcag gctgtggtgg agggagcttc  29520
ccattctctc cttcagccca ctcaattcag aggctagggc tgaaagaag cttctctaca  29580 actggctgtt cactgggagg ttaagggatg accatccagc caggccttcc tcaggacatg  29640
ggagggctta tgctttaaca tgtgtaaatc cactgcaata atgactggtt cttttacccc  29700
ataaggttga gaatttacct gtaaacattt ttgtctgaag aatttggatg taagtgaggg  29760
ctgggcctct atcttatctc acttggcttc tctcagcaca gcaccttgcc tgcttgttct  29820
tacacatcct agatgcacag taactatttc ctaattatta gaaatctatt agaatcaatt  29880
gatttcagct gggcttggtg gctccttcct gtaatcccag cactttggga ggctaaggct  29940
ggaggatcac ctgagtccag gagtttaaga ccagcctggg caacataggg agaccctgtc  30000
tctacaaaaa ataaaaaatt agccaggcat ggtggtgtgc acctgtagtc ccagctactc  30060
aggaggctga ggcaggagga tctcttgagc ctgggaggtc agactacagt gagcaatgat  30120
tgtgccactg cactccagcc tgggtgacag agtaagactc tgtctcttaa aaaaaaaaa  30180 aaaaagttg atttctattt ggatagataa ataattcatt ttaggacctt tcttttttcac  30240 ttacagaaat ctgtttcatt ctgggctgag aagcaggtcc atattgctag cataggaga  30300 aaaagggggtc tgtctgcatt tgcccttggt ggtctcaaat tggggaggga aagaaatgaa  30360
cacttactgg ctaccttctg tgagccaggc atcatgcaag acatctgtac ataatttaat  30420
tctcataacc ccataagata ttattagcaa tgtacaagtg aggaaactga ggctcagagt  30480
catgaagtaa ctggccttgg gtgacacaga tggtaaatgg cagagaagga atatggatcc  30540
aggtcttgaa agagaaaatc tcaactgatt atctttttta aaaactcat atgttctctg  30600 ctgactcaaa aggtctctgt gtggatctgg gttgacccac tgaactgacc atcagggttc  30660
catgcacttt gtatctgccc aagccctcag aacccctcag taatgttttg gaagatgagt  30720
tttggaggtt gtccttaggc atagcctcag cgtatgtagg cctctaggtg atctccccta  30780
acctgaggat ttcagctcaa ttcactctgg ctcctcagga cagtgggatg actggttcag  30840
acctcagctt taccacctcc cagctgggta ctcttctacc tacagccagg gcagattttg  30900
actttcactt gaaacttcca aaaattgaaa ggtagaaaaa cagccttggc tttgggaaga  30960
acgtatgatg tccatggcct ctaagcatct gaggtgggac atgttcgagt agcaccttac  31020
agttccaaag tgtgttctgg gttctttgtt taaagaaca gagactgctg gggaattgaa  31080
cactgtgaag tatatgaagg aggagaattg tgctatttaa cattcagtac ttgggctaaa  31140
ggagaagcat cacgaagtgt taacactcaa agggtcttga gctgtcaggg ctccagcttc  31200
cttattttca caggtgagaa tcctgaggct cagctgttga gatgtgctgt ctcactccgg  31260
tgacatagta cagtggatgt ggctttgcag ccaagcacac atagcttcac attccagctc  31320
catcaattat gtattgggca gctttgcaga atgatttgac tttaactctg cttttcagtc  31380
ttctgtaaaa cagggataat cctgctaccg taggggttgtc aggattagag ataatataaa  31440
taaggtacct catataggac ctggattatg gctggcattc aataaatagt agctgttaat  31500
tgatagctaa gctagaactc tgaagtctac catggcaact tcttaagtgg tctgagaacc  31560
cagttgtgtt ctgtggcaaa acacagctta gggatccata cccagccctc ctgtcagctg  31620
```

-continued

```
ttcaccttcc agttcttcag agacatgtgt ggcagtgact ttggccacat agctggctgt   31680 gcccttttaaa ggcattcctt gacacagata tgtggactgg tgacgttgct ctccagccag  31740
gtgttcttcc cagcaggctg gcctggctgt ctcctgcatg cctgtacttg tttgtctccc   31800
tgctccctct cctgggcctg gccagagcta cttgcagcaa acaaaagcag gatattggca   31860
atggaaagga gggtgtgttc tggtgctccc atgccctgcg gcgcacatac cattgcaagg   31920
gcgtaacaga gcccaggcct gcatttgggt gcaaataagt ctgcacacag aagaaaagaa   31980
ggacctggtg accaggagcc atggaaccct tgtgctcccc tacctgggct actggttctt   32040
gccactccta ccattttcag tttggaaata tttgttaagg ctttgctctt ccaggtcctt   32100
tgcttggtgc tgagtctacc aagagtaagt gggatgctgt ttttgtcctc agggagctaa   32160
cagtctagtg aagaagaaag atggttgccc aggaacttct aagtcagaag gcaggaggca   32220
agaaggaagc ccctgctcct actgccagcc ctctgttggg cacccatag ttcttcagaa    32280 ccacatttaa tcctcactgc aggccaggca tagtggctca cacctgtaat cgcagcactt   32340
cgggaggcca aggcgggcag atcacttgag gtcgggagtt cgagaccagc ctcaccaaca   32400
tggggaaacc ccgtctctac taaaaataga aaaattagcc gggtgtggtg gcatgcgcca   32460
gtaatcccag ctactcagga ggctgaggtg ggaaaatcac ttgaactcgg gaagcagagg   32520
ttgcagtgag ccgagattgt gccactgcac tccagcctgg gcgataagag caaaattcca   32580
tctcaaaaaa aaaagaaaa aagaaaaaat cctcactgct accttgaaag taggtgatga    32640
cattgccatt tcacaaatga gaagtgaagg ggctagccca agatcactta ggtggtaaat   32700
ggtggtgcta agattagaac ctcagatcat ctagggaaaa acacagatat gcacagagtt   32760
aaggggaccc agggtattgt ttgtcctctt gtttcacagg tggggaaaca acccagagag   32820 ggaaagggc ttgtccaagg caatttagca cccaagaact tgaacccata tctctctcct    32880
cctcatttag agctcatccc acatgtatct tatattgaga ggagtgtgag ccacatacca   32940
agaacagtct tcccctctgc ctccaacctc actgtgcagt tttgagacac ttcacagcca   33000
tactcttcat gccatacccca gcccttaaga ccctgaagtt cccccttccat aagacaagta  33060 ggaaaagcta tagggtaaaa atagccatca gtgtttgttg agcacccagg aggaattggg   33120
cactccagaa agataaaggg attctcaggg acttgcttct ctagacttcc ctagctcagc   33180
tgcttcaact cattcctgcc cctcttctct acctcccgca gtgctcagaa gtagtagaac   33240
tcactgtggc ctctcacctt gcattgttga gttttattta gactttctct tcctcaactc   33300
ttcataagct catgaaaggt gaagtagggt gccctgtgta tttatctttt atatctgcag   33360
tgcttagcaa gttataataa tgcacttgcc tggcaaaagg ctttctctca tacattagct   33420
tatttcctct tcacattggc tctttgtagt aataggatgc tattagttat tttcaatgag   33480
agaaagctac taagagaagt tgtccagcta gtgacagtaa gtggctgata aagtgagctg   33540
ccattacatt gtcatcatct ttaatagaag ttaacacata ctgagtttct actatattgg   33600 gtctttttt tttttttttt tttttttta gagacggaat cttgctctgt tgtccaggct      33660
ggaacgcagt ggtgcaattt tgggtcacca caacctccgc ttcccaggtt caagcgattc   33720
tcctgcctca gcctcctgag tagctgggac taccagtgca cgccaccacg cccggctaat   33780
ttttgtattt ttagtagaga cagggtttca ccatgttggc caggctggtc ttgaactcct   33840
gaccttgtga tctgcccgcc tcagcctccc aaagtgctgg gattacaggt gtgagccacc   33900
gcgccctgcc tatattagga cttttatata agctatctct agctagctag ctagctagct   33960
ataatgtttt ttgagacaga gtctgactct gtcacccagg ctggagtgca gtggcgtgat   34020
```

```
ctcgactcac tgcaacctcc acctcctggg ttccagtgat tctcctgcct cagcctcccg    34080
agtagctggg attataggtg catgccacca cgcccagcta atttttttgta tttttagtag    34140 accaggtttc accatgttgg ccaggctggt ctcgaactcc tgacttcaag tgatccaccc    34200
gcctcggcct cccaaagtgc tgggattata agcataagcc actgtgccca gctgctctct    34260
atatttttaa tacatattat ttccattaat tttcacagca gttcatttta tagatgagga    34320
aactaggcca gagaagtaaa atatcttgcc caagatgatg taactagtaa gtggcaggat    34380
caagattcaa accaagcaat gttcaaacct cttggaagca agaatgtggc cactgtggaa    34440
ggtgcaaggc cttgacaaca agaataggga aaagaaggaa ctagaaggaa agagatggca    34500
tgggctcagc aggccaggga gctcttagct gtgtgtgttg ggaagctcag aagggaggaa    34560
gaggttgtct gtgcaggtaa gtcctgagaa cacaccagac ttttgagagg tggagcttca    34620
tagccaggtc attaggggag aagggagcta tagatttttt tttttttttt tttttttttt    34680
ttttttttag acgggggtc ttactatgtt gcccaggctg tcttgaact cctgggctca    34740 agtgatcctc ccacctcagc ctcccaaagt gctgggatta gaggcatcag ccaccccgcc    34800
cagcgagcta tggatctaac atgtacatct tacacagtgc taatagaatg ttgggtttct    34860
tccccaatat tttattttga aaaaaattc aaatatatag aaaagttgaa aaatgtagtt    34920
caaagaacac ctacatacct ttcacataga ttcatgattt gttaatgtta tgccactttg    34980
tatatatctc tctccctcct atctgtatac ttttatttat ttattttgc tgaactattt    35040 cagagtaact taaaggcatc ttgatttttac ccttgaacag ttcaatatgt ttctgctaag    35100
aattctccta tataagtcag atatcattac atctaagaaa attcacggca attttacaat    35160
ataatattat agtccaaatc catatttcct cagttgttcc aaaaaatgtt catggctgtt    35220 tccttttta atctaaattt gaatccaagt ttgaggcatt gtatttggtt gctgtgtctc    35280
tagggttttt aaaatctgtg ccttttcttc tccccatgac tttttagaag agtcaagacc    35340
ggttattctt atagaataac ccacattcta gatttgcctg attagttttt ttatacttaa    35400 cgtattttg gcaagaacat tacattggta acgctgttgg tgatgggtca gttttgaaga    35460
gtggagatga ttaaactgct tttgttcatt gaagtatctg tcaagaccag agatccttaa    35520
ctggtgccat aaataggttt cagagaatcc tttatatata caccctgtcc cccacctaaa    35580
ttatatacac atcttcttta tatattcatt tttctagggg aggcttcttg gcttttatca    35640
aattctcaga gggccccaag acccaaagag gttatgaaac actagtctgt ccactgaggc    35700
aggcaacaca gagctggttt ctggggcctt gttcagtctg aaccagcttc ccttggggag    35760
atagcacaag gctgtaactt tgccccatct tggctttgga tcaaagagga ctgtccattt    35820
tgttgtcata cctaggaacc agggacagct tatgtggcct ggttccaggg atccaggaga    35880
atttcagttc ttgtcttgcc tttcaggtgt tcagaatgcc aggattccct caccaactgg    35940
tactatgaga aggatgggaa gctctactgc cccaaggact actgggggaa gtttggggag    36000
ttctgtcatg ggtgctccct gctgatgaca gggccttta tggtgagtga atcccttcat    36060
atctgcccct cttggtcttc agagtccatt gacagtgctt ccagttccct gtggcctgtt    36120
aatcttttag tctttccatc agccaggca tctcccttta tttattcatt cattcaacta    36180
gcaggtatca attgagcacc tactaagtga aggtaagat ccttccctca aagacttaat    36240
agttgaacgt tgggagtggg aggagaggca ggcagagagg agacacaata tagttggata    36300
aggacctcca aggagagtgt tacaggctga gaggaggata tacttaggtt gtcttaggg    36360
```

-continued

```
aatcagaaaa ggagactctg gaataggctg gcagagagag gggctacctc ctatacctgc    36420
tctggacaaa cgactttaag catagtgaca gatttgccaa ccctgtattg gaagaactga    36480
tcttttttag tggggatgat tacttctggg gatttcttct cataactgag accaaaacag    36540
ttttgtgcag tctcagaaat gacaggaggt accaatctga cacttccttt ggaagctcta    36600
gggcagagag tgaaagagtg gattttgacg ggggccttgc ttggaggtca ttcacccacc    36660
cctgtcctca ctccagcaac agtgataact cacttccttc ctcccttgt acacccttct     36720 ccccacctgc tcacaggtgg ctggggagtt caagtaccac ccagagtgct ttgcctgtat    36780
gagctgcaag gtgatcattg aggatgggga tgcatatgca ctggtgcagc atgccaccct    36840
ctactggtaa gatagtggtc ctttgtctat cctctcccat ataagagtgg ctggcgggga    36900
gggacagtgg cagggtgagt tgggcagaag gagtgttagg gtagtcagag cattggattc    36960
ttaccacagc agtgctctta accagctctt taacttgtaa gcagaatgat ttacacatgt    37020
ctctacccTt tttccttacc aaccttgaaa atgtcttcac tctgccctgc aatcctccca    37080
gtgggaggca ctcttcaagg acgatcccag aacattaaag tcaaagaccc cttagagctc    37140
accctgtcca accaccttgg ttgataaaag aagtcagcct ggggcccatg gaatagaata    37200
gtacaagggc aaggttctca ttgtgagtca aggtagagt gaagagaacc cagaccatct    37260
caccccaacc caggccagtg tttttccaaa tataccactt gctgcagatc tagctcagca    37320
cccccagtcc cagcccaccc tgagaaccca ggctcctcat tctgagcagc cagctagaat    37380
catgacaaag agggtggtag tgagactatg ggtactgttg cttaaagcca catggtgcag    37440
tggttgctgg ggggcttctg tgtgggactc tagcatctta ttccccCctg tgccctctcc    37500
ccagtgggaa gtgccacaat gaggtggtgc tggcacccat gtttgagaga ctctccacag    37560
agtctgttca ggagcagctg ccctactctg tcacgctcat ctccatgccg gccaccactg    37620
aaggcaggcg gggcttctcc gtgtccgtgg agagtgcctg ctccaactac gccaccactg    37680
tgcaagtgaa agagtaagta ttttgagaac ccttcagcag gggttcttga gcagagtctg    37740
taaatgggcc tcagagggct tagacctcca aagtctcatg cagaactccc tttattctca    37800
tctcatatct ttctcctgga ccccactatg ctgtaaccgt acctgggcct tggcacttac    37860
tgttctctct gcccaggcta cttcctaccc gatacttaag gcaagaatca ctcacctttc    37920
aggtgtcagg tttcaggtca tgtttgctct ttgaaatcat ctggcttgat tatgtgtatt    37980
agttgtttat cttctatccc ctccactaga atgtaaattc cagaagaaac ttgctgtctt    38040
attcagtgct gcatgcccag ggcttggaag agtacctggc atatagtagg agttgattga    38100
ttattatttt gtcagtcgag agaatgaatg gagaaaatgt ggtccatggc ccaaaagaag    38160
ttaagaccct atcctagatt caggccagag accagatgga gaaagagtct gtgtctatct    38220
aataccagta atgtcgtacc tctggccgct taccatgtaa atattgattg tgtatctacc    38280
atgtgttgga cactaggcta gtgcttgcac agcaggtgaa agatactaga gtttgggaag    38340
tcaggaggag ctaaggtctg ttctacaacc ttattagatg aagaggagag ggaattgtgt    38400
tcagggcaga gggagaagca tttctccaaa agtaggagtc ttaatcatgt ctgatgtagg    38460
ttgagtgtgg ccagaaaagg ggctgttaag tatagagggc ctggattatg aaaatccagc    38520
agatccattg agagtttaag cagcaaggtg ttgtgaccaa gttaacattt tagaaggatc    38580
actggtatgg aggttggatt ggagagggga aagcctaaag gtatagagac tagttaggaa    38640
gctattgtag gctgggcatg gtggttcatg cctgtaatct cagcactttg ggaggctgag    38700
gtgggaggat tgcttgaggc caggagttga agaccaacct ggccaacata gcaagacccc    38760
```

-continued

```
gtctctgttt tcttaatta aagaaaagt ccagacgtag acatagtggc tcacgcctgt   38820
aatgccagca ctttgggagg ccaaggtggg cagattgctt gaggtcaaga gtttgggatt   38880
aggccaggcg cagtggctca cgcctgtaat cccagcactt tgggaggccg aggtgggcgg   38940
atcacaaggt caggagatca agaccatcct ggctaacaca atgaaacccc gtctctacta   39000
aaagtacaaa aattagccgg gcatggtggc ggacgcctgt agtcccagct actcgggagg   39060
ctgaggcagg agaatggcgt gaacctagga ggcggagctt gctgtgagca gagatcacgc   39120
cactgcactc cagcctgagc gacagagcga gactccatct caaaaaaaaa aaagagtttg   39180
ggattagcct ggccaacatg gcaaaacccc atctctacaa aaagtacaaa aaattagct   39240 gggtatggtg gtgcgcgcct gtaatcccag ttactcagga ggctgaggca tgagaattgc   39300
ttgagcctgg gaggtggagg ttgcagtgag cccagatcat gccactgcac tccagcctgg   39360
atgacagagt aagatgccat ctcaaataaa aattaaaaac aaagtttaaa aaaaaatag   39420 aagctattac cgtgatccag gtaagagatg tgaataacta caatgatgga aagaaggcag   39480
agttcttaga gatgggagta ggagagatga gggaactcca gattgggaag atgatgttca   39540
agtttctggc ttaggccaca gggtgagtgg caattcccctt cactgagatg gggcatcctg   39600
gaaaaggtgt tgccttttctg tgtgggtatc ctgggcccct taggggccac tggtggcctg   39660
ggacctggta aaccttccct gcacaagcag aattggtcaa gcaggttttt aggacatctt   39720
taccctgcct caactcttgt ctggcccagg gtcaaccgga tgcacatcag tcccaacaat   39780
cgaaacgcca tccaccctgg ggaccgcatc ctggagatca atgggacccc cgtccgcaca   39840
cttcgagtgg aggaggtaga gtgtgtgtct aatctgtctt tgagggtgg acatggaac   39900 agatcctctg ggaaatcagg ctgtagcctt tacctttttcc taccccagc ccatctcttt   39960 gtcttagcat tgagcctgtg accactggtg acctatttca gcgtaacagg ttcccagggt   40020
agcagggatg gttgatggac gggagagctg acaggatgcc aggcagaggg cactgtgagg   40080
ccactggcag ctaaaggcca ccattagaca agttgagcac tggccacact gtgcctgagt   40140
catctgggtt ggccatgggt ggcctgggat ggggcagcct gtgggagctt tatactgctc   40200
ttggccacag gtggaggatg caattagcca gacgagccag acacttcagc tgttgattga   40260
acatgacccc gtctcccaac gcctggacca gctgcggctg gaggcccggc tcgctcctca   40320
catgcagaat gccggacacc cccacgcccct cagcaccctg gacaccaagg agaatctgga   40380
ggggacactg aggagacgtt ccctaaggtg ccacctccca ccctggctct gttctgtcct   40440
atgtctgtct ctcggatgaa gctgagctgg cttttcagaag cctgcagagt taggaaagga   40500
accagctggc cagggacaga ctatgaggat tgtgctgacc cagctgcccc tgtggggatc   40560
acagtttaca gccagagcct gtgcggaccc agctgtctgc caggtttcct tagaaacctg   40620
agagtcagtc tctgtccact gaactcctaa gctggacagg aggcagtgat gctaaaccct   40680
gaagggcaac atggcctatg gagaaagcat ggagctcaga gcctggagta cgggcacaga   40740
taggattgaa taaattgtgt agaaagactt tgaaaacaat aaagcaaaag atgaatgaac   40800
gtttttttta gacttgaggg accaacaacc cccaaacccc agattctgcc aggtccatgg   40860
ggaaggagaa gttgccttga gtggaagccc aagtaggga gacttacaga aaagaagtca   40920
agagcactgg ctcccaggca gaaatactga taccctactg gggcttcagg ctgagctcct   40980
cccttcacaa atcacttcat ctctctgagc ctgtttctgc atctgtgaca taagatggta   41040
agataaaggt ggctgtctca ccaattatgt aaggattaaa tgtggaaaag gacataaagt   41100
```

```
tgtatagtgc tgccataggg acagtgttca gtaaacgtga cacattctta gtatcactaa   41160
gaatcaggtt cttggccagg caccgtggct catgcctgta atcccaacac tctgggaggc   41220
ctaggtcgga ggatggcttg aacacaggag tttgagacca gcctgagcaa catagtgaga   41280
cactgtctct acaaaaaaaa aataataata ataattgttt ttaattagat gggcagggca   41340
ctgtggctca cacctgtaat cccagcactt tgggaggcca aggccggagg attgcttgag   41400
gccaggagtt caggagcagc ctgggccaca ttcctgtctc tacaaagaat aaaaaagtta   41460
actgggcatg gtggcacatg cctgtaatcc cagctactca agaggctgag gaggaggatt   41520
gcctgagccc aggagttcaa gactgcagtg agccttgatc acaccactgt actacagctt   41580
gggcaacaga gtgagacctt gtctccaaaa aaaaagttt gtttttttt atccactctc   41640 ctcaccaaac aaactgagta agttagagcc ctctcagctg gcatgtgttg gaaacagtgc   41700
cctctcatta aagtgctgcc ctcactccca ttgcctcttg gccttggtca gtatgatgaa   41760
attagtggga ggcagggcaa cagagggcag ggaagagcta gaaatccatg gcctggaaaa   41820
gggaagattt gggagtggcc aggtatctgt agagccacca tgcagaggag ggggcagct   41880 agccttgtgt gctctggtgg gcatggtcag caggaggcag agcaaaagga caagggtaag   41940
taaacctgta ggtcgggaca agccaagagc catccagcgt cagtcctctc tgggtagccc   42000
aagtaaagca ggagcatacc ccagagagaa agttcgcagg gctgttcacc tgcagtgctg   42060
tggacttcaa ccttcttgtt ccttcttcag taagtgaaaa taacagtcat tgaccatgac   42120
tattatcgac cgcttttgaa aatgtaaaca tagtgacttt attgctgtaa aaatcatacg   42180
tgtttatcat cttaaaattc aggaaacatg gacaggtaca aagatgtgca aaatatcatc   42240
caaaatccca tttgctggcc aggcacggtg gctcacgcct gtaatcccag cacattggga   42300
ggccgaggcg ggcaaatcac ttgaggtcag gagtttgaga ccagcctggc caacatggtg   42360
aaaccctatc tctactaaaa atacaataat taggctgggc gcagtggctc acgcctataa   42420
tcccagcact ttgggaggcc gaggtgggcg aatcacaagg tcaggagttt gagactagcc   42480
tggccaatat ggtgaaaccc catctctact aaaaatacaa aaattagggc cgggtgtggt   42540
ggctcacgcc tgtaatccca gcacttaggg aggccgagac agatggatcg cgagatcagg   42600
agttcgagac caacctagcc aacatggtga acccccatct ctactaaaaa atacaaaaa   42660 ttattcggtt gtggtggcac acgcctgtaa tcccagctac ttgggaggct gaggcaggag   42720
aatctcttga acctgggagg cagaggttgc agtgagtgga gatcccgccg ttgcactcca   42780
gcctgggcga cagagtgaga ctccatcaaa aaaaaaaaa aaaaaaaaa aaattagccg   42840 ggcgtggtgg cgtgcaccta tactcccagc tacttgggag gctgaggcag gagaatcgct   42900
tgaacctgga aggcggaggt cgcagtgagc cgagatcgtg ccattgcact tcagcctggg   42960
cgacagagcg agactctgtc tcaaaaataa taataataac aataactagc cgggcctggt   43020
ggcacatgcc tgtagtccca gttactcagg aggcggaggc atgagactca ggtgaactag   43080
ggagacagag gttgcagtga gccaagatca caccactgca ctccagcctg ttgacagag   43140 cgagactctg tctcaaaaaa aaaaaaatcc catttgctca ttttttggat actagtataa   43200
ctatcactct aaaccagtta gtacttaaat caagcagata tggagatgg tgaattacca   43260 tctacagtgt tgtcatatat gtcacatact gagcattatc agctagtaga atctagttaa   43320
ttgttctatg tgtgatgtat gcagagttcc cattttgaat gtgttttac tatgcttaaa   43380 taaatgactg atgtcagcaa ccccaaaatg atacatctga tgtaagagcc cctgttcccc   43440
aataataaca tctaaactat agacattgga atgaacaggt gccctaagt ttcctccctc   43500
```

```
cagggtttct tggccggtct ctgaggacta cacatccctc ctcccgtctt tcctcatctt    43560
caggcgcagt aacagtatct ccaagtcccc tggccccagc tccccaaagg agccctgct     43620 gttcagccgt gacatcagcc gctcagaatc ccttcgttgt tccagcagct attcacagca    43680
gatcttccgg ccctgtgacc taatccatgg ggaggtcctg gggaagggct tctttgggca    43740
ggctatcaag gtgagcgcag gcaacaattg ctttgctctt ctgccccccag tccctctgtc   43800 actgtctttc ggggatttct catcacttgg ccccacccca caccatgcag gatgccaggc    43860
ctccttcctg gctttgggtg ttggtgtgag aggtatcctt caccccccacc caggccacct   43920 aaggtcaatg ttgctgttac agtgagcttg tggacctgga gatccaggtt gggttgagct    43980
gtgcctgtgg ccctcctgcc tccagtcagt gggtgtttgt taggtgcctg cagacctcag    44040
taccgggcat gctacaagga gcacacaggg gaatggctcc tgcctccctg gtgaacagtc    44100
tcagggacta acctctctct ttctctcctc ctcctcctct tctgctgaga actgggaggg    44160
ggggtcaggt aagacgtgtg tctcagcttg ggggcagcag ggctggagag ctcacccccg    44220
atccacccag ctccctggtg catgtctttg gcactgacct tcctgccccc agacttctgt    44280
tcactcagga gactcacttc tatgccaaat gaccagagcc cctgcttggc ttggcagcat    44340
cccctcctgc cttcttcccc acttcccttt tctgggttct tgcctgtcct ctgtgcatgc    44400
ccagctctcc aggaaagagg gtttgcttcc gtgtgagtcc catgttgctc cacgctgcat    44460
cttccacaca tgaactctgt cattctgacc cggctcagtg tgccctccaa gggatgggat    44520
ggccagctgc atagattttc tcaaacagtt ctccagaact tcctctggtc tcagcaccat    44580
taacagtcac cctccctgta ggtgacacac aaagccacgg gcaaagtgat ggtcatgaaa    44640
gagttaattc gatgtgatga ggagacccag aaaacttttc tgactgaggt aagaagatgg    44700
agggggcccg ggaggttggt gtcaccattg aagagagaa gaccttacaa ataatggctt     44760
caagagaaaa tacagtttgg aattactgtc ttaaagacta agcagaaaag agccctagag    44820
gaatatccca ctccctctaa attacagcgt aattatttgt tcaatgaaca cttactaaaa    44880
gcaacacaaa caggtacaa gggatgcagt aacaaaagat acaggttca gaagagctct      44940 caggttatga ggatgatgga catgaaaaca ctccaattta gtacaactca atgttataat    45000
cctcacctga acgccctgct aagggagcct ggaggggagc tccctgagca ctcacactcc    45060
ttgggcattt acagttttca ctaccctcc caagttactt catggagtaa cttaagttgg      45120
ggacacctgt ggtctgggta ttgccctcca agccacttgg ccactccac cccagttctc     45180 ccaatgcagt tccaagggta aggcctatga agccatctcc atctatatgg tggtggtctt    45240
ccctcatcct gatcttagtg ccctgtcata tcacaagata ggaggtagga gatacaggtg    45300
gtaacacttg tcaagctgat tccttggagg gaagaggtaa ggaagacagt gagaagttaa    45360
ccaccagctt tccttggctt cccccacccc caggtgaaag tgatgcgcag cctggaccac    45420
cccaatgtgc tcaagttcat tggtgtgctg tacaaggata agaagctgaa cctgctgaca    45480
gagtacattg agggggcac actgaaggac tttctgcgca gtatggtgag cacaccaccc     45540
catagtctcc aggagccttg gtgggttgtc agacacctat gctatcacta ccctaggagc    45600
ttaaagggca gaggggccct gctttgcctc caaaggacca tgctgggtgg gactgagcat    45660
acatagggag gcttcactgg gagaccacat tgacccatgg ggcctggacc acgagtggga    45720
cagggctcaa cagcctctga aaatcattcc ccattctgca ggatccgttc ccctggcagc    45780
agaaggtcag gtttgccaaa ggaatcgcct ccggaatggt gagtcccacc aacaaacctg    45840
```

-continued

```
ccagcagggc gagagtaggg agaggtgtga gaattgtggg cttcactgga aggtagagac    45900
cccttcctat gcaacttgtg tgggctgggt cagcagctat tcattgagtt tgtctgtgtc    45960
actgaaactg accccagcca actgttctca gttcacagcc ctgttttcaa agaattacac    46020
atctctaaag gcaaacaggg cacggacaag gcaaactgga gaggcaaact gtagcctgag    46080
atggcctggg cttgccatca caggtattca ggtgctgagg gcccttagac caactagagc    46140
acctcactgc ctaggaaatc aatgaagggg aaatgagttc tagcggagcc ctgaaggatc    46200
agaattggat aaagttctta ttggcagaga ggcaccagga ttgaagtgac aggagcaaag    46260
acctgggagg aaagaggaga aaatcatcta tttcacctgg aaacaaatga ttccaagcat    46320
agaaataata acagctgaca agtactgagt gccctctata tgctaggcac tgggctgagg    46380
gattaacatg catgtgcatg tttattcctc atgacaacct tggtttccag ataagctgga    46440
ctggaaaggg acagagctgg gatcctgggc taatcagtct ggtcgccaag cctgagactt    46500
tagccactgc ccttcacatg ggggtccatg aaaatagtag tagtctggaa cagtttgggg    46560
gtacatcaag gtcgctgtgt tttaagctat ggagtctgga ctataggaga caaatgtaaa    46620
agagtttttt ggttgactgg cttttttggtt tttttgtttg tttgtttgtt tgtttgtttg    46680
tttgtttgtt ttttcctgtt tctgggcctt gaatcaggaa ggaggttttt ttgttgttgt    46740
tgttttgaga aaggatattg ctctgttgcc cagactggag tgcagtggca cgatcatggc    46800
tcactacagc ttcgacctcc tgggctcaag caatcctcct gccttagcct cccaagtagc    46860
tggactacag gtgtgtacca ccacacctaa tttttttgaat tttttttttct tttttttttt    46920 tttttttttt ggtagagaca ggttctcact ttgttgccca ggcctgaatc tcaaactcct    46980
gggctcaagc attcctcctg cctcgccctc ccaaagtgtt gggattacag ttgtgagcca    47040
ccatgcccgg caggaaaaga ttttttaagca agaaagctta agagctgtgg tttttccaaa    47100
atgagtctgg gctggcacag tggctcatgc ctgtaatccc agcactttttt tgggaggccg    47160 aggtgagtgg atcacttgag gtcaggagtt tgagaccagc ctggccaact ggtgaaaccc    47220
ctgtttctac taaagaaaaa aatgcaaaaa ttagctgggc gtggtggtgc acgcctgtag    47280
tcccagctac tcaggaggcc gaggcaggag aatagcttga acctgggagg cagaagttgc    47340
agtgagccaa gatcacacca ctgcattcca gcctgggtga cagagtgaga cttcatctca    47400
aaaaaaaaaa aaaagagaga ctgatatggt tagtacattg gggtggaatg cggagggtcc    47460
agggaatgga gccctgcata gggggctaat gaaacatttc agatttctga attaaggtag    47520
tggctgtggg gacaggagcc tgggaggcag ggtggagtca gaatgagag actggttggc    47580 aatgagggaa caggaggagg aggaggagga gttacgagtg gcttgaggtg tcacttacca    47640
gacatttggg ggatggggga tagccgtgat tgttgagcaa ctggtttggg aagagctagc    47700
attgatccct gctgttctgt gctagcagaa cctatcagca tcttctgggc aggaaactgg    47760
ctccatgaga ctggcttagg gagaggctgc tagtcaccta atctgcagag aaggggcagc    47820
tggagctgtg ggacagaaga ggcatccatg tagctggtgg gggtgtctca gcttgtgaag    47880
aggagatggc tttgagcagg gctgacactg aaaaggctgg aagaaaaaaa cagacacaca    47940
agagtctcag gatcaggtag catcaggaaag ttgtggacag tctttgagga gcactccctc    48000
aggcaggcag gcaggcaggt catgagctat agcgattcag gaagagctcc ctgggtgtgt    48060
gagcagctcc aggagcctaa gggatgaaag tagtattgca gggggctgga gagcaaggag    48120
tggctccttc tacatttgca agggaaggag aaaggaagtt gctcctgaga gtggtaagag    48180
tcagtggtgg aggcctggag aggagacata acaaacaaat ttgttgacaa acattttggt    48240
```

-continued

```
aggaaggggg agagcttaaa gtttagacag tggggaaggt ggagtcttag aggaggtgaa    48300
tgtctgaaag acagagctag ctggagcaag aagtcacttc tctgttgcag gcaggaagga    48360
tccaaagtgg ctcaagccag agattgggag agtgggagg agggagcagc ctggatctaa     48420
gtaaaatggg tagaggtgga gggggtgctg caacggccag ggttttctga agttggggac    48480
attaggagag agctgtgagg gctttggcca gccactgtgc tagtgattgg tgaaccaaag    48540
gatgggcagg agatgcagc agggaagcag aggaagtcca ggcttcctgt tggtattggg     48600
acaagggaga ggccatagga ggccctggcc ctgttgtcca ggttgggttc tgaagctggg    48660
tgggcatggc ctggtaggag agcatctatg gcgcccaatt ccagattcag ggtctagttg    48720
atttgctggc cctgtagcct cagctcatgc ttctgttcca ggcctatttg cactctatgt    48780
gcatcatcca ccgggatctg aactcgcaca actgcctcat caagttggta tgtcccactg    48840
ctctgggcct ggcctccagg gtcctatcct tcctggcttc cttgtcacaa aggaggctga    48900
cttgtcccct ctggctagag ggcagaggtg ttgcctagga gctcctatct ttcccttcct    48960
gcttcttcca atgcccttct ctgtcctctg ggagctccga gacacacaca gacataattt    49020
caccttctct cattagcaac ctttgaaata atttgattag aagggacttc agaagtttgt    49080
tgactatatg tagaaaaccc tgtcatttta cctgcttttg ccccatagta gtcttgtaaa    49140
acagttcatt gctgacccca ttttacagtg gtggcacctg aagcctcagc ctgaggccac    49200
cgagctagta aatttacagg gaccagtttg agaccagcat tcctcccact gcccctcagc    49260
tgtggtggtt acaatgttgt ttgtcttact gacttgctat ctggcttcct gggtgtctac    49320
cggctggccc tggctctgcc ctctagaccc acaccacgca atcttcattc ctttcccaca    49380
tgactgccct gtagctattc aaagagcttg tctcccccaa gtctccccat ctactgcctc    49440 cacctttgcct ttttctgtct tatcctggtt ctagccactg cctgaaatca ttttaggaat    49500
aagacaggac agggaaaaac aaaagcaacc ccctgtccca cctctgagtt ccactctcca    49560
agtccctgag cctcacctcc agggctccag tggctctgcc atgaacccac tgtgggctgg    49620
gagtctgctg tgcacagata ccagaccctc agaaacacaa atgccaagtg tgtctgtttt    49680
tttgttttgt tttgttttgt tttttagatg gagtctcatt ctgttcccca ggctggagtg    49740
cagtggtgca atcttggctt actgcagcct ctacctcccg ggttctagtg attgttctgc    49800
ttcagcctcc cagtagctag gactacaggc gtgtgccacc acgccagct aatttttttt     49860 tttttttttt tgtattttta gtagagacag ggttttgcca tgttggccag gctggtcttg    49920
aactcctgac ctcaggtgat tcacccgcct tggcctccca aagttctggg attacaggtg    49980
gaagccaccg tgcctggcct gagtgtgtct atttgataga gctttctgct ctgattctcc    50040
cttgctatac acctttttctc cccttctcag tggcttctct tgcctatgct tcctccccag   50100
ggccaggttt gagaacatcc ccatgaagtc ctgacctgtc ttttatccta ccaggacaag    50160
actgtggtgg tggcagactt tgggctgtca cggctcatag tggaagagag gaaaagggcc    50220
cccatggaga aggccaccac caagaaacgc accttgcgca agaacgaccg caagaagcgc    50280
tacacggtgg tgggaaaccc ctactggatg gcccctgaga tgctgaacgg tgagtcctga    50340
agccctggag gggacacccg cagagggagg acagatgctg cccttgcatc agagccctgg    50400
gaattccagg ggaggcctgt gaagcgtagg accggatacc cagagctgag gatattttt     50460 ccttgccagg tggggcctca cgatttagct cctgagctca gggggctggg aactgatcag    50520
tgtcccatca tggggataa ggtgagttct gactgtggca tttgtgcctc aggatcgct      50580
```

```
aagagctcag gctattgtcc cagctttagc cttctctctc catggtgaga actgaagtgt      50640
ggtgccctct ggtggataat gctcaaacca accagagatg ctggttggga ttcttgaaat      50700
cagggttgtg aggcctcaga aatggtctga atacaatcca ttttggagtc tgaggcccag      50760
agaagttcag tgaattgcct aggagcatac agctgcctaa tggcagaggc tagatgaacc      50820
ctagtctggt tcttttccac tttaacgtgc agtttcatcc taggcagtgt tatgttataa      50880
gggctctcca aggcagttca cctacggctg aggaaggact attttcaggt ggtgtctgcg      50940
caggacagcc tgtggggtgt ccctacagaa cctgttctag ccctagttct tagctgtggc      51000
ttagattgac cctagaccca gtgcagagca ggtaagggat gtaaacttaa cagtgtgctc      51060
tcctgtgttc cccaaggaaa gagctatgat gagacggtgg atatcttctc ctttgggatc      51120
gttctctgtg aggtgagctc tggcaccaag gccatgcccg aggcagcagg cctagcagct      51180
ctgccttccc tcggaactgg ggcatctcct cctagggatg actagcttga ctaaaatcaa      51240
catgggtgta gggttttatg gtttataacg catctgcaca tctttgccac gttcgtgttt      51300
cattggtctt aagagaagga ctggcagggt ttttttgttt tagatggagc ctcacttcgt      51360
tgcccaggct ggagtgcagt ggcacaatct gggctcactg caacctctgc cttctgggtt      51420
caagtgattc tcctgcctca gcctcccaag tagctgggac taccggcaca ccaccaccatg      51480
cccggctaat ttttgtattt ttagtagaga cagggtttca ccatgttggc caggctggtc      51540
ttgaactccg gacctcaggt gatccgcctg cctcagcctc taaaagtgct ggaattaata      51600
ggcgtgagct acctcgcccg gccaggtttt ttttttttt ttttagttg aggaaactga      51660
ggcttggaag agggcagtgg cttgcacatg gtcgataagg ggcagatgag actcagaatt      51720
ccagaaggaa gggcaagaga ctgttcatgt ggctgtctag ctagctcttg ggccaaatgt      51780
agcccttctc agttcccttc aagtagaagt agccactcta ggaagtgtca gccctgtgcc      51840
aggtaccacg tggacagagt gaggaatctt ggaaagattc ctacctttag gagtttagtc      51900
aggtgacagc atatctcagc gactcaaaca cacacacatt caaagccttc tgtaattcct      51960
acaaagttgt gaggggtaga ggagaggaga gacaagggat ggttaggata atgaaggaat      52020
gttttgtttt tgttttgtt tttgagatgg agtttcactc tgtcacccag gctggagtgc      52080
agaggtgcaa tctggctca ctgcagcctc gcctcccag gttcaagcaa tcctcctgcc      52140
tcagcctccc aagtagctgg gactacaggt gtgcgccacc acgcctggct aattttgta      52200
ttttcagtag agacagggtt tcgccatatt ggccaggctg gtctcaaatg cctgacctca      52260
ggtgatacac ccgcttcagc ctcccaaagt gctgagatta caggcatgag ctaccgtgcc      52320
tggccatgaa ggaagatttg ttttaaaaaa ttgttttctt taatattaat tgaacacctc      52380
tgttcagagc actgggctgg tgccagaggg tttcagacat gaatcagatc cagcacctca      52440
tagagcctta atctggcaca cacacacagc cacaaggaga cacagacaag gcagggtagg      52500
atgagtggaa gctaggagca gatgctgatt tggaacactt ggcttctgca gtgaagcccc      52560
ttcttagtcc tcttcagtaa cccagctctc agtggataca ggtctggatt agtaagattt      52620
ggagagatga ttggggattg gggagagctc tctaacctat tttaccacct cctcttctgc      52680
cattcttcct gtccacatcc ccagcatccc tttcccttgc caagtatctg tggcctctgt      52740
agtcctttgt aaacagctgt cttcttaccc tacagatcat tgggcaggtg tatgcagatc      52800
ctgactgcct tccccgaaca ctggactttg gcctcaacgt gaagcttttc tgggagaagt      52860
ttgttcccac agattgtccc ccggccttct tcccgctggc cgccatctgc tgcagactgg      52920
agcctgagag caggttggta tcctgccttt ttctcccagc tcacagggtc ctgggacgtt      52980
```

-continued

```
tgcctctgtc taaggccacc cctgagccct ctgcaagcac aggggtgaga gaagccttga      53040
ggtcaagaat gtggctgtca acccctgagc catctgacaa cacatatgta caggttggag      53100
aagagagagg taaagacata gcagcaagta atctggatag gacacagaaa cacagccatt      53160
aaaagaaagt ttaaaagaag gaaattcacc caaaccattt gaatacagta agtgtattca      53220
tctttcgata ttcccctgtc catatctaca catatacttt tttttatagt aaatagttct      53280
gtattttgcc ctgcatttcc cttgtgttta ctatccagtc ttcctgttta tcattttgt       53340 cgacaacatg aaattctatt gagagactgt ctgaacatat tgtaatgtag atgttcaggt      53400
ttttccagtt tctctttaca ataggtattt aactacagtg agcagttttta tgcatttagc     53460 taatttctcc tttgaggaag tattttcaaa attaccttta ttcttctcag gtaataattt      53520
cattattacc aaagttaccc taggtctttt caagtgtgtg gttaaaaaac gagaatctgg      53580
ctgggcgcga tggctcacac ctgtaatccc agcactttgg gaggctgagg ctggtggatc      53640
acctgaggtc tggagttcga accagcctg gccaacatgg tgaaacccca tctctactaa       53700
aaatacaaaa cttagccagg catggtggca ggtgcctgta accccagcta cttgggaggc      53760
tgaggcagga gaattgcttg aacccagggg cggaggttgc agtgagccga tatcacgcca      53820
ttgcactcca gcctcggcaa caagagtgaa actctgtctc aaaaatgggg ttcttttcct      53880
gccatcaaaa atcatgtttc ttttaaaaac aagttcaaac attaccaaag tttatagcac      53940
aggaaatacg tcttctgtaa tctcccttaa ccaatatatc cctcaacatt ctcctcaccc      54000
ccaactccac cctcccagga taaccagttg ggacataatc tttatttaaa aatggtttcc      54060
ggatagagaa agcgcttcgg cggcggcagc cccggcggcg ccgcagggg acaaagggcg       54120 ggcggatcgg cggggagggg gcggggcgcg accaggccag gcccgggggc tccgcatgct      54180
gcagctgcct ctcgggcgcc cccgccgccg ccctcgccgc ggagccggcg agctaacctg      54240
agccagccgg cgggcgtcac ggaggcggcg gcacaaggag gggccccacg cgcgcacgtg      54300
gcccccgagg ccgccgtggc ggacagcggc accgcggggg gcgcggcgtt ggcggccccg      54360
gccccggccc ccaggccagg cagtggcggc caaggaccac gcatctactt tcagagcccc      54420
ccccggggcc gcaggagagg gcccgggctg ggcggatgat gagggcccag tgaggcgcca      54480
agggaaggtc accatcaagt atgaccccaa ggagctacgg aagcacctca acctagagga      54540
gtggatcctg gagcagctca cgcgcctcta cgactgccag gaagaggaga tctcagaact      54600
agagattgac gtggatgagc tcctggacat ggagagtgac gatgcctggg cttccagggt      54660
caaggagctg ctggttgact gttacaaacc cacagaggcc ttcatctctg gcctgctgga      54720
caagatccgg gccatgcaga agctgagcac accccagaag aagtgagggt ccccgaccca      54780
ggcgaacggt ggctcccata ggacaatcgc tacccccga cctcgtagca acagcaatac      54840
cgggggaccc tgcggccagg cctggttcca tgagcagggc tcctcgtgcc cctggcccag      54900
gggtctcttc ccctgccccc tcagtttttcc actttttggat ttttttattg ttattaaact   54960
gatgggactt tgtgttttta tattgactct gcggcacggg cccttttaata aagcgaggta     55020 gggtacgcct ttggtgcagc tcaaaaaaaa aaaaaaaat gatttccagc ggtccacatt      55080
agagttgaaa ttttctggtg ggagaatcta taccttgttc ctttatagc caaggaccgc      55140 agtccttcag taacaccagt gtaaaagctt gaggagaaat tgtgaagcta cacagtattt      55200
gttttctaat acctcttgtc attctaaata tctttaattt attaaaaaat atatatatac     55260
agtattgaat gcctactgtg tgctaggtac agttctaaac acttggggtta cagcagcgaa     55320
```

```
caaaataaag gtgcttaccc tcatagaaca tagattctag catggtatct actgtatcat    55380
acagtagata caataagtaa actatattga atattagaat gtggcagatg ctatggaaaa    55440
agagtcaaga caagtaaaga cgattgttca gggtaccagt tgcaatttta aatatggtcg    55500
tcagagcagg cctcactgag gtgacatgac atttaagcat aaacatggag gaggaggagt    55560
aagcctgagc tgtcttaggc ttccggggca gccaagccat ttccgtggca ctaggagcct    55620
ggtgtttccg attccacctt tgataactgc attttctcta agatatggga gggaagtttt    55680
tctcctattg tttttaagta ttaactccag ctagtccagc cttgttatag tgttacctaa    55740
tctttatagc aaatatatga ggtaccggta acattatgcc catttctcac agaggcacta    55800
ctaggtgaag gagtttgcct gacgttatac aaccaggaag tagctgagcc tagatccctt    55860
ccacccaccc catggccctg ctcatgttcc acctgcctct aatttacctc ttttccttct    55920
agaccagcat tctcgaaatt ggaggactcc tttgaggccc tctccctgta cctgggggag    55980
ctgggcatcc cgctgcctgc agagctggag gagttggacc acactgtgag catgcagtac    56040
ggcctgaccc gggactcacc tccctagccc tggcccagcc ccctgcaggg gggtgttcta    56100
cagccagcat tgcccctctg tgccccattc ctgctgtgag cagggccgtc cgggcttcct    56160
gtggattggc ggaatgttta gaagcagaac aagccattcc tattacctcc ccaggaggca    56220
agtgggcgca gcaccaggga aatgtatctc cacaggttct ggggcctagt tactgtctgt    56280
aaatccaata cttgcctgaa agctgtgaag aagaaaaaaa cccctggcct ttgggccagg    56340
aggaatctgt tactcgaatc cacccaggaa ctccctggca gtggattgtg ggaggctctt    56400
gcttacacta atcagcgtga cctggacctg ctgggcagga tcccagggtg aacctgcctg    56460
tgaactctga agtcactagt ccagctgggt gcaggaggac ttcaagtgtg tggacgaaag    56520
aaagactgat ggctcaaagg gtgtgaaaaa gtcagtgatg ctccccttt ctactccaga    56580
tcctgtcctt cctggagcaa ggttgaggga gtaggttttg aagagtccct taatatgtgg    56640
tggaacaggc caggagttag agaaagggct ggcttctgtt tacctgctca ctggctctag    56700
ccagcccagg gaccacatca atgtgagagg aagcctccac ctcatgtttt caaacttaat    56760
actggagact ggctgagaac ttacggacaa catcctttct gtctgaaaca aacagtcaca    56820
agcacaggaa gaggctgggg gactagaaag aggccctgcc ctctagaaag ctcagatctt    56880
ggcttctgtt actcatactc gggtgggctc cttagtcaga tgcctaaaac attttgccta    56940
aagctcgatg ggtctggag acagtgtgg cttgtcacag gctagagtc tgagggaggg    57000
gagtgggagt ctcagcaatc tcttggtctt ggcttcatgg caaccactgc tcacccttca    57060
acatgcctgt tttaggcagc agcttgggct gggaagaggt ggtggcagag tctcaaagct    57120
gagatgctga gagagatagc tccctgagct gggccatctg acttctacct cccatgtttg    57180
ctctcccaac tcattagctc ctgggcagca tcctcctgag ccacatgtgc aggtactgga    57240
aaacctccat cttggctccc agagctctag gaactcttca tcacaactag atttgcctct    57300
tctaagtgtc tatgagcttg caccatattt aataaattgg gaatgggttt gggtattaa    57360
tgcaatgtgt ggtggttgta ttggagcagg gggaattgat aaaggagagt ggttgctgtt    57420
aatattatct tatctattgg gtggtatgtg aaatattgta catagacctg atgagttgtg    57480
ggaccagatg tcatctctgg tcagagttta cttgctatat agactgtact tatgtgtgaa    57540
gtttgcaagc ttgctttagg gctgagccct ggactcccag cagcagcaca gttcagcatt    57600
gtgtggctgg ttgtttcctg gctgtcccca gcaagtgtag gagtggtggg cctgaactgg    57660
gccattgatc agactaaata aattaagcag ttaacataac tggcaatatg gagagtgaaa    57720
```

-continued

```
acatgattgg ctcagggaca taaatgtaga gggtctgcta gccaccttct ggcctagccc    57780
acacaaactc cccatagcag agagttttca tgcacccaag tctaaaaccc tcaagcagac    57840
acccatctgc tctagagaat atgtacatcc cacctgaggc agcccttcc ttgcagcagg     57900 tgtgactgac tatgaccttt tcctggcctg gctctcacat gccagctgag tcattcctta   57960
ggagccctac cctttcatcc tctctatatg aatacttcca tagcctgggt atcctggctt    58020
gctttcctca gtgctgggtg ccacctttgc aatgggaaga aatgaatgca agtcacccca    58080 cccttgtgt ttccttacaa gtgcttgaga ggagaagacc agtttcttct tgcttctgca     58140
tgtgggggat gtcgtagaag agtgaccatt gggaaggaca atgctatctg gttagtgggg    58200
ccttgggcac aatataaatc tgtaaaccca aaggtgtttt ctcccaggca ctctcaaagc    58260
ttgaagaatc caacttaagg acagaatatg gttcccgaaa aaactgatg atctggagta    58320 cgcattgctg gcagaaccac agagcaatgg ctgggcatgg gcagaggtca tctgggtgtt    58380
cctgaggctg ataacctgtg gctgaaatcc cttgctaaaa gtccaggaga cactcctgtt    58440
ggtatctttt cttctggagt catagtagtc accttgcagg gaacttcctc agcccagggc    58500
tgctgcaggc agcccagtga cccttcctcc tctgcagtta ttccccttt ggctgctgca     58560 gcaccacccc cgtcacccac cacccaaccc ctgccgcact ccagcctta acaagggctg     58620 tctagatatt cattttaact acctccacct tggaaacaat tgctgaaggg gagaggattt    58680
gcaatgacca accaccttgt tgggacgcct gcacacctgt ctttcctgct tcaacctgaa    58740
agattcctga tgatgataat ctggacacag aagccgggca cggtggctct agcctgtaat    58800
ctcagcactt tgggaggcct cagcaggtgg atcacctgag atcaagagtt tgagaacagc    58860
ctgaccaaca tggtgaaacc ccgtctctac taaaaataca aaaattagcc aggtgtggtg    58920
gcacatacct gtaatcccag ctactctgga ggctgaggca ggagaatcgc ttgaacccac    58980
aaggcagagg ttgcagtgag gcgagatcat gccattgcac tccagcctgt gcaacaagag    59040
ccaaactcca tctcaaaaaa aaaaa                                          59065
```

<210> SEQ ID NO 4
<211> LENGTH: 265
<212> TYPE: PRT
<213> ORGANISM: Homo sapiens

<400> SEQUENCE: 4

```
Leu Thr Glu Val Lys Val Met Arg Ser Leu Asp His Pro Asn Val Leu
 1               5                  10                  15

Lys Phe Ile Gly Val Leu Tyr Lys Asp Lys Lys Leu Asn Leu Leu Thr
            20                  25                  30

Glu Tyr Ile Glu Gly Gly Thr Leu Lys Asp Phe Leu Arg Ser Met Asp
        35                  40                  45

Pro Phe Pro Trp Gln Gln Lys Val Arg Phe Ala Lys Gly Ile Ala Ser
    50                  55                  60

Gly Met Ala Tyr Leu His Ser Met Cys Ile Ile His Arg Asp Leu Asn
65                  70                  75                  80

Ser His Asn Cys Leu Ile Lys Leu Asp Lys Thr Val Val Ala Asp
                85                  90                  95

Phe Gly Leu Ser Arg Leu Ile Val Glu Glu Arg Lys Arg Ala Pro Met
            100                 105                 110

Glu Lys Ala Thr Thr Lys Lys Arg Thr Leu Arg Lys Asn Asp Arg Lys
        115                 120                 125
```

-continued

```
Lys Arg Tyr Thr Val Val Gly Asn Pro Tyr Trp Met Ala Pro Glu Met
            130             135             140

Leu Asn Gly Lys Ser Tyr Asp Glu Thr Val Asp Ile Phe Ser Phe Gly
145             150             155             160

Ile Val Leu Cys Glu Ile Ile Gly Gln Val Tyr Ala Asp Pro Asp Cys
                165             170             175

Leu Pro Arg Thr Leu Asp Phe Gly Leu Asn Val Lys Leu Phe Trp Glu
            180             185             190

Lys Phe Val Pro Thr Asp Cys Pro Pro Ala Phe Phe Pro Leu Ala Ala
            195             200             205

Ile Cys Cys Arg Leu Glu Pro Glu Ser Arg Pro Ala Phe Ser Lys Leu
            210             215             220

Glu Asp Ser Phe Glu Ala Leu Ser Leu Tyr Leu Gly Glu Leu Gly Ile
225             230             235             240

Pro Leu Pro Ala Glu Leu Glu Glu Leu Asp His Thr Val Ser Met Gln
                245             250             255

Tyr Gly Leu Thr Arg Asp Ser Pro Pro
                260             265
```

ISOLATED HUMAN KINASE PROTEINS, NUCLEIC ACID MOLECULES ENCODING HUMAN KINASE PROTEINS, AND USES THEREOF

The present application is a divisional of U.S. Ser. No. 09/978,197, filed Oct. 17, 2001 and issued as U.S. Pat. No. 6,403,353, which is a divisional of U.S. Ser. No. 09/813,817, filed Mar. 22, 2001 and issued as U.S. Pat. No. 6,340,583.

FIELD OF THE INVENTION

The present invention is in the field of kinase proteins that are related to the serine/threonine kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books*, Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine*, McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) EMBO Journal 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenesis) is often accompanied by increased tyrosine phosphorylation activity (Carbonneau H and Tonks N K (1992) *Annu. Rev. Cell. Biol.* 8:463–93). Regulation of PTK activity may therefore be an important strategy in controlling some types of cancer.

LIM Domain Kinases

The novel human protein, and encoding gene, provided by the present invention is related to the family of serine/threonine kinases in general, particularly LIM domain kinases (LIMK), and shows the highest degree of similarity to LIMK2, and the LIMK2b isoform (Genbank gi8051618) in particular (see the amino acid sequence alignment of the protein of the present invention, against LNK2b provided in FIG. 2). LIMK proteins generally have serine/threonine kinase activity. The protein of the present invention may be a novel alternative splice form of the art-known protein provided in Genbank gi8051618; however, the structure of the gene provided by the present invention is different from the art-known gene of gi8051618 and the first exon of the gene of the present invention is novel, suggesting a novel gene rather than an alternative splice form. Furthermore, the protein of the present invention lacks an LIM domain relative to gi8051618. The protein of the present invention does contain the kinase catalytic domain.

Approximately 40 LIM proteins, named for the LIM domains they contain, are known to exist in eukaryotes. LIM domains are conserved, cystein-rich structures that contain 2 zinc fingers that are thought to modulate protein-protein interactions. LIMK1 and LIMK2 are members of a LIM subfamily characterized by 2 N-terminal LIM domains and a C-terminal protein kinase domain. LIMK1 and LIMK2 mRNA expression varies greatly between different tissues. The protein kinase domains of LIMK1 and LIMK2 contain a unique sequence motif comprising Asp-Leu-Asn-Ser-His-Asn in subdomain VIB and a strongly basic insert between subdomains VII and VIII (Okano et al., *J. Biol. Chem.* 270 (52), 31321–31330 (1995)). The protein kinase domain present in LIMKs is significantly different than other kinase domains, sharing about 32% identity.

LIMK is activated by ROCK (a downstream effector of Rho) via phosphorylation. LIMK then phosphorylates cofilin, which inhibits its actin-depolymerizing activity, thereby leading to Rho-induced reorganization of the actin cytoskeleton (Maekawa et al., *Science* 285: 895–898, 1999).

The LIMK2a and LIMK2b alternative transcript forms are differentially expressed in a tissue-specific manner and are generated by variation in transcriptional initiation utilizing alternative promoters. LIMK2a contains 2 LIM domains, a PDZ domain (a domain that functions in protein-protein interactions targeting the protein to the submembranous compartment), and a kinase domain; whereas LIMK2b just has 1.5 LIM domains. Alteration of LIMK2a and LIMK2b regulation has been observed in some cancer cell lines (Osada et al., *Biochem. Biophys. Res. Commun.* 229: 582–589, 1996).

For a further review of LIMK proteins, see Nomoto et al., *Gene* 236 (2), 259–271 (1999).

Kinase proteins, particularly members of the serine/threonine kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the serine/threonine kinase subfamily.

SUMMARY OF THE INVENTION

The present invention is based in part on the identification of amino acid sequences of human kinase peptides and proteins that are related to the serine/threonine kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in humans in teratocarcinoma, ovary, testis, nervous tissue, bladder, infant and fetal brain, and thyroid gland.

DESCRIPTION OF THE FIGURE SHEETS

FIG. 1A–1B provide the nucleotide sequence of a cDNA molecule that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in teratocarcinoma, ovary, testis, nervous tissue, bladder, infant and fetal brain, and thyroid gland.

FIG. 2A–2B provide the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIGS. 3-1 to 3-30 provide genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 42 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the serine/threonine kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the serine/threonine kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the serine/threonine kinase subfamily and the expression pattern observed. Experimental data as provided in FIG. 1 indicates expression in humans in teratocarcinoma, ovary, testis, nervous tissue, bladder, infant and fetal brain, and thyroid gland. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known serine/threonine kinase family or subfamily of kinase proteins.

Specific Embodiments

Peptide Molecules

The present invention provides nucleic acid sequences that encode protein molecules that have been identified as being members of the kinase family of proteins and are related to the serine/threonine kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in humans in teratocarcinoma, ovary, testis, nervous tissue, bladder, infant and fetal brain, and thyroid gland. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. The gene encoding the novel kinase protein of the present invention is located on a genome component that has been mapped to human chromosome 22 (as indicated in FIG. 3), which is supported by multiple lines of evidence, such as STS and BAC map data.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genomic sequence mapped to the reference human. The gene encoding the novel kinase protein of the present invention is located on a genome component that has been mapped to human chromosome 22 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been found in the gene encoding the kinase protein of the present invention. SNPs were identified at 42 different nucleotide positions. Some of these SNPs, which are located outside the ORF and in introns, may affect gene transcription.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that the kinase proteins of the present invention are expressed in humans in teratocarcinoma, ovary, testis, nervous tissue, bladder, infant brain, and thyroid gland, as indicated by virtual northern blot analysis. In addition, PCR-based tissue screening panels indicate expression in fetal brain. A large percentage of pharmaceutical agents are being developed that modulate the activity of kinase proteins, particularly members of the serine/threonine kinase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in teratocarcinoma, ovary, testis, nervous tissue, bladder, infant and fetal brain, and thyroid gland. Such uses can readily be determined using the information provided herein, that which is known in the art, and routine experimentation.

The proteins of the present invention (including variants and fragments that may have been disclosed prior to the present invention) are useful for biological assays related to kinases that are related to members of the serine/threonine kinase subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that the kinase proteins of the present invention are expressed in humans in teratocarcinoma, ovary, testis, nervous tissue, bladder, infant brain, and thyroid gland, as indicated by virtual northern blot analysis. In addition, PCR-based tissue screening panels indicate expression in fetal brain.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in humans in teratocarcinoma, ovary, testis, nervous tissue, bladder, infant and fetal brain, and thyroid gland. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that the kinase proteins of the present invention are expressed in humans in teratocarcinoma, ovary, testis, nervous tissue, bladder, infant brain, and thyroid gland, as indicated by virtual northern blot analysis. In addition, PCR-based tissue screening panels indicate expression in fetal brain.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in humans in teratocarcinoma, ovary, testis, nervous tissue, bladder, infant and fetal brain, and thyroid gland. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in teratocarcinoma, ovary, testis, nervous tissue, bladder, infant and fetal brain, and thyroid gland. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in teratocarcinoma, ovary, testis, nervous tissue, bladder, infant and fetal brain, and thyroid gland. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, Rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the kinase proteins of the present invention are expressed in humans in teratocarcinoma, ovary, testis, nervous tissue, bladder, infant brain, and thyroid gland, as indicated by virtual northern blot analysis. In addition, PCR-based tissue screening panels indicate expression in fetal brain. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in teratocarcinoma, ovary, testis, nervous tissue, bladder, infant and fetal brain, and thyroid gland. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in teratocarcinoma, ovary, testis, nervous tissue, bladder, infant and fetal brain, and thyroid gland. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in teratocarcinoma, ovary, testis, nervous tissue, bladder, infant and fetal brain, and thyroid gland. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel kinase protein of the present invention is located on a genome component that has been mapped to human chromosome 22 (as indicated in FIG. 3), which is supported by multiple lines of evidence, such as STS and BAC map data.

FIG. 3 provides information on SNPs that have been found in the gene encoding the kinase protein of the present invention. SNPs were identified at 42 different nucleotide positions. Some of these SNPs, which are located outside the ORF and in introns, may affect gene transcription.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45C., followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 42 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel kinase protein of the present invention is located on a genome component that has been mapped to human chromosome 22 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the kinase proteins of the present invention are expressed in humans in teratocarcinoma, ovary, testis, nervous tissue, bladder, infant brain, and thyroid gland, as indicated by virtual northern blot analysis. In addition, PCR-based tissue screening panels indicate expression in fetal brain. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if a kinase gene has been mutated. Experimental data as provided in FIG. 1 indicates that the kinase proteins of the present invention are expressed in humans in teratocarcinoma, ovary, testis, nervous tissue, bladder, infant brain, and thyroid gland, as indicated by virtual northern blot analysis. In addition, PCR-based tissue screening panels indicate expression in fetal brain.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in humans in teratocarcinoma, ovary, testis, nervous tissue, bladder, infant and fetal brain, and thyroid gland. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that the kinase proteins of the present invention are expressed in humans in teratocarcinoma, ovary, testis, nervous tissue, bladder, infant brain, and thyroid gland, as indicated by virtual northern blot analysis. In addition, PCR-based tissue screening panels indicate expression in fetal brain. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in humans in teratocarcinoma, ovary, testis, nervous tissue, bladder, infant and fetal brain, and thyroid gland.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found in the gene encoding the kinase protein of the present invention. SNPs were identified at 42 different nucleotide positions. Some of these SNPs, which are located outside the ORF and in introns, may affect gene transcription. The gene encoding the novel kinase protein of the present invention is located on a genome component that has been mapped to human chromosome 22 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been found in the gene encoding the kinase protein of the present invention. SNPs were identified at 42 different nucleotide positions. Some of these SNPs, which are located outside the ORF and in introns, may affect gene transcription.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that the kinase proteins of the present invention are expressed in humans in teratocarcinoma, ovary, testis, nervous tissue, bladder, infant brain, and thyroid gland, as indicated by virtual northern blot analysis. In addition, PCR-based tissue screening panels indicate expression in fetal brain. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found in the gene encoding the kinase protein of the present invention. SNPs were identified at 42 different nucleotide positions. Some of these SNPs, which are located outside the ORF and in introns, may affect gene transcription.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1 982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules.

Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990) 119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed.*, Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed.*, Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule comprising a nucleotide sequence selected from the group consisting of:
   (a) a transcript or cDNA sequence that encodes a polypeptide having an amino acid sequence comprising SEQ ID NO:2;
   (b) SEQ ID NO:1;
   (c) nucleotides 229–993 of SEQ ID NO:1; and
   (d) a nucleotide sequence that is completely complementary to a nucleotide sequence of(a), (b), or (c).

2. An isolated nucleic acid molecule encoding serine/threonine wherein the nucleic acid molecule consists of a nucleotide sequence selected from the group consisting of:
   (a) a nucleotide sequence that encodes an amino acid sequence having at least 99% sequence identity to SEQ ID NO:2;
   (b) a nucleotide sequence having at least 99% sequence identity to SEQ ID NO:1;
   (c) a nucleotide sequence having at least 99% sequence identity to nucleotides 229–993 of SEQ ID NO:1; and
   (d) a nucleotide sequence that is completely complementary to a nucleotide sequence of(a), (b), or (c).

3. An isolated nucleic acid molecule encoding a serine/threonine kinase, wherein the nucleic acid molecule comprises a nucleotide sequence selected from the group consisting of:
   (a) a transcript or cDNA sequence that encodes an amino acid sequence having at least 99% sequence identity to SEQ ID NO:2;
   (b) a nucleotide sequence having at least 99% sequence identity to SEQ ID NO:1;
   (c) a nucleotide sequence having at least 99% sequence identity to nucleotides 229–993 of SEQ ID NO:1; and
   (c) a nucleotide sequence that is completely complementary to a nucleotide sequence of(a), (b), or (c).

4. An isolated nucleic acid molecule having a nucleotide sequence comprising SEQ ID NO:1 or the complement thereof.

5. An isolated nucleic acid molecule having a nucleotide sequence comprising nucleotides 229–993 of SEQ ID NO:1 or the complement thereof.

6. An isolated transcript or cDNA nucleic acid molecule comprising a nucleotide sequence that encodes a polypeptide comprising SEQ ID NO:2, or the complement of said nucleotide sequence.

7. The isolated nucleic acid molecule of claim 2, further comprising a heterologous nucleotide sequence.

8. The isolated nucleic acid molecule of claim 7, wherein the heterologous nucleotide sequence encodes a heterologous amino acid sequence.

9. A vector comprising the nucleic acid molecule of any one of claims 1–8.

10. An isolated host cell containing the vector of claim 9.

11. A process for producing a polypeptide comprising culturing the host cell of claim 10 under conditions sufficient for the production of said polypeptide, and recovering said polypeptide.

12. The vector of claim 9, wherein said vector is selected from the group consisting of a plasmid, a virus, and a bacteriophage.

13. The vector of claim 9, wherein said nucleic acid molecule is inserted into said vector in proper orientation and correct reading frame such that a polypeptide having at least 99% sequence identity to SEQ ID NO:2 is expressed by a cell transformed with said vector.

14. The vector of claim 13, wherein said isolated nucleic acid molecule is operatively linked to a promoter sequence.

* * * * *